United States Patent [19]
Morris et al.

[11] Patent Number: 5,293,218
[45] Date of Patent: Mar. 8, 1994

[54] INTERFEROMETRIC JFTOT TUBE DEPOSIT MEASURING DEVICE

[75] Inventors: Robert E. Morris, Silver Spring, Md.; Robert Wagner, Ann Arbor, Mich.

[73] Assignee: The United States of America as represented by the Secretary of the Navy, Washington, D.C.

[21] Appl. No.: 906,903

[22] Filed: Jun. 30, 1992

[51] Int. Cl.$^5$ .............................................. G01B 11/06
[52] U.S. Cl. .................................... 356/382; 356/355; 356/380
[58] Field of Search ............... 356/345, 355, 357, 380, 356/381, 382

[56] References Cited
U.S. PATENT DOCUMENTS 4,512,194  4/1985  Beuter ................................... 73/579
4,842,410  6/1989  Darrah et al. ...................... 356/357

Primary Examiner—F. L. Evans
Attorney, Agent, or Firm—Thomas E. McDonnell; John J. Karasek

[57] ABSTRACT

Jet fuels are tested for thermal stability by passing the fuel over a heated metal tube and measuring the amount of residue deposited as a film on the tube as a result of chemical changes to the fuel. The thickness distribution and volume of a deposited film on a tube are calculated by scanning the length of the tube with an optical probe, shining light onto the tube, measuring the intensity of reflected light of a preselected wavelength from the tube, and correlating the reflected light intensity with positions on the tube. The tube is then partially rotated, and the process is repeated until the entire surface of the tube is scanned. The volumes of each longitudinal slice of the tube are summed to give the total deposit volume on the tube.

20 Claims, 8 Drawing Sheets

INTERFEROMETRIC JFTOT TUBE DEPOSIT MEASURING DEVICE

BACKGROUND OF THE INVENTION

1. Field of the Invention

This invention relates to an improved device and process for measuring the thickness of thermal film deposits on JFTOT tubes, and more particularly to such a device and process using a computer controlled interferometer.

2. Description of the Related Art

Jet fuels undergo chemical changes when subjected to thermal stress, changes that can affect the performance of these fuels. Modern aircraft designs place thermal stress on fuels from a number of sources, such as heating from the engines and frictional heating from the wing surfaces. Consequently, there is an ongoing effort to develop thermally stable jet fuels and to characterize the thermal stability of available jet fuels.

The Jet Fuel Thermal Oxidation Test (JFTOT) is widely used in this effort. In this test, the fuel is passed over a heated metal tube under conditions of limited oxygen availability. The thermal stability of the fuel is characterized by the quantity of insoluble reaction products formed. When this test is performed in accordance with ASTM D3241, the total quantity of insoluble products formed is determined by measuring the amount of insoluble products adhereing to the outside of the heated tube (determined by comparing the color of the tube deposits to standard color charts) and the amount of particulate insoluble products in the fuel (determined by measuring the pressure drop across an in-line filter during the test).

Most fuels fail on the basis of tube deposits. Unfortunately, most of the uncertainty in the test method is attributable to the uncertainty in the measurement of tube deposits. The standard color comparison charts have proven to be quantitatively unreliable.

To increase the reliability of the test, the tube deposit rater (TDR) method was developed to measure tube deposits more accurately. In this method, the attenuation of reflected white light, measured by a photocell, is correlated to the deposit thickness. TDR eliminates the subjectivity inherent in the color chart comparisons, but the method can be compromised by variations in the optical properties of the deposit. Neither TDR nor color chart comparisons correlate well with deposit carbon content determined by combustion.

Other interferometric devices that can measure the deposit thickness on the tube are known. These devices use manual positioning of the probe along the length of the tube. There are several inherent problems with these devices.

One problem with these manual devices is the inability of an operator to position the probe along the tube with accuracy and repeatability. Another problem is that these devices are not equipped for rotating the tube to perform scans about the entire circumference of the tube. Without means for rotating the tube, and without means for positioning the probe relative to the tube with accuracy and repeatability, it is impossible to get accurate information on the radial distribution of a deposit on the tube. As will be shown below, the thermal deposits on JFTOT tubes can show significant radial asymmetry.

Moreover, these devices, because they rely on the human hand to position the probe, may miss significant features of the longitudinal distribution of the deposit on the tube. As will be shown below, significant deposit thickness variations can be found within a very few millimeters along the length of the tube.

Another disadvantage of these manual devices is that they lack an automated system for identifying peaks in the light intensity data, and computing deposit thickness and volume from this data. This lack of automated control and analysis increases the time and tedium inherent in measuring thermal deposits on JFTOT tubes.

Darrah et al., U.S. Pat. No. 4,842,410, describes such a manual interferometer, and is incorporated by reference herein.

SUMMARY OF THE INVENTION

Accordingly, it is an object of this invention to increase the accuracy of interferometric devices that measure thermal deposits on JFTOT heater tubes, so that the accuracy of these devices correlates well with deposit carbon content determined by combustion.

It is a further object of this invention to measure thermal deposits on JFTOT tubes to provide detailed information on both the radial and longitudinal distribution of deposits on these tubes.

It is a further object of this invention to precisely position an interferometric probe to improve the accuracy and repeatability of interferometric measurements of deposits on these tubes.

These and additional objects of the invention are accomplished by the structures and processes hereinafter described.

The Interferometric JFTOT Tube Deposit Measuring Device comprises an optical probe optically coupled to a light source and to a detector of reflected light, means for translating the optical probe along the length of the tube with accuracy and repeatability, means for rotating the tube with accuracy and repeatability, and means for calculating the deposit thickness profile and total deposit volume on the tube.

The means for calculating are coupled to the detector of reflected light, to use reflected light intensity data in calculating the deposit thickness profile and total deposit volume. The means for calculating are also coupled to the means for translating and the means for rotating, to use accurate data on the longitudinal position of the probe relative to the tube and on the rotational position of the tube in calculating the deposit thickness profile and total deposit volume.

BRIEF DESCRIPTION OF THE DRAWINGS

A more complete appreciation of the invention will be readily obtained by reference to the following Description of the Preferred Embodiments and the accompanying drawings in which like numerals in different figures represent the same structures or elements, wherein.

DESCRIPTION OF THE PREFERRED EMBODIMENTS

Figure 1:
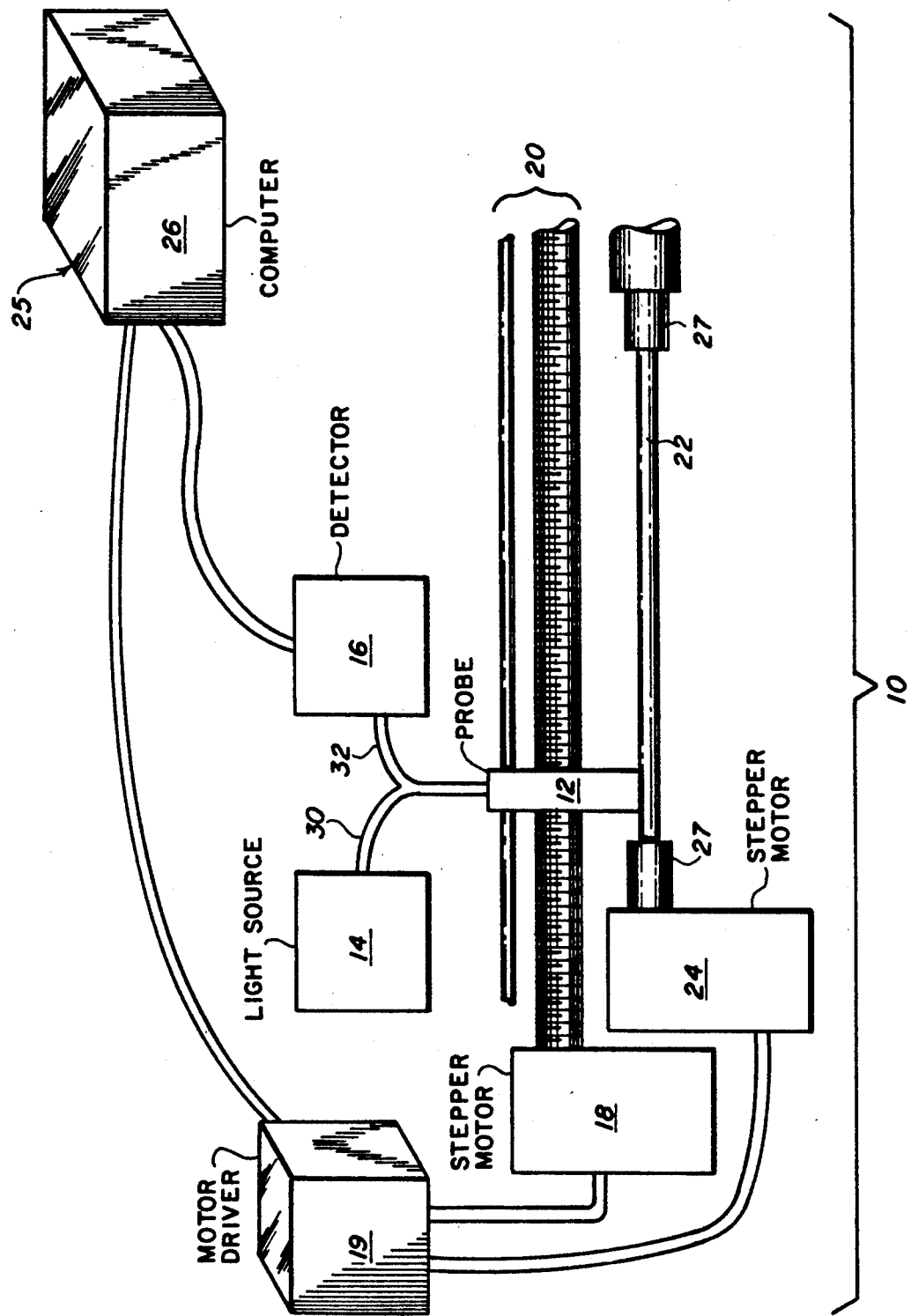
FIG. 1 is a representative view of a preferred embodiment of the Interferometric JFTOT Tube Deposit Measuring Device apparatus.

As described above, and as shown in FIG. 1, the Interferometric JFTOT Tube Deposit Measuring Device 10 comprises an optical probe 12 optically coupled to a light source 14 and to a detector of reflected light 16, means for translating the optical probe 12 parallel to the long axis of the tube 22 with accuracy and repeatability, means for rotating the tube 22 with accuracy and repeatability, and means for calculating the deposit thickness profile and total deposit volume on the tube 22.

As described above, and as shown in FIG. 1, the means for calculating are electrically coupled to the detector of reflected light, to use reflected light intensity data from the detector in calculating the deposit thickness profile and total deposit volume. The means for calculating are also coupled to the means for translating and the means for rotating, to use accurate data on the longitudinal position of the probe relative to the tube and on the rotational position of the tube in calculating the deposit thickness profile and total deposit volume.

In a preferred embodiment of the invention, the optical probe 12 supports and positions relative to the tube 22 a fiber optic waveguide 30 disposed to transmit light from the source 14 onto the tube 22. In a preferred embodiment of the invention, the optical probe 12 supports and positions relative to the tube 22 at least one fiber optic waveguide 32 disposed to receive light reflected from the tube and transmit this light to the detector 16.

In the most preferred embodiment, the probe 12 comprises a plurality of fiber optic waveguides 32 disposed to transmit light to the detector 16, arranged concentrically about the fiber optic waveguide 30 disposed to transmit light from the source 14, with all of these waveguides disposed in a sleeve.

Alternatively, a single fiber optic waveguide may be used both for transmitting light from the source 14 to the tube 22 and for transmitting light reflected from the tube 22 to the detector 16. In this embodiment of the invention, the single fiber would preferably be oriented essentially normal to the tube 22. Any of the general methods for combining and separating source and detector beams in a single fiber optic waveguide may be employed in this embodiment of the invention. These methods include using a bifurcated fiber or coupler which joins two fibers into one, using a partially reflecting mirror to split the source and reflected light, and using a spatial filter to separate the source and reflected light. See U.S. Pat. No. 4,792,689, issued Dec. 20, 1988 to Peterson, incorporated by reference herein.

In a preferred embodiment of the invention, the detector 16 comprises a phototransistor, a phototube, or a photomultiplier tube. The optical probe 12 preferably should be mounted so that the fiber optic waveguides 30, 32 connected to the source 14 and the detector 16 are aimed at the tube 22. It has been determined that no arrangement of lenses is needed to obtain accurate results, so long as the fiber optic waveguides are positioned with the waveguides connected to the detector in the path of reflected light from the source.

In a preferred embodiment, as shown in FIG. 1, the means for translating the probe 12 comprises a stepper motor 18 linked to a zero-backlash leadscrew assembly 20. In a preferred embodiment, as shown in FIG. 1, the means for rotating the tube 22 comprises another stepper motor 24. These stepper motors preferably are connected to the means for calculating, comprising a programmed digital computer 26, through one or more stepper motor drivers 19 for controlling the stepper motors so that accurate data on the longitudinal position of the probe 12 relative to the tube 22 and on the rotational position of the tube 22 may be used in calculating the deposit thickness profile and total deposit volume.

In operation, the optical probe 12 traverses the length of the tube 22. As the probe 12 moves along the tube 22, light from the source 14 shines onto the tube 22, and reflected light of a predetermined wavelength is detected by the detector 16. This can be carried out either by using an essentially monochromatic light source, or by filtering the reflected light to make it essentially monochromatic. The variations in the reflected light intensity are measured as the probe 12 scans across the tube 22. From these variations in the reflected light intensity, the deposit thickness profile along the length of the tube is calculated, as described below. From this deposit thickness profile, the volume of the tube deposit is computed by numerical integration.

After the length of the tube 22 is scanned, the tube 22 is partially rotated, and the scanning process is repeated. This translation and rotation cycle is repeated until the entire surface of the tube 22 has been scanned, i.e. until the tube has been rotated 360°. The deposit volumes for each longitudinal slice of the tube are then summed to give the total deposit volume for the tube 22.

Figure 2:
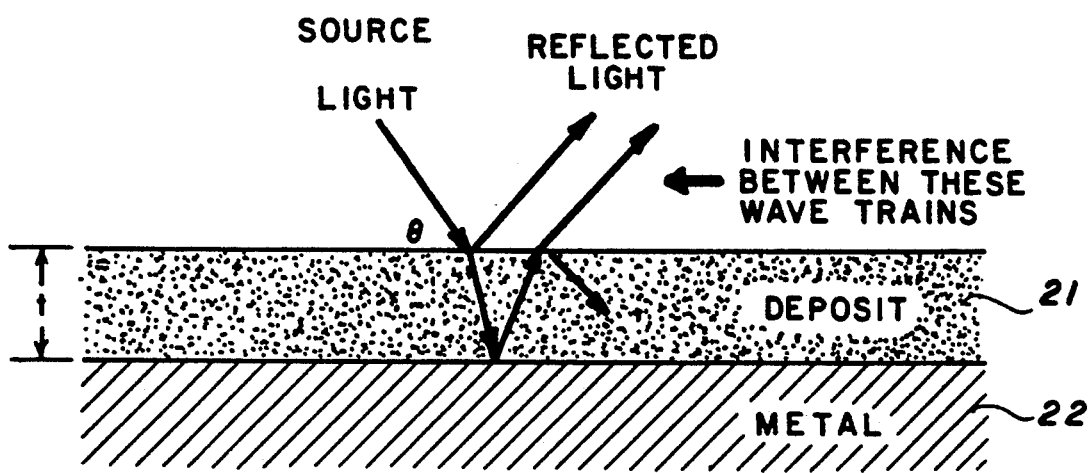
FIG. 2 is a representative view of the paths of the interfering light paths reflected from the surfaces of the tube and the deposited film.

FIG. 2 illustrates the principle of interference that is used in this invention to measure deposit thickness. In this invention, source light impinges on the deposit surface at an angle $\theta$. A portion of the source light is reflected back from the interface and a portion passes into the deposit. The light that passes into the deposit is reflected off the metal surface of the tube. The light reflected from the metal surface passes back out of the tube, where it interferes with the light reflected from the surface of the deposit.

Two effects are observed as the source light impinges on increasingly thick deposits (i.e. as the optical probe moves from areas of thin deposits to areas of thick deposits). The first effect is that as the path length of the light in the film changes, the measured interference pattern changes. When the difference between the two path lengths is equal to one-half the wavelength of the source light, the light reflected from the tube surface is completely out of phase with the light reflected from the film surface, and the two light paths interfere destructively. As the film thickens to where the path length difference is equal to one wavelength, the light reflected from the tube surace is perfectly in phase with the light reflected from the film surface, and the two light paths interfere constructively. Thus, as the film thickens, a regular cycle of maxima and minima (generically referred to as peaks) is observed in the intensity of the reflected light.

Figure 3:
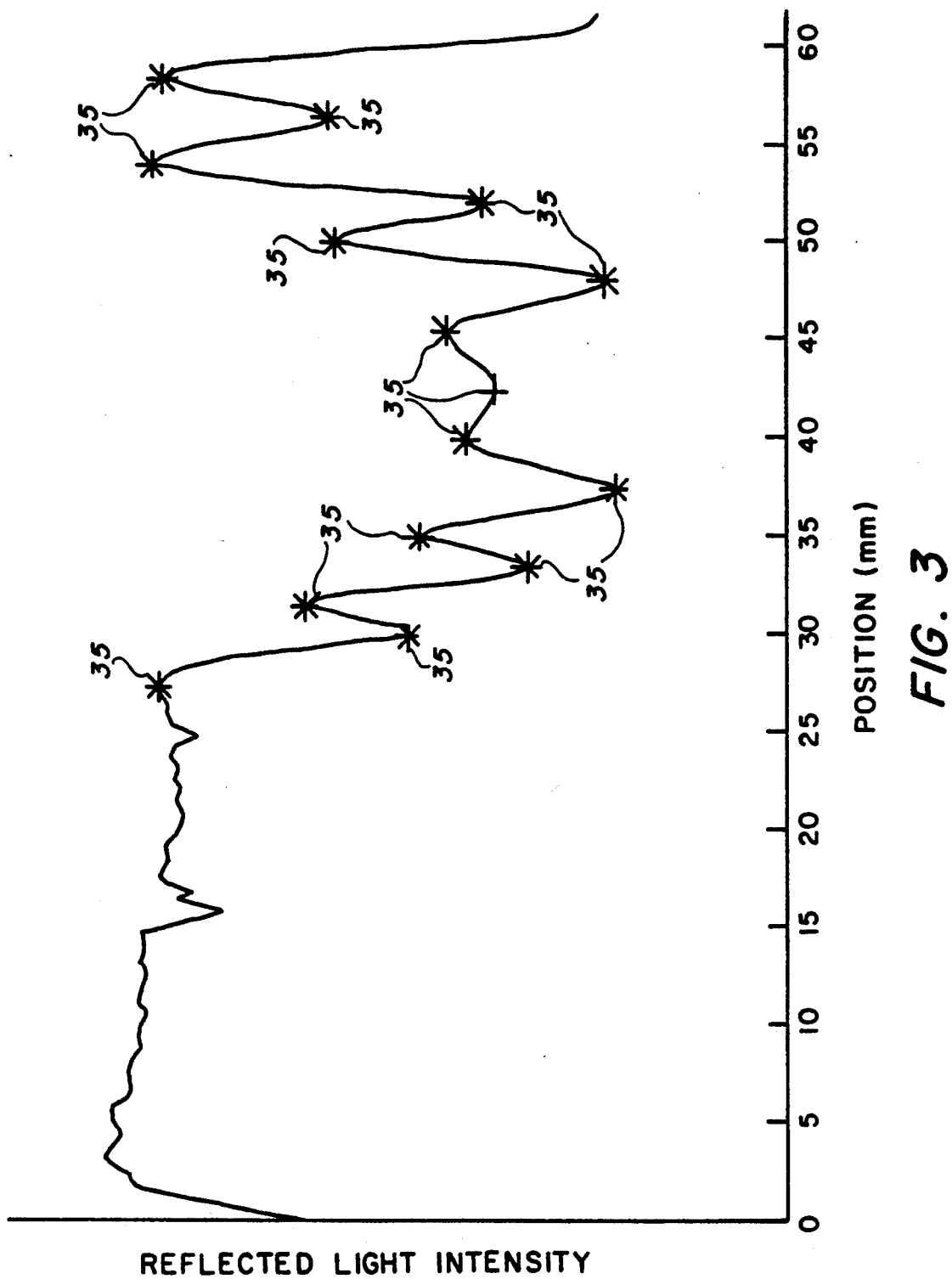
FIG. 3 shows reflected light intensities on a typical aluminum tube.

The other observed effect is the attenuation of the light passing through the deposit, according to Lambert's law. The net observed effect then, is a series of oscillations superimposed on a baseline which decreases as the deposit thickens and increases as the deposit thins. The thickness of the film is thus given by equation 1., $$t = \frac{m\lambda}{2n\cos\theta} \quad (1)$$

where m is an integer thickness multiplier related to the number of cycles in the reflected light intensity, $\lambda$ is the wavelength of the reflected light, n is the refractive index of the deposit, and $\theta$ is the angle of light incidence. A typical pattern of peaks 35 in the reflected light intensity on a JFTOT tube is shown in FIG. 3. The pattern of peaks 35 in FIG. 3 shows a series of oscillations superimposed on a baseline which is characteristic of a deposit on a tube that is thinner at the ends of the tube and thicker in the middle of the tube. By calculating the deposit thickness at each of the observed peaks in the reflected light intensity, and correlating these thicknesses with positions on the tube, the deposit thickness profile is determined.

The refractive index for a typical jet fuel deposit is 1.6; refractive indices may be determined for particular deposits by immersing the deposit in liquids of known, progressively higher refractive indices until no interference is observed. Errors from nonuniform refractive indices in films are observed to be within the limits of the errors of other methods.

Figure 4:
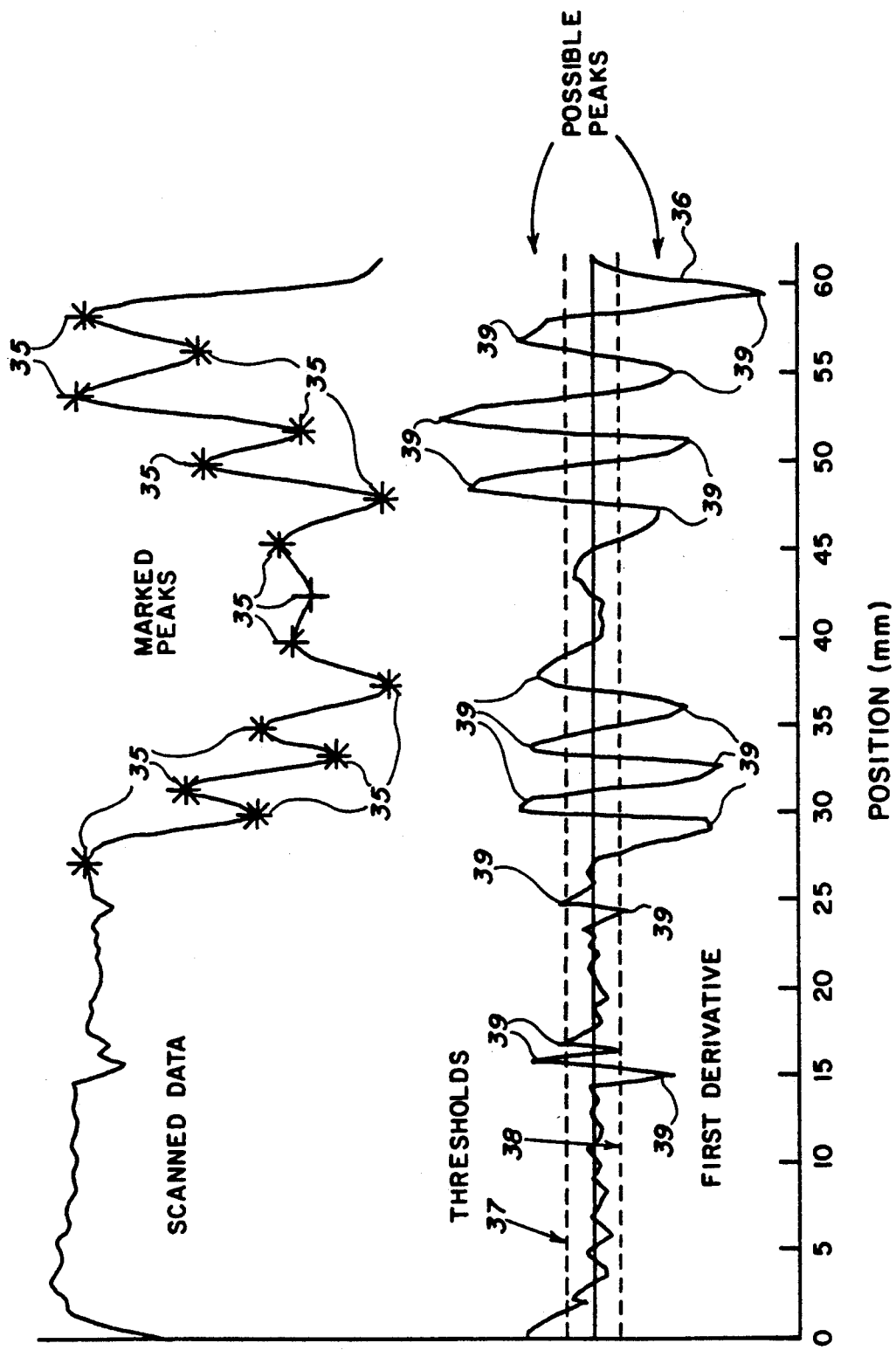
FIG. 4 shows the first derivative of reflected light intensity with respect to position on the tube.

In a preferred embodiment of the invention, the peaks 35 are recognized by analyzing the first derivative of the reflected light intensity, dI/dx 36, as shown in FIG. 4. At each point on the slice where the first derivative 36 goes above or below set thresholds 37, 38, this point is labelled as a possible peak 39. The possible peak widths, measured by the full-width-at-half-maximum method, are then compared to preset thresholds. If the possible peak 36 is neither too wide nor too narrow, it is labelled as a peak 35.

In a most preferred embodiment of the invention, an operator is prompted with the labelled peaks 35, and is able to add or remove labelled peaks.

For a typical jet fuel thermal deposit on a tube 22, the deposit 21 has a thickness of effectively zero at each end of the tube, and reaches a maximum thickness somewhere between the two ends. Therefore, in a preferred embodiment of the invention, m, the integer thickness multiplier, will equal one at the first scanned peak on a slice, and will increase by one at each subsequent peak, until the deposit reaches its maximum thickness on that slice. Thereafter, m will decrease by one at each peak, until it reaches the last scanned peak on the slice.

Figure 5:
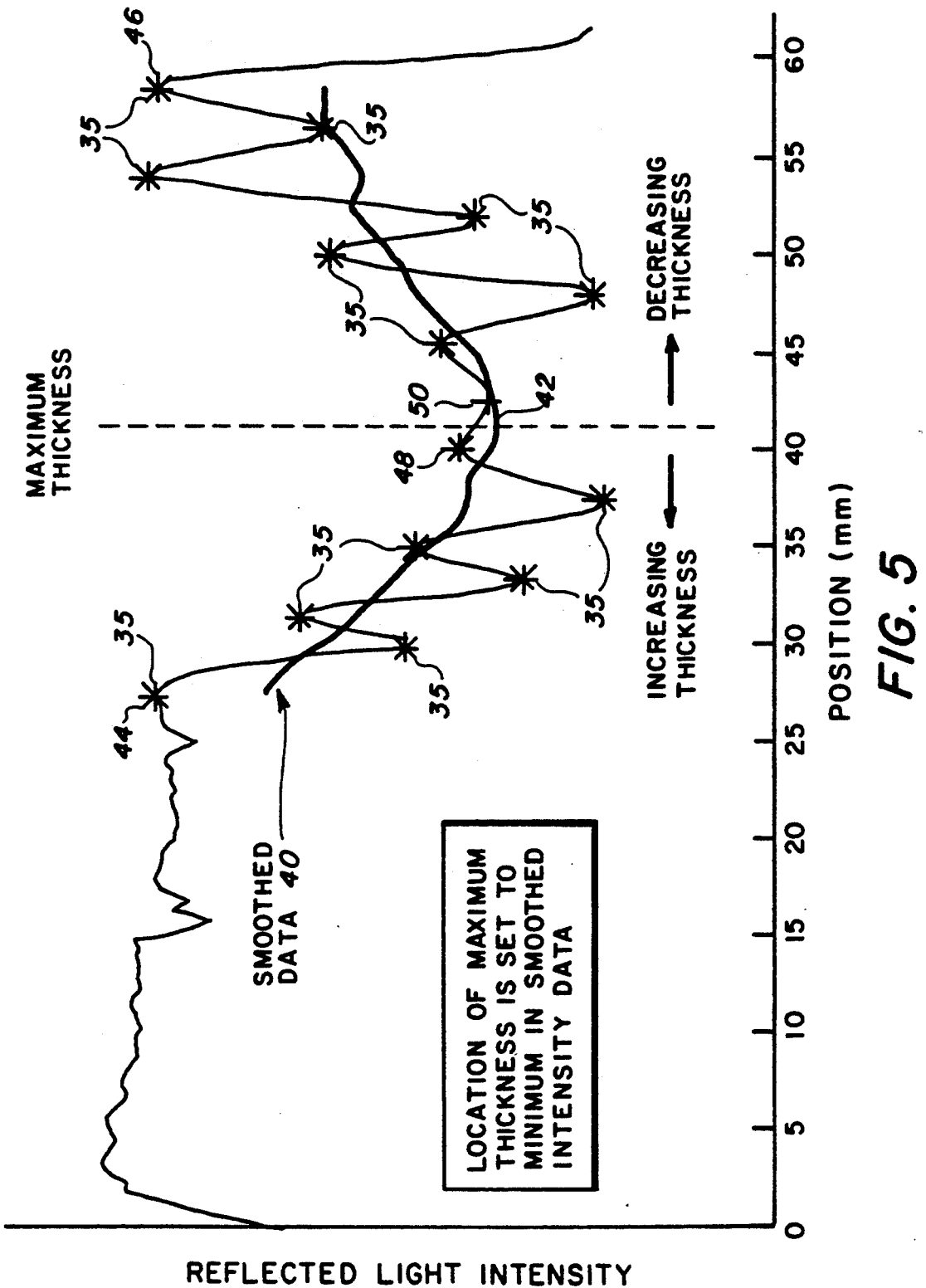
FIG. 5 shows the moving average of reflected light intensities on a typical aluminum tube.

In a preferred embodiment of the invention, the point of maximum deposit thickness on a slice of the tube is determined by computing a moving average 40 of the reflected light intensity, thereby smoothing the light intensity data. This is shown in FIG. 5. The minimum intensity point 42 on this smoothed curve is taken to be the point of maximum deposit thickness. Thus, m will be increasing from the first peak 44 to this point and decreasing from this point to the last peak 46.

In a most preferred embodiment, in the case where the peaks immediately on either side of the minimum intensity point 42 are further apart than a predetermined limit, m will be increasing from the first peak 44 to the peak immediately preceding the point of minimum intensity 48, where it will reach its maximum value. It (m) will keep this value for the next peak 50 (i.e. the peak immediately following the point of minimum intensity). For subsequent peaks, m will be decreasing. Thus, there will be two equal peaks of maximum deposit thickness on this slice of the tube.

Figure 6:
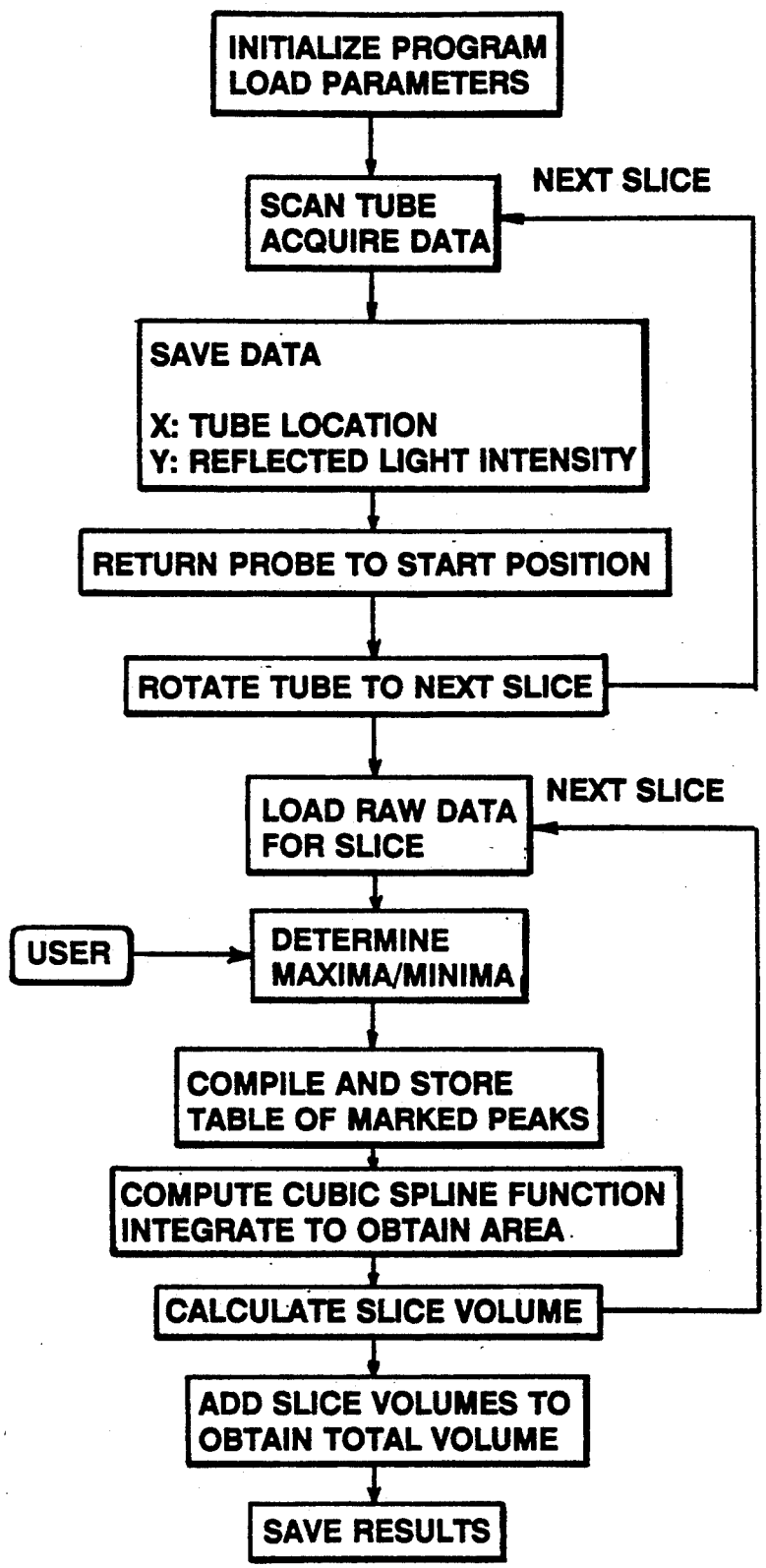
FIG. 6 shows the basic steps in the Interferometric JFTOT Tube Deposit Measuring Device control software.

The flowchart shown in FIG. 6 illustrates the preferred sequence of steps carried out by the computer system in measuring a deposit on a tube.

It has been determined that the deposit thickness distribution along the length of a stainless steel tube roughly follows a gaussian curve near the fuel inlet end of the tube and a parabolic curve near the fuel outlet end of the tube. The deposit thickness distribution along the length of an aluminum tube is more symmetrical, roughly following a parabolic curve at both ends of the tube. These distributions can be fit to a smooth curve using a cubic spline. Therefore, in a preferred embodiment of the invention, the calculated deposit thicknesses on each slice are fit to a cubic spline curve. It has been experimentally confirmed that deposit volumes computed using a cubic spline fit correlate well with deposit volumes computed by the total carbon combustion method.

Figure 7:
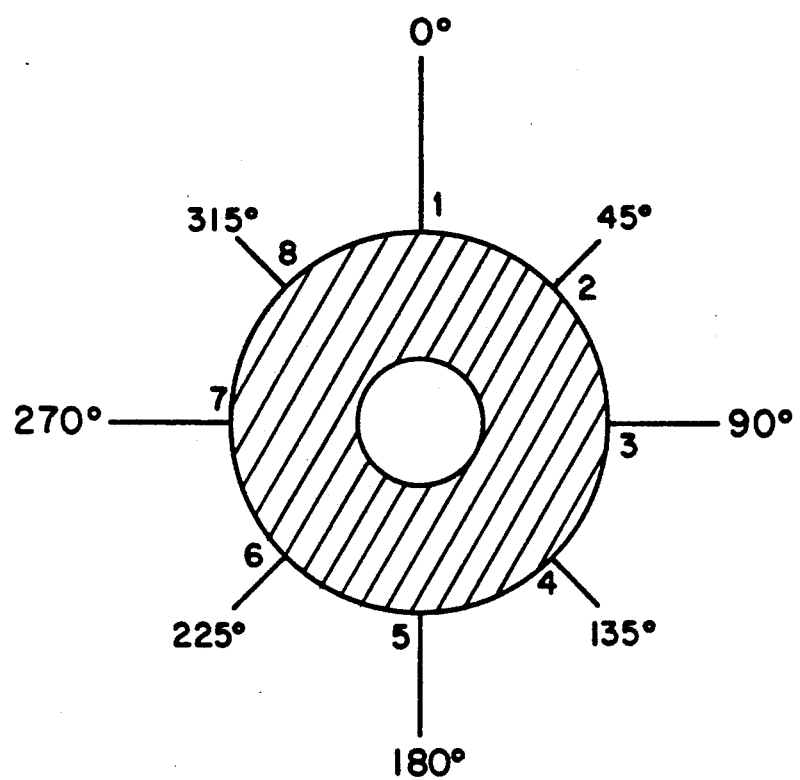
FIG. 7 is a cross-sectional view of a tube, showing typical slice designations for longitudinal scans of the tube.

The deposit volume is determined by making several longitudinal scans taken down the tube. As shown in FIG. 7, with d measurements taken around the circumference, an arcuate portion of the tube equal to $2\pi/d$ is defined as a slice. Given a deposit of thickness t (which will vary along the length of the tube) on a cylindrical tube of radius r and length L, the volume of the deposit is given by $$V = \int_0^L \int_0^{\frac{2\pi}{d}} \int_r^{r+t} r\, dr\, d\phi\, dz \quad (2)$$

where d is the number of scans taken around the tube circumference. Integrating over the specified limits, the volume of the slice is given by $$V_{slice} = \frac{\pi L(2rt + t^2)}{d} \quad (3)$$

For an area A under the thickness profile curve, A=Lt. Substituting t=A/L into (3) yields $$V_{slice} = \frac{\pi\left(2rA + \frac{A^2}{L}\right)}{d} \quad (4)$$

The sum of the slice volumes is equal to the total deposit volume on the tube.

In a preferred embodiment, the invention operates at a wavelength that is short enough to provide good resolution, but long enough so that electronic absorptions of the incident light by the deposit are not observed. The preferred wavelength range is from about 300 nm to about 600 nm. Preferred light sources 14 for the optical system include filtered xenon arc lamps, filtered mercury lamps, lasers and light emitting diodes.

The most preferred wavelength is at about 460 nm, which corresponds to the shortest wavelength primary spectral line in the xenon spectrum. When the invention is operated at this wavelength, an inexpensive xenon arc lamp may be used as the light source 14.

Having described the invention, the following examples are given to illustrate specific applications of the invention, including the best mode now known to perform the invention. These specific examples are not intended to limit the scope of the invention described in this application.

EXAMPLES

Example 1

Analysis of a Deposit on a 60 mm Aluminum Tube

A 60 mm long aluminum JFTOT tube was inserted in an apparatus to thermally stress jet fuels according to ASTM D3241. A jet fuel was stressed according to this standard.

An IBM-compatible computer 26 with an Intel 80386 microprocessor was loaded with the BASIC language programs NRL-IMD.BAS, ANALYZER.BAS, SCANNER.BAS, and PRINTER.BAS. Listings of these programs are below.

A circuit board made by Metrabyte, model number DASH-16 25, was inserted into an empty slot in the computer 26. This board is an analog-to-digital converter (ADC). A phototransistor 16 was connected to an amplifying circuit that applied the appropriate voltage to the input for the ADC. The phototransistor 16 was positioned to receive light transmitted through detector fiber optic waveguides 32.

An Arrick Robotics Stepper Motor Kit Model MD-2 provides two stepper motors 18, 24, and a dual stepper motor driver 19. The input for the dual stepper motor driver from this kit was plugged into the LPT1 port of the computer 26. The driver outputs were plugged into the inputs for the two stepper motors from this kit. One of these stepper motors 23 was linked to a mounting assembly 27 for receiving the JFTOT tube 22; this stepper motor was used to rotate the tube. The other stepper motor 18 was linked to a leadscrew assembly table 20 manufactured by Techno, model number HL315BMZ181B. This leadscrew assembly table provides 2 mm of translation per rotation. The optical probe 12 was mounted on this leadscrew assembly 20.

A xenon arc lamp manufactured by PTI was used as the light source 14. The lamp was filtered so that only the principal line at 460 nm was transmitted through a source fiber optic waveguide 30 to the optical probe. The lamp was powered by a PTILPS200 Universal Power Supply and housed in a PTI A1000 Arc Lamp Housing. The entire apparatus, other than the computer, was mounted inside a box with a hinged lid, to reduce the amount of stray light in the system.

Figure 8:
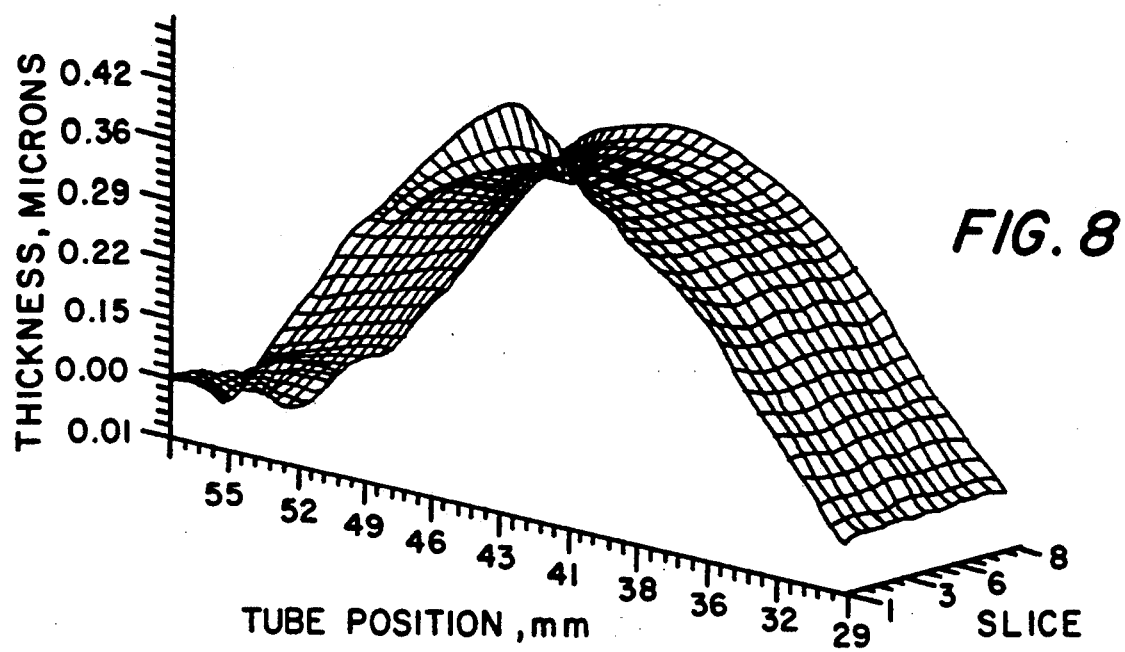
FIG. 8 shows the results of an analysis on an aluminum JFTOT tube.

The aluminum JFTOT tube 22 with the thermal deposit 21 was mounted in the apparatus. The computer programs were run. Eight evenly-spaced scans were performed about the circumference of the tube. The results are graphically shown in FIG. 8. As shown in FIG. 8, the deposit thickness reached a maximum thickness of about 0.48 $\mu$m on slice 1 at about 43 mm down the length of the tube. At this same distance down the tube, slices 3 through 6 only showed a maximum thickness of about 0.40 $\mu$m.

Example 2

Analysis of a Deposit on a Steel Tube

A steel JFTOT tube was inserted in an apparatus to thermally stress jet fuels. A jet fuel was stressed essentially according to this standard, the sole deviation from the standard being the use of the steel tube instead of a 60 mm aluminum tube. The steel JFTOT tube 22 with the thermal deposit 21 was mounted in the apparatus.

Figure 9:
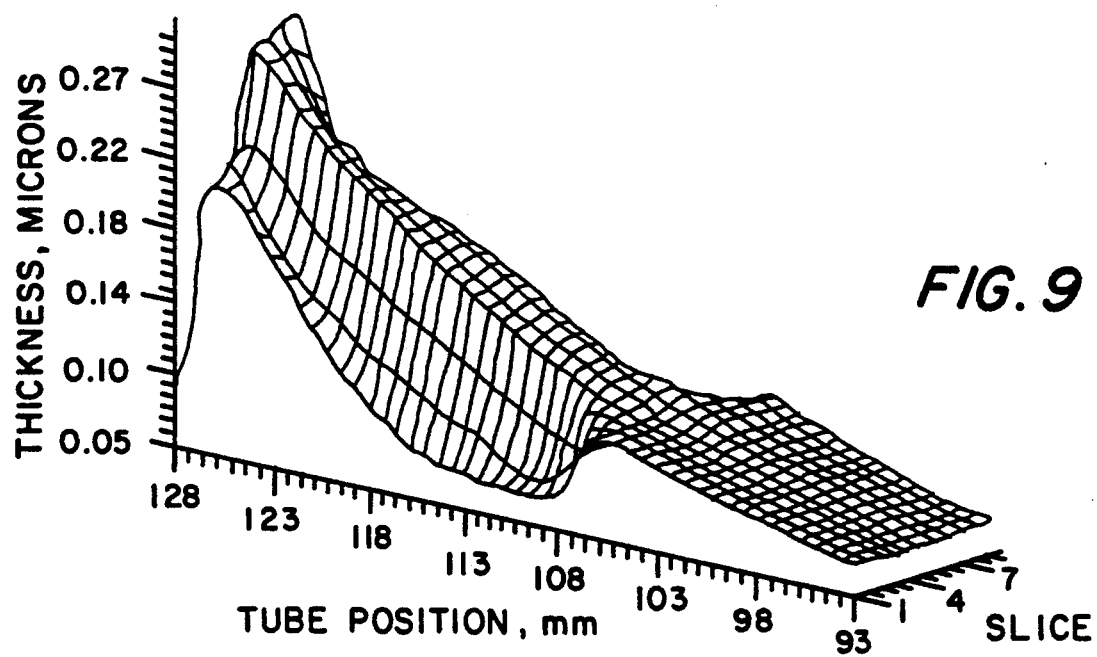
FIG. 9 shows the results of an analysis on a steel JFTOT tube.

In all other respects, this experiment was conducted as described in Example 1. The results are shown graphically in FIG. 9. As shown in FIG. 9, the deposit thickness reached a maximum thickness of about 0.31 $\mu$m on slice 7 at about 126 mm down the length of the tube. At this same distance down the tube, slice 1 only showed a maximum thickness of about 0.21 $\mu$m. As further shown in FIG. 9, the thickness of slice 1 changed from about 0.12 $\mu$m at about 106 mm down the tube to about 0.07 $\mu$m at about 108 mm down the tube. The thickness of slice 1 also changed from about 0.21 $\mu$m at about 126 mm down the tube to about 0.13 $\mu$m at about 127 mm down the tube.

These examples show that significant differences can be observed in the thickness of the deposit on the tube at different points on the circumference of the tube. This illustrates the need for scanning the entire surface of the tube, not just a single longitudinal slice, to get accurate information on the thickness and volume of films deposited on JFTOT heater tubes. These examples also show that significant features in the thickness profile along a slice of a tube may be missed without a highly accurate method for positioning the optical probe and analyzing the data from the probe.

Obviously, many modifications and variations of the present invention are possible in light of the above teachings. For instance, an obvious modification of the invention would be to a polychromatic light source and to filter the reflected light so that only a single wavelength of reflected light is measured. Another obvious modification of the invention would be to perform iterative scans about the circumference of the tube, and advancing the probe along the length of the tube after each circumferential scan. It is therefore to be understood that, within the scope of the appended claims, the invention may be practiced otherwise than as specifically described.

```
'*************************************************************
'*************************************************************
'******                                                 ******
'******       NRL Interferometric Measuring Device      ******
'******                     Version 2                   ******
'******                                                 ******
'******         Written by: Robert Wagner    7-21-89    ******
'******                     Modified:  7-18-91          ******
'******                                                 ******
'*************************************************************
'*************************************************************

DECLARE SUB check.name.path (check$, file$, path$, name$)
COMMON tube.path$, tube.name$, save.tube$, peak.path$, peak.name$, save.peak$
COMMON spline.path$, spline.name$, save.spline$, volume.path$, volume.name$
COMMON save.volume$, config.path$, config.name$, save.config$, slice
COMMON number, dist.interval, step.interval, type.tube$, scan.start, scan.end
COMMON length, motor.ports, translator, rotator, tran.speed, rot.speed
COMMON tran.rev, rot.rev, screw.rev, sample, timer.rate, n1, n2, timer.freq
COMMON low.scan, high.scan, io.add, interrupt, dma.level, thickness, errtol
COMMON incout, max.pk.wid, min.pk.wid, pos.thresh, neg.thresh, max.consec
COMMON min.plateau, move.average, find.peaks, printer.port$
COMMON scrtype$, key.break$, scr, alum.start, alum.end, alum.length
COMMON steel.start, steel.end, steel.length, base.path$, base.name$ COMMON tube.exten$, peak.exten$, spline.exten$, volume.exten$, config.exten$
COMMON already.running$, xaxismin, xaxismax, yaxismin, yaxismax, ticky, marky
COMMON current.menu$, max.number, max.slices, max.samples, program.version '--------------- Initial Set-up ---------------

IF already.running$ <> "y" THEN CLEAR , , 5000    'when the program starts, reset the stack size to 5000
CLS
ON ERROR GOTO error.handler program.version = 2                '2nd version of the program xaxismin = 30                      'sets left-most point for graphics display
xaxismax = 635                     'sets right-most point for graphics display
max.number = 2600                  'sets maximum number of data points per slice
max.slices = 100                   'sets maximum number of slices
max.samples = 1000                 'set maximum number if samplings per data point tube.exten$ = ".TUB"               'sets data file extensions:
peak.exten$ = ".PK"
spline.exten$ = ".SPL"
volume.exten$ = ".VOL"
```

```
config.exten$ = ".CON"
DIM menu.color(23)                              'array used in menu screens '------------- Load Defaults -----------------

'---------- check to see if program is just starting or returning from CHAINed Analyzer, Printer, or Scanner -----------

IF already.running$ <> "y" THEN
    current.menu$ = "main"
    config.path$ = ""
    config.name$ = "DEF"

OPEN config.path$ + config.name$ + config.exten$ FOR INPUT AS #1
    INPUT #1, tube.path$
    INPUT #1, tube.name$
    INPUT #1, save.tube$
    INPUT #1, peak.path$
    INPUT #1, peak.name$
    INPUT #1, save.peak$
    INPUT #1, spline.path$
    INPUT #1, spline.name$
    INPUT #1, save.spline$
    INPUT #1, volume.path$
    INPUT #1, volume.name$
    INPUT #1, save.volume$
    INPUT #1, config.path$
    INPUT #1, config.name$
    INPUT #1, save.config$
    INPUT #1, slice
    INPUT #1, number
    INPUT #1, dist.interval
    INPUT #1, step.interval
    INPUT #1, type.tubes
    INPUT #1, scan.start
    INPUT #1, scan.end
    INPUT #1, length
    INPUT #1, motor.port$
    INPUT #1, translator
    INPUT #1, rotator
    INPUT #1, tran.speed
    INPUT #1, rot.speed
    INPUT #1, tran.rev
    INPUT #1, rot.rev
    INPUT #1, screw.rev
    INPUT #1, sample
    INPUT #1, timer.rate
    INPUT #1, n1
    INPUT #1, n2
    INPUT #1, timer.freq
    INPUT #1, low.scan
```

```
    INPUT #1, high.scan
    INPUT #1, io.add
    INPUT #1, interrupt
    INPUT #1, dma.level
    INPUT #1, thickness
    INPUT #1, errtol
    INPUT #1, incout
    INPUT #1, max.pk.wid
    INPUT #1, min.pk.wid
    INPUT #1, pos.thresh
    INPUT #1, neg.thresh
    INPUT #1, max.consec
    INPUT #1, min.plateau
    INPUT #1, move.average
    INPUT #1, find.peak$
    INPUT #1, printer.port$
    INPUT #1, scrtype$
    INPUT #1, key.break$
    INPUT #1, file.version$
    INPUT #1, file.date$
    INPUT #1, scr
    INPUT #1, alum.start
    INPUT #1, alum.end
    INPUT #1, alum.length
    INPUT #1, steel.start
    INPUT #1, steel.end
    INPUT #1, steel.length
    INPUT #1, base.path$
    INPUT #1, base.name$
    CLOSE #1
    already.running$ = "y"
END IF min.samp.rate = (timer.freq / 65535) / 65535        'sets the minimum sampling rate
max.samp.rate = timer.freq / 4                      'sets the maximum sampling rate SELECT CASE scrtype$
    CASE "Mono"
        scr = 2                  'set screen mode to 2 - Monochrome
        yaxismin = 13            'set minimum y position for graphical display
        yaxismax = 169           'set maximum y position for graphical display
        ticky = 188              'sets y position of tick mark below x-axis
        marky = 193              'sets y position of marked peaks
    CASE "Hi-Res Color"
        scr = 9                  'set screen mode to 9 - Color
        yaxismin = 30            'set minimum y position for graphical display
        yaxismax = 296           'set maximum y position for graphical display
        ticky = 333              'sets y position of tick mark below x-axis
        marky = 340              'sets y position of marked peaks
END SELECT
```

```
'--------- Main Program ---------
   SELECT CASE current.menu$
      CASE "main"
              GOSUB main
      CASE "config"
              GOSUB config
      CASE "disk"
              GOSUB disk
   END SELECT DO
   LOOP
END
'--------- Subroutines --------- error.handler:                                    'handles errors
   SELECT CASE ERR
      CASE 53                                     'file not found error
         okay$ = "n"
      CASE 61                                     'disk full error
         BEEP
         PRINT
         PRINT TAB(28); "The Current Disk is Full"
         PRINT
         PRINT TAB(15); "press any key to return to the main menu ";
         which$ = UCASE$(INPUT$(1))
         CLOSE
         full.quit$ = "y"
      CASE 52, 64                                 'bad file name error
         okay$ = "n"
      CASE 71
         BEEP
         PRINT
         PRINT TAB(30); "The Disk is Not Ready"
         PRINT
         PRINT TAB(20); "press any key to try again or Q) to quit"
         zz$ = UCASE$(INPUT$(1))
         IF zz$ = "Q" THEN END
      CASE 76                                     'path not found error
         CLOSE
         path.quit$ = "y"
      CASE ELSE
         BEEP
         PRINT
         PRINT "Error "; ERR; " occurred.  Program aborted."
         PRINT
```

'goto active menu

```
            CLOSE                       'close all files
            STOP
        END SELECT
    RESUME NEXT keys.off:                               'turns off key trapping
    FOR x = 1 TO 25
        KEY(x) OFF
    NEXT x
    RETURN quit:
    GOSUB keys.off
    CLOSE                               'close all files
    PRINT
    PRINT TAB(21); "Are you sure you want to quit (Y/N)? ";
    leave$ = UCASE$(INPUT$(1))
    PRINT leave$
    IF leave$ = "Y" THEN END            'exit program on ESC
RETURN '---------------------- main menu ---------------------- main:
    current.menu$ = "main"              'set current menu to main menu
    GOSUB main.menu.init                'initialize key trapping routines
    GOSUB main.menu.on                  'turn key trapping on
    GOSUB main.menu                     'display main menu
RETURN main.menu.init:                         'initialize key trapping routines KEY 15, CHR$(160) + CHR$(72)        'up--up
    KEY 16, CHR$(160) + CHR$(75)        'left--up
    KEY 17, CHR$(160) + CHR$(77)        'right--down
    KEY 18, CHR$(160) + CHR$(80)        'down--down
    KEY 19, CHR$(32)  + CHR$(31)        'S--scan
    KEY 20, CHR$(32)  + CHR$(30)        'A--analyze
    KEY 21, CHR$(32)  + CHR$(28)        'RET-change
    KEY 25, CHR$(32)  + CHR$(1)         'ESC-quit ON KEY(2)  GOSUB config             'F2--goto config menu
    ON KEY(3)  GOSUB printing           'F3--goto print menu
    ON KEY(4)  GOSUB disk               'F4--goto disk/hardware menu
    ON KEY(11) GOSUB mm.up              'up(cursor)--move up one menu item
    ON KEY(12) GOSUB mm.up              'left(cursor)--move up one menu item
```

```
ON KEY(15) GOSUB mm.up              'up(keypad)--move up one menu item
ON KEY(16) GOSUB mm.up              'left(keypad)--move up one menu item
ON KEY(13) GOSUB mm.down            'right(cursor)--move down one menu item
ON KEY(14) GOSUB mm.down            'down(cursor)--move down one menu item
ON KEY(17) GOSUB mm.down            'right(keypad)--move down one menu item
ON KEY(18) GOSUB mm.down            'down(keypad)--move down one menu item
ON KEY(19) GOSUB scanning           'S--scan tube
ON KEY(20) GOSUB analyze            'A--analyze tube
ON KEY(21) GOSUB mm.change          'RET--select menu item
ON KEY(25) GOSUB mm.quit            'ESC--quit program FOR x = 1 TO 7                      'deselect menu items (low intensity white)
    menu.color(x) = 7
NEXT x
menu.color(1) = 15                  'hilight 1st menu item (high intensity white)
menu.pos = 1                        'set menu position to 1st menu item
RETURN main.menu.on:
    FOR x = 11 TO 21                'turn on key trapping
        KEY(x) ON
    NEXT x
    KEY(2) ON
    KEY(3) ON
    KEY(4) ON
    KEY(25) ON
RETURN main.menu:                          'display main menu
CLS
PRINT "             NRL - Interferometric Measuring Device Program v."; program.version
PRINT "-------------------------------------------------------------------------------"
PRINT
COLOR menu.color(1): PRINT TAB(10); "Number of Slices";
COLOR 7: PRINT TAB(50); slice
COLOR menu.color(2): PRINT TAB(10); "Number of Points per Slice";
COLOR 7: PRINT TAB(50); number
COLOR menu.color(3): PRINT TAB(10); "Distance Between Points";
COLOR 7: PRINT TAB(50); dist.interval; " mm  ("; LTRIM$(STR$(INT(10 * step.interval) / 10)); " steps)"
COLOR menu.color(4): PRINT TAB(10); "Type of Tube";
COLOR 7: PRINT TAB(50); type.tube$
PRINT
COLOR menu.color(5): PRINT TAB(10); "Data File Extension/Name";
COLOR 7: PRINT TAB(40); base.path$ + base.name$
COLOR menu.color(6): PRINT TAB(10); "Disk Directory"
COLOR menu.color(7): PRINT TAB(10); "Delete Files"
COLOR 7
LOCATE 16
PRINT TAB(20); "S--Scan Tube"; TAB(40); "A--Analyze Tube"
PRINT
```

```
        PRINT
        PRINT "F2-Configuration Menu   F3-Print Menu   F4-Disk/Hardware Menu   ESC-Quit"
RETURN printing:
        print.or.analyze$ = "print"
        GOSUB print.analyze
RETURN analyze:
        print.or.analyze$ = "analyze"
        GOSUB print.analyze
RETURN mm.quit:
        GOSUB quit                              'exit program
        GOSUB main.menu.on                      'otherwise turn key trapping on
        GOSUB main.menu                         'display main menu
RETURN mm.up:
        IF menu.pos = 1 THEN                    'move up one menu item
            menu.pos = 7                        'if cursor is at first item, move to last
            menu.color(1) = 7
        ELSE
            menu.pos = menu.pos - 1             'otherwise move cursor up
            menu.color(menu.pos + 1) = 7
        END IF
        menu.color(menu.pos) = 15               'hilight menu item
        GOSUB main.menu
RETURN mm.down:
        IF menu.pos = 7 THEN                    'move down one menu item
            menu.pos = 1
            menu.color(7) = 7
        ELSE
            menu.pos = menu.pos + 1
            menu.color(menu.pos - 1) = 7
        END IF
        menu.color(menu.pos) = 15
        GOSUB main.menu
RETURN mm.change:
        GOSUB keys.off
        SELECT CASE menu.pos
            CASE 1                              'select menu item
                LOCATE 22
                COLOR 15
                PRINT TAB(27); "select from 1-100 slices"      'select number of slices to be scanned
```

```
              COLOR 7
              LOCATE 4, 50
              PRINT SPACES(29);
              LOCATE 4, 50
              INPUT "", slc$
              slc = ABS(INT(VAL(slc$)))
              IF slc > 0 AND slc <= max.slices THEN    'check if user value fits in correct range
                  slice = slc
              ELSEIF slc$ <> "" THEN                    'check if return was pressed
                  BEEP
              END IF CASE 2
              LOCATE 22
              COLOR 15
              PRINT TAB(12); "select number of points to be scanned along a slice (0-"; LTRIM$(STR$(max.number)); ") ";
              COLOR 7
              LOCATE 5, 50
              PRINT SPACES(29);
              LOCATE 5, 50                              'select number of points to be scanned
              INPUT "", num$
              num = ABS(INT(VAL(num$)))
              IF num > 0 AND num <= max.number THEN     'check if user value fits in correct range
                  step.interval = CINT(tran.rev * length / (screw.rev * num))   'finds the closest integer step size for this number of points
                  dist.interval = step.interval * screw.rev / tran.rev          'finds the corresponding distance in mm for this step size
                  num = INT(tran.rev * length / (step.interval * screw.rev))   'recalculates the actual number of points that will be sampled
                  IF num <= max.number THEN number = num
              ELSEIF num$ <> "" THEN                    'check if return was pressed
                  BEEP
              END IF CASE 3
              LOCATE 22
              COLOR 15
              PRINT TAB(10); "enter the distance ("; LTRIM$(STR$(INT(100 * screw.rev / tran.rev) / 100)); "-"; LTRIM$(STR$(length)); " mm) between scanned points"
              COLOR 7
              LOCATE 6, 50
              PRINT SPACES(29);
              LOCATE 6, 50                              'select distance between scanned points
              INPUT "", sep.dis$
              sep.dis = ABS(VAL(sep.dis$))
              step.intv = INT(tran.rev * sep.dis / screw.rev)   'finds the closest integer step size to this seperation distance
              IF step.intv > 0 AND sep.dis <= length THEN       'check if user value fits in correct range
                  dist.intv = step.intv * screw.rev / tran.rev  'recalculates the actual separation distance in mm
                  num = INT(tran.rev * length / (step.intv * screw.rev))   'finds the number of points to be sampled
                  IF num > 0 AND num <= max.number THEN         'if # of points fits in the acceptable range, the values are set
                      step.interval = step.intv
                      dist.interval = dist.intv
                      number = num
                  ELSE
                      BEEP
                  END IF
```

```
        ELSEIF sep.dis$ <> "" THEN                              'check if return was pressed
            BEEP
        END IF CASE 4
                                                'choose type of tube
        LOCATE 21
        COLOR 15
        PRINT TAB(21); "select the type of tube to be scanned:"
        PRINT TAB(20); "A)luminum, S)tainless Steel, or O)ther ";
        COLOR 7
        DO
            LOCATE 22, 60
            tb$ = UCASE$(INPUT$(1))
            PRINT tb$
            exit$ = "y"
            SELECT CASE tb$
                CASE "A"
                    type.tube$ = "Aluminum"
                    length = alum.length
                    scan.start = alum.start
                    scan.end = alum.end
                    number = INT(tran.rev * length / (step.interval * screw.rev))         'recalculates the actual # of pts that will be sampled
                    IF number > max.number THEN                                            'if # of pts exceeds max allowed, find the step
                        interval = tran.rev * length / (screw.rev * max.number)            ' interval for the max. number of points
                        IF interval = INT(interval) THEN
                            step.interval = INT(interval)
                        ELSE
                            step.interval = INT(interval) + 1                              'if step interval isn't an int, add 1 step to it's int value
                        END IF
                        number = INT(tran.rev * length / (step.interval * screw.rev))     'recalc the actual # of pts to be scanned
                    END IF
                    dist.interval = step.interval * screw.rev / tran.rev                  'finds the corresponding dist in mm for this step size
                CASE "S"
                    type.tube$ = "Stainless Steel"
                    length = steel.length
                    scan.start = steel.start
                    scan.end = steel.end
                    number = INT(tran.rev * length / (step.interval * screw.rev))         'recalc the actual # of pts that will be sampled
                    IF number > max.number THEN                                            'if # of pts exceeds max allowed, find the step
                        interval = tran.rev * length / (screw.rev * max.number)            ' interval for the max. number of points
                        IF interval = INT(interval) THEN
                            step.interval = INT(interval)
                        ELSE
                            step.interval = INT(interval) + 1                              'if the step interval isn't an int, add 1 step to it's int value
                        END IF
                        number = INT(tran.rev * length / (step.interval * screw.rev))     'recalc the actual # of pts to be scanned
                    END IF
                    dist.interval = step.interval * screw.rev / tran.rev                  'finds the corresponding distance in mm for this step size
                CASE "O"
                    LOCATE 7, 50
```

```
                    PRINT SPACES(29);
                    LOCATE 7, 50
                    INPUT typ.tub$
                    IF typ.tub$ <> "" THEN type.tube$ = typ.tub$    'check if return was pressed
                CASE CHR$(13)
                CASE ELSE
                    exit$ = "n"
            END SELECT
        LOOP UNTIL exit$ = "y"

CASE 5
        LOCATE 22
        COLOR 15
        PRINT TAB(9); "enter the path and basename (up to 6 char.) for the tube data"
        COLOR 7
        LOCATE 9, 40
        PRINT SPACES(39);
        LOCATE 9, 40
        INPUT "", bs$
        bs$ = UCASE$(bs$)
        IF LEN(bs$) > 0 THEN
            check$ = "y"
            CALL check.name.path(check$, bs$, bs.nm$, bs.pt$)       'enter a base path and name to save all data
            IF check$ = "n" THEN                                    'check to make sure file format is correct
                BEEP                                                'if not, beep
            ELSE                                                    'otherwise set file names
                base.path$ = bs.pt$
                base.name$ = bs.nm$
                tube.path$ = bs.pt$
                tube.name$ = bs.nm$
                peak.path$ = bs.pt$
                peak.name$ = bs.nm$
                spline.path$ = bs.pt$
                spline.name$ = bs.nm$
                volume.path$ = bs.pt$
                volume.name$ = bs.nm$
                config.path$ = bs.pt$
                config.name$ = bs.nm$
            END IF
        END IF
        exit$ = "n"
        DO
            LOCATE 21, 1
            COLOR 15
            PRINT "D)isplay T)ube P)eak S)pline V)olume C)onfiguration or A)ll files? ";  'display directory of disk
            COLOR 7
            which$ = UCASE$(INPUT$(1))
            PRINT which$
            exit$ = "y"
            okay$ = "y"
            SELECT CASE which$
```

```
CASE "T"
    CLS
    PRINT "Directory Path = "; UCASE$(tube.path$)
    PRINT "Current Path = ";
    FILES tube.path$ + "*" + tube.exten$
    IF okay$ = "n" THEN
        PRINT
        PRINT "There are no tube files with the "; tube.exten$; " extension in this directory"
        PRINT
    END IF
    PRINT "press any key to continue"
    x$ = INPUT$(1)
CASE "P"
    CLS
    PRINT "Directory Path = "; UCASE$(tube.path$)
    PRINT "Current Path = ";
    FILES peak.path$ + "*" + peak.exten$
    IF okay$ = "n" THEN
        PRINT
        PRINT "There are no peak files with the "; peak.exten$; " extension in this directory"
        PRINT
    END IF
    PRINT "press any key to continue"
    x$ = INPUT$(1)
CASE "S"
    CLS
    PRINT "Directory Path = "; UCASE$(spline.path$)
    PRINT "Current Path = ";
    FILES spline.path$ + "*" + spline.exten$
    IF okay$ = "n" THEN
        PRINT
        PRINT "There are no spline fit files with the "; spline.exten$; " extension in this directory"
        PRINT
    END IF
    PRINT "press any key to continue"
    x$ = INPUT$(1)
CASE "V"
    CLS
    PRINT "Directory Path = "; UCASE$(tube.path$)
    PRINT "Current Path = ";
    FILES volume.path$ + "*" + volume.exten$
    IF okay$ = "n" THEN
        PRINT
        PRINT "There are no volume profile files with the "; volume.exten$; " extension in this directory"
        PRINT
    END IF
    PRINT "press any key to continue"
    x$ = INPUT$(1)
CASE "C"
    CLS
    PRINT "Directory Path = "; UCASE$(par.path$)
```

```
                        PRINT "Current Path = ";
                        FILES config.path$ + "*" + config.exten$
                        IF okay$ = "n" THEN
                            PRINT
                            PRINT "There are no parameter files with the "; config.exten$; " extension in this directory"
                            PRINT
                        END IF
                        PRINT "press any key to continue"
                        x$ = INPUT$(1)
                CASE "A"
                        INPUT "Enter path of directory:  "; path$
                        IF path$ <> "" THEN
                            IF RIGHT$(path$, 1) <> "\" THEN path$ = path$ + "\"
                            CLS
                            PRINT "Directory Path = "; UCASE$(path$)
                            PRINT "Current Path = ";
                            FILES path$
                            IF okay$ = "n" THEN
                                PRINT
                                PRINT "There are no files in this directory"
                                PRINT
                            END IF
                            PRINT "press any key to continue"
                            x$ = INPUT$(1)
                        END IF
                CASE CHR$(13)
                CASE ELSE
                        exit$ = "n"
            END SELECT
            okay$ = "y"
        LOOP UNTIL exit$ = "y"
        exit$ = "n"
    CASE 7                                                  'delete selected files
        DO
            LOCATE 21
            COLOR 15
            PRINT TAB(14); "delete the selected name of which type of data files"
            PRINT TAB(10); "T)ube  P)eak  S)pline  V)olume  C)onfiguration  A)ll  or  E)xit:  ";
            COLOR 7
            which$ = UCASE$(INPUT$(1))
            PRINT which$
            exit$ = "y"
            SELECT CASE which$
                CASE "T"
                    PRINT TAB(30); "Are you sure (y/n): ";
                    sure$ = UCASE$(INPUT$(1))
                    PRINT sure$
                    IF sure$ = "y" THEN KILL tube.path$ + tube.name$ + "??" + tube.exten$
                CASE "P"
                    PRINT TAB(30); "Are you sure (y/n): ";
                    sure$ = UCASE$(INPUT$(1))
```

```
              PRINT sure$
              IF sure$ = "Y" THEN KILL peak.path$ + peak.name$ + "?" + peak.exten$
        CASE "S"
              PRINT TAB(30); "Are you sure (y/n): ";
              sure$ = UCASE$(INPUT$(1))
              PRINT sure$
              IF sure$ = "Y" THEN KILL spline.path$ + spline.name$ + "?" + spline.exten$
        CASE "V"
              PRINT TAB(30); "Are you sure (y/n): ";
              sure$ = UCASE$(INPUT$(1))
              PRINT sure$
              IF sure$ = "Y" THEN KILL volume.path$ + volume.name$ + volume.exten$
        CASE "C"
              PRINT TAB(30); "Are you sure (y/n): ";
              sure$ = UCASE$(INPUT$(1))
              PRINT sure$
              IF sure$ = "Y" THEN KILL config.path$ + config.name$ + config.exten$
        CASE "A"
              PRINT TAB(30); "Are you sure (y/n): ";
              sure$ = UCASE$(INPUT$(1))
              PRINT sure$
              IF sure$ = "Y" THEN
                    KILL tube.path$ + tube.name$ + "*.tub"
                    KILL peak.path$ + peak.name$ + "*.pk"
                    KILL spline.path$ + spline.name$ + "*.spl"
                    KILL volume.path$ + volume.name$ + "*.vol"
                    KILL config.path$ + config.name$ + "*.con"
              END IF
        CASE "E"
        CASE CHR$(13)
        CASE ELSE
              exit$ = "n"
      END SELECT
LOOP UNTIL exit$ = "y"
      exit$ = "n"
END SELECT
GOSUB main.menu.on
GOSUB main.menu
RETURN '------------------ configuration menu ----------------------
'------------------------------------------------------------
config:
    current.menu$ = "config"           'set current menu to config
    GOSUB keys.off                     'turn off key trapping
    GOSUB config.menu.init             'initalize config key trapping
    GOSUB config.menu.on               'turn on key trapping
    GOSUB config.menu                  'display config menu
RETURN
```

```
config.menu.init:
    KEY 15, CHR$(160) + CHR$(72)            'up--up
    KEY 16, CHR$(160) + CHR$(75)            'left--up
    KEY 17, CHR$(160) + CHR$(77)            'right-down
    KEY 18, CHR$(160) + CHR$(80)            'down--down
    KEY 19, CHR$(32) + CHR$(31)             'S--save defaults
    KEY 20, CHR$(32) + CHR$(28)             'RET-change
    KEY 21, CHR$(32) + CHR$(38)             'L--load defaults
    KEY 25, CHR$(32) + CHR$(1)              'ESC-quit ON KEY(1) GOSUB main                    'F1--goto main menu
    ON KEY(3) GOSUB printing                'F3--goto print menu
    ON KEY(4) GOSUB disk                    'F4--goto disk/hardware menu
    ON KEY(11) GOSUB c.up                   'up(cursor)--move up one menu item
    ON KEY(12) GOSUB c.up                   'left(cursor)--move up one menu item
    ON KEY(15) GOSUB c.up                   'up(keypad)--move up one menu item
    ON KEY(16) GOSUB c.up                   'left(keypad)--move up one menu item
    ON KEY(13) GOSUB c.down                 'right(cursor)--move down one menu item
    ON KEY(14) GOSUB c.down                 'down(cursor)--move down one menu item
    ON KEY(17) GOSUB c.down                 'right(keypad)--move down one menu item
    ON KEY(18) GOSUB c.down                 'down(keypad)--move down one menu item
    ON KEY(19) GOSUB save.tube.def          'S--save configurations
    ON KEY(20) GOSUB c.change               'RET--select menu item
    ON KEY(21) GOSUB load.tube.def          'L--load configuration file
    ON KEY(25) GOSUB c.quit                 'ESC-quit program FOR x = 1 TO 23
        menu.color(x) = 7                   'deselect menu items (low intensity white)
    NEXT x
    menu.color(1) = 15                      'hilight 1st menu item (high intensity white)
    menu.pos = 1                            'set position to 1st menu item
RETURN config.menu.on:
    FOR x = 11 TO 21
        KEY(x) ON
    NEXT x
    KEY(1) ON
    KEY(3) ON
    KEY(4) ON
    KEY(25) ON                              'turn key trapping on
RETURN config.menu:
    CLS                                     'display config menu
    PRINT TAB(22); "Software/Hardware Configuration Menu"
    PRINT "---------------------------------------------------------------"
    PRINT
    COLOR menu.color(1): PRINT TAB(10); "Scanning Distance";
    COLOR menu.color(16): PRINT TAB(45); "start ";
```

```
COLOR 7: PRINT scan.start; " mm";
COLOR menu.color(17): PRINT TAB(65); "end ";
COLOR 7: PRINT scan.end; " mm"
PRINT TAB(15); "Length of Scan: "; length; " mm"
PRINT TAB(51); "translator"; TAB(67); "rotator"
COLOR menu.color(2): PRINT TAB(10); "Motor Port";
COLOR 7: PRINT TAB(30); motor.port$; TAB(55); translator; TAB(69); rotator
COLOR menu.color(3): PRINT TAB(10); "Motor Speed";
COLOR menu.color(18): PRINT TAB(55); tran.speed;
COLOR menu.color(19): PRINT TAB(69); rot.speed
COLOR menu.color(4): PRINT TAB(10); "Number of Steps per Revol.";
COLOR menu.color(20): PRINT TAB(55); tran.rev;
COLOR menu.color(21): PRINT TAB(69); rot.rev
COLOR menu.color(5): PRINT TAB(10); "Trans. Distance of One Screw Revol.";
COLOR 7: PRINT TAB(60); screw.rev; " mm"
COLOR menu.color(6): PRINT TAB(10); "Number of Times to Sample One Point";
COLOR 7: PRINT TAB(60); sample
COLOR menu.color(7): PRINT TAB(10); "Sampling Rate";
COLOR 7: PRINT TAB(60); timer.rate; " Hz"
COLOR menu.color(8): PRINT TAB(10); "A/D Board Frequency";
COLOR 7: PRINT TAB(60); timer.freq / 1000000; " MHz"
COLOR menu.color(9): PRINT TAB(10); "Scanning Channel Limits";
COLOR menu.color(22): PRINT TAB(52); "low ";
COLOR 7: PRINT low.scan;
COLOR menu.color(23): PRINT TAB(67); "high ";
COLOR 7: PRINT high.scan
COLOR menu.color(10): PRINT TAB(10); "I/O Address";
COLOR 7: PRINT TAB(60); io.add
COLOR menu.color(11): PRINT TAB(10); "Interrupt Level";
COLOR 7: PRINT TAB(60); interrupt
COLOR menu.color(12): PRINT TAB(10); "DMA Level";
COLOR 7: PRINT TAB(60); dma.level
COLOR menu.color(13): PRINT TAB(10); "Increment of Thickness of Deposit";
COLOR 7: PRINT TAB(60); thickness; " microns"
COLOR menu.color(14): PRINT TAB(10); "Error Tolerance";
COLOR 7: PRINT TAB(60); errtol
COLOR menu.color(15): PRINT TAB(10); "Output Increment";
COLOR 7: PRINT TAB(60); incout; " mm"
COLOR 7
PRINT
PRINT TAB(10); "F1-Main Menu  F3-Print Menu  F4-Disk/Hardware Menu  ESC-Quit"
PRINT TAB(19); "L-Load Tube Defaults  S-Save Tube Defaults"
RETURN
c.quit:
IF menu.pos > 15 THEN
    menu.color(menu.pos) = 7          'exit select or program
    SELECT CASE menu.pos
        CASE 16, 17                   'if tube file has been selected, move back out to menu
            menu.pos = 1
        CASE 18, 19                   'scanning distance submenu
            menu.pos = 3              'motor speed submenu
```

```
            CASE 20, 21
                menu.pos = 4              'number of steps / revol. submenu
            CASE 22, 23
                menu.pos = 9              'scanning limits submenu
        END SELECT
        menu.color(menu.pos) = 15
        GOSUB c.down                      '???? otherwise it hi-lights the next item up
    ELSE
        GOSUB quit                        'exit program
        GOSUB config.menu.on              'otherwise turn key trapping on
        GOSUB c.down                      '???? otherwise it hi-lights the next item up
        GOSUB config.menu                 'display config menu
    END IF c.up:
    IF menu.pos = 1 THEN                                                  'move up one menu item
        menu.pos = 15                                                     'if cursor is at 1st item, move to last
        menu.color(1) = 7
    ELSEIF menu.pos > 15 AND INT(menu.pos / 2) = menu.pos / 2 THEN        'if in file select sub menu then move between choices
        menu.pos = menu.pos + 1
        menu.color(menu.pos) = 15
        menu.color(menu.pos - 1) = 7
    ELSEIF menu.pos > 15 AND INT(menu.pos / 2) <> menu.pos / 2 THEN       'if in file select sub menu then move between choices
        menu.pos = menu.pos - 1
        menu.color(menu.pos) = 15
        menu.color(menu.pos + 1) = 7
    ELSE                                                                  'otherwise, move cursor up
        menu.pos = menu.pos - 1
        menu.color(menu.pos + 1) = 7
    END IF
    menu.color(menu.pos) = 15                                             'hilight menu item
    GOSUB config.menu
RETURN c.down:
    IF menu.pos = 15 THEN                                                 'move down one menu item
        menu.pos = 1                                                      'if cursor at last item, move to 1st
        menu.color(15) = 7
    ELSEIF menu.pos > 15 AND INT(menu.pos / 2) = menu.pos / 2 THEN        'if in file select sub menu then move between choices
        menu.pos = menu.pos + 1
        menu.color(menu.pos) = 15
        menu.color(menu.pos - 1) = 7
    ELSEIF menu.pos > 15 AND INT(menu.pos / 2) <> menu.pos / 2 THEN       'if in file select sub menu then move between choices
        menu.pos = menu.pos - 1
        menu.color(menu.pos) = 15
        menu.color(menu.pos + 1) = 7
    ELSE                                                                  'otherwise move cursor down
        menu.pos = menu.pos + 1
        menu.color(menu.pos - 1) = 7
    END IF
    menu.color(menu.pos) = 15                                             'hilight menu item
```

```
        GOSUB config.menu
        RETURN c.change:
        GOSUB keys.off
        SELECT CASE menu.pos
            CASE 1                                          'select menu item
                menu.pos = 16
                menu.color(1) = 7
                menu.color(16) = 15                         'scan starting and ending points
                GOSUB config.menu                           ' move to scanning position submenu CASE 2                                          'motor port and motor configuration
                LOCATE 22
                PRINT SPACES(79); : PRINT SPACES(79);
                DO
                    COLOR 15
                    LOCATE 22
                    PRINT TAB(21); "what port are the motors attached to:"
                    PRINT TAB(21); "M)ono disp/lpt1    1) lpt1     2) lpt2       ";
                    COLOR 7
                    prt$ = UCASE$(INPUT$(1))
                    PRINT prt$;
                    exit$ = "y"
                    changed$ = "y"

SELECT CASE prt$                        'set motor port and possible motor numbers
                        CASE "M"
                                    mtr.port$ = "Mono Disp/LPT1:"
                                    motor1$ = "1"
                                    motor2$ = "2"
                        CASE "1"
                                    mtr.port$ = "LPT1:"
                                    motor1$ = "3"
                                    motor2$ = "4"
                        CASE "2"
                                    mtr.port$ = "LPT2:"
                                    motor1$ = "5"
                                    motor2$ = "6"
                        CASE CHR$(13)
                                    changed$ = "n"
                        CASE ELSE
                                    exit$ = "n"
                    END SELECT
                LOOP UNTIL exit$ = "y"

IF changed$ = "y" THEN                      'set motor configurations
                    DO
                        LOCATE 22
                        PRINT SPACES(79);
                        LOCATE 22
                        COLOR 15
```

```
                    PRINT TAB(30); "port selected: "; mtr.port$
                    PRINT TAB(11); "select tran/rot motor number config.:   1) "; motor1$; "/"; motor2$; "  or  2) "; motor2$; "/"; motor1$; " = ";
                    COLOR 7
                    motor.num$ = UCASE$(INPUT$(1))
                    PRINT motor.num$
                    exit$ = "y"

SELECT CASE motor.num$
                         CASE "1"
                              motor.port$ = mtr.port$
                              translator = VAL(motor1$)
                              rotator = VAL(motor2$)
                         CASE "2"
                              motor.port$ = mtr.port$
                              translator = VAL(motor2$)
                              rotator = VAL(motor1$)
                         CASE CHR$(13)
                         CASE ELSE
                              exit$ = "n"
               END IF
               LOOP UNTIL exit$ = "y"
          END SELECT CASE 3
          menu.pos = 18                                   'motor speed
          menu.color(3) = 7                               ' move to submenu
          menu.color(18) = 15
          GOSUB config.menu CASE 4
          menu.pos = 20                                   'number of steps for one revolution of the motor
          menu.color(4) = 7                               ' move to submenu
          menu.color(20) = 15
          GOSUB config.menu CASE 5
          LOCATE 22                                       'translational distance of one screw revolution
          PRINT SPACE$(79); : PRINT SPACE$(79);
          LOCATE 22
          COLOR 15
          PRINT TAB(7); "distance the probe translate in one full motor revolution (in mm)"
          COLOR 7
          LOCATE 10, 60
          PRINT SPACE$(19);
          LOCATE 10, 60
          INPUT "", scr.dis$
          scr.dis = ABS(VAL(scr.dis$))
          IF scr.dis > 0 THEN                             'make sure distance is greater than zero
               screw.rev = scr.dis
          ELSEIF scr.dis$ <> "" THEN
               BEEP
          END IF CASE 6
          LOCATE 22                                       'number of data points to be sampled at one point
```

```
            PRINT SPACES$(79); : PRINT SPACES$(79);
            LOCATE 22
            COLOR 15
            PRINT TAB(11); "number of data points to be sampled at one point (1-"; LTRIM$(STR$(max.sample)); ")"
            COLOR 7
            LOCATE 11, 60
            PRINT SPACES$(19);
            LOCATE 11, 60
            INPUT "", num$
            num = ABS(INT(VAL(num$)))
            IF num > 0 AND num <= max.sample THEN          'make sure number falls in correct range
                sample = num
            ELSEIF num$ <> "" THEN
                BEEP
            END IF CASE 7                                                 'sampling rate of A/D board
            LOCATE 22
            PRINT SPACES$(79); : PRINT SPACES$(79);
            exit$ = "n"
            DO
                LOCATE 22
                COLOR 15
                PRINT TAB(15); "enter sampling rate or set counter values (R/C)? ";
                COLOR 7
                which$ = UCASE$(INPUT$(1))
                PRINT which$;
                exit$ = "y"
                SELECT CASE which$
                    CASE "R"                                                        'set rate by "directly" entering rate
                        LOCATE 22
                        PRINT SPACES$(79); : PRINT SPACES$(79);
                        LOCATE 22
                        COLOR 15
                        PRINT TAB(20); "enter sampling rate ("; LTRIM$(STR$(INT(10000 * min.samp.rate) / 10000)); " -"; max.samp.rate;" Hz):";
                        COLOR 7
                        LOCATE 12, 60
                        PRINT SPACES$(19);
                        LOCATE 12, 60
                        INPUT "", rate$
                        rate = ABS(VAL(rate$))
                        IF rate >= INT(10000 * min.samp.rate) / 10000 AND rate <= max.samp.rate THEN    'make sure rate is in correct range
                            n1 = INT(SQR(timer.freq / rate))            'set one counter to the integer of this squareroot of desired rate
                            n2 = INT(timer.freq / (rate * n1))          'recalculate the other and take its integer
                            timer.rate = INT(10000 * (timer.freq / n1) / n2) / 10000    'recalculate actual sampling rate
                        ELSEIF rate$ <> "" THEN
                            BEEP
                        END IF CASE "C"                                            'set sampling rate by adjusting counter values directly
                        LOCATE 22
                        PRINT SPACES$(79); : PRINT SPACES$(79);
```

```
            LOCATE 22
            COLOR 15
            PRINT TAB(20); "enter counter 1 value (2-65535): "
            COLOR 7
            LOCATE 12, 60
            PRINT SPACE$(19);
            LOCATE 12, 60
            INPUT "1--", count.1$
            LOCATE 22
            PRINT SPACE$(79); : PRINT SPACE$(79);
            LOCATE 22
            COLOR 15
            PRINT TAB(20); "enter counter 2 value (2-65535): "
            COLOR 7
            LOCATE 12, 60
            PRINT SPACE$(19);
            LOCATE 12, 60
            INPUT "2--", count.2$
            count.1 = ABS(INT(VAL(count.1$)))
            count.2 = ABS(INT(VAL(count.2$)))
            IF count.1 > 1 AND count.2 < 65536 AND count.2 > 1 AND count.2 < 65536 THEN    'make sure they're in range
                n1 = count.1                                                                'set counter 1
                n2 = count.2                                                                'set counter 2
                timer.rate = INT(10000 * (timer.freq / n1) / n2) / 10000                    'calculate rate
            ELSEIF count.1$ <> "" OR count.2$ <> "" THEN
                BEEP
            END IF
        CASE CHR$(13)
        CASE ELSE
            exit$ = "n"
        END SELECT
    LOOP UNTIL exit$ = "y"
    exit$ = "n"

CASE 8                              'clock frequency of A/D board
        LOCATE 22
        PRINT SPACE$(79); : PRINT SPACE$(79);
        LOCATE 22
        COLOR 15
        PRINT TAB(20); "enter clock frequency of A/D board (1 or 10 MHz)"
        COLOR 7
        LOCATE 13, 60
        PRINT SPACE$(19);
        LOCATE 13, 60
        INPUT "", freq$
        freq = ABS(INT(VAL(freq$)))
        IF freq = 1 THEN                                                                    '1MHz
            timer.freq = 1000000
            timer.rate = INT(10000 * (timer.freq / n1) / n2) / 10000
            min.samp.rate = (timer.freq / 65535) / 65535                                    'sets the minimum sampling rate
            max.samp.rate = timer.freq / 4                                                  'sets the maximum sampling rate
        ELSEIF freq = 10 THEN
```

```
            timer.freq = 10000000                                          '10 MHz
            timer.rate = INT(10000 * (timer.freq / n1) / n2) / 10000       'sets sampling rate
            min.samp.rate = (timer.freq / 65535) / 65535                   'sets the minimum sampling rate
            max.samp.rate = timer.freq / 4                                 'sets the maximum sampling rate
         ELSEIF freq$ <> "" THEN
            BEEP
         END IF CASE 9
         menu.pos = 22                              'scanning limits
         menu.color(9) = 7                          ' move to submenu
         menu.color(22) = 15
         GOSUB config.menu CASE 10
         LOCATE 22                                  'I/O address for A/D board initialization
         PRINT SPACES(79); : PRINT SPACES(79);
         LOCATE 22
         COLOR 15
         PRINT TAB(16); "enter the I/O address for initialization (512-1008)"
         COLOR 7
         LOCATE 15, 60
         PRINT SPACES(19);
         LOCATE 15, 60
         INPUT "", addrs$
         addrs = ABS(INT(VAL(addrs$)))
         IF addrs > 511 AND addrs < 1009 THEN       'make sure address is in correct range
            io.add = addrs
         ELSEIF addrs$ <> "" THEN
            BEEP
         END IF CASE 11
         LOCATE 22                                  'interrupt level (2-7)
         PRINT SPACES(79); : PRINT SPACES(79);
         LOCATE 22
         COLOR 15
         PRINT TAB(30); "enter the interrupt level (2-7)"
         COLOR 7
         LOCATE 16, 60
         PRINT SPACES(19);
         LOCATE 16, 60
         INPUT "", int.lvl$
         int.lvl = ABS(INT(VAL(int.lvl$)))
         IF int.lvl > 1 AND int.lvl < 8 THEN        'make sure level is between 2-7
            interrupt = int.lvl
         ELSEIF int.lvl$ <> "" THEN
            BEEP
         END IF CASE 12
         LOCATE 22                                  'DMA level (1 or 3)
         PRINT SPACES(79); : PRINT SPACES(79);
         LOCATE 22
         COLOR 15
```

```
           PRINT TAB(30); "Enter the DMA Level (1 or 3)"
           COLOR 7
           LOCATE 17, 60
           PRINT SPACES(19);
           LOCATE 17, 60
           dma.lvl$ = INPUT$(1)
           dma.lvl = ABS(INT(VAL(dma.lvl$)))
           IF dma.lvl = 1 OR dma.lvl = 3 THEN        'make sure level is 1 or 3
                 dma.level = dma.lvl
           ELSEIF dma.lvl$ <> "" THEN
                 BEEP
           END IF CASE 13
           LOCATE 22
           PRINT SPACES(79); : PRINT SPACES(79);
           LOCATE 22
           COLOR 15
           PRINT TAB(15); "enter thickness increment of each peak in microns"
           COLOR 7
           LOCATE 18, 60
           PRINT SPACES(19);
           LOCATE 18, 60
           INPUT "", thck$
           thck = ABS(VAL(thck$))
           IF thck > 0 THEN                          'each peak corresponds to an increase in thickness of this amount
                 thickness = thck
           ELSEIF thck$ <> "" THEN                   'make sure thickness increment is greater than zero
                 BEEP
           END IF CASE 14
           LOCATE 22
           PRINT SPACES(79); : PRINT SPACES(79);
           LOCATE 22
           COLOR 15
           PRINT TAB(20); "enter error tolerance for cubic spline fit of data"
           COLOR 7
           LOCATE 19, 60
           PRINT SPACES(19);
           LOCATE 19, 60
           INPUT "", ertl$
           ertl = ABS(VAL(ertl$))
           IF ertl$ = "0" OR ertl > 0 THEN           'make sure error tolerance isn't negative
                 errtol = ertl                       'error tolerance of cubic spline fit
           ELSEIF ertl$ <> "" THEN
                 BEEP
           END IF CASE 15
           LOCATE 22
           PRINT SPACES(79); : PRINT SPACES(79);    'increment of spline output
           LOCATE 22
           COLOR 15
```

```
        PRINT TAB(10); "enter the spacing between the points the spline fit generates"
        COLOR 7
        LOCATE 20, 60
        PRINT SPACES(19);
        LOCATE 20, 60
        INPUT "", inco$
        inco = ABS(VAL(inco$))                          'make sure increment is greater than zero
        IF inco > 0 THEN
            incout = inco
        ELSEIF inco$ <> "" THEN
            BEEP
        END IF CASE 16                                                 'starting position of probe from origin
        LOCATE 22
        PRINT SPACES(79); : PRINT SPACES(79);
        LOCATE 22
        COLOR 15
        PRINT TAB(12); "the starting position (in mm) of the probe to take data"
        COLOR 7
        LOCATE 4, 51
        PRINT SPACES(13);
        LOCATE 4, 51
        INPUT "", srt$
        srt = ABS(VAL(srt$))
        IF (srt > 0 AND srt < scan.end) OR srt$ = "0" THEN    'check if user value fits in correct range
            scan.start = srt
            length = scan.end - scan.start
            number = INT(tran.rev * length / (step.interval * screw.rev))  'recalc the actual number of points that will be sampled
            IF number > max.number THEN                 'if # of pts > max allowed, find step intvl for the max. # of pts
                interval = tran.rev * length / (screw.rev * max.number)
                IF interval = INT(interval) THEN
                    step.interval = INT(interval)
                ELSE
                    step.interval = INT(interval) + 1   'if the step interval is not an integer, add one step to it's integer value
                END IF
                number = INT(tran.rev * length / (step.interval * screw.rev))  'recalculate the actual number of points to be scanned
            END IF
            dist.interval = step.interval * screw.rev / tran.rev           'finds the corresponding dist in mm for this step size
            menu.color(menu.pos) = 7
            menu.pos = 1
            menu.color(1) = 15
        ELSEIF srt$ <> "" THEN                          'check if return was pressed
            BEEP
        END IF CASE 17                                                 'ending position of probe
        LOCATE 22
        PRINT SPACES(79); : PRINT SPACES(79);
        LOCATE 22
        COLOR 15
        PRINT TAB(13); "the ending position (in mm) of the probe to take data"
        COLOR 7
```

```
            LOCATE 4, 69
            PRINT SPACES(10);
            LOCATE 4, 69
            INPUT "", s.end$
            s.end = ABS(VAL(s.end$))
            IF s.end > 0 AND s.end > scan.start THEN                    'check if user value fits in correct range
                scan.end = s.end
                length = scan.end - scan.start
                number = INT(tran.rev * length / (step.interval * screw.rev))
                IF number > max.number THEN                             'recalc the actual # of pts that will be sampled
                    interval = tran.rev * length / (screw.rev * max.number)   'if # of pts > max allowed, find the step intvl for max. # of pts
                    IF interval = INT(interval) THEN
                        step.interval = INT(interval)
                    ELSE
                        step.interval = INT(interval) + 1               'if the step interval is not an int, add one step to it's int value
                    END IF
                    number = INT(tran.rev * length / (step.interval * screw.rev))   'recalculate the actual number of points to be scanned
                END IF
                dist.interval = step.interval * screw.rev / tran.rev    'finds the corresponding distance in mm for this step size
                menu.color(menu.pos) = 7
                menu.pos = 1
                menu.color(1) = 15
            ELSEIF srt$ <> "" THEN                                      'check if return was pressed
                BEEP
            END IF CASE 18                                                             'translating motor speed
            LOCATE 22
            PRINT SPACES(79); : PRINT SPACES(79);
            LOCATE 22
            COLOR 15
            PRINT TAB(11); "set new translating motor speed (0-32000  fastest-slowest)"
            COLOR 7
            LOCATE 8, 55
            PRINT SPACES(13);
            LOCATE 8, 55
            INPUT "", spd$
            spd = ABS(INT(VAL(spd$)))
            IF spd$ = "0" OR (spd > 0 AND spd <= 32000) THEN            'make sure speed is in correct range
                tran.speed = spd
                menu.color(menu.pos) = 7
                menu.pos = 3
                menu.color(3) = 15
            ELSEIF spd$ <> "" THEN
                BEEP
            END IF CASE 19                                                             'rotating motor speed
            LOCATE 22
            PRINT SPACES(79); : PRINT SPACES(79);
            LOCATE 22
            COLOR 15
            PRINT TAB(13); "set new rotating motor speed (0-32000  fastest-slowest)"
```

```
            COLOR 7
            LOCATE 8, 69
            PRINT SPACES(10);
            LOCATE 8, 69
            INPUT "", spd$
            spd = ABS(INT(VAL(spd$)))
            IF spd$ = "0" OR (spd > 0 AND spd <= 32000) THEN       'make sure speed is in correct range
                rot.speed = spd
                menu.color(menu.pos) = 7
                menu.pos = 3
                menu.color(3) = 15
            ELSEIF spd$ <> "" THEN
                BEEP
            END IF CASE 20
            LOCATE 22
            PRINT SPACES(79); : PRINT SPACES(79);
            LOCATE 22
            COLOR 15
            PRINT TAB(12); "number of steps per revolution of the translating motor"
            COLOR 7
            LOCATE 9, 55
            PRINT SPACES(13);
            LOCATE 9, 55
            INPUT "", stp$
            stp = ABS(INT(VAL(stp$)))
            IF stp > 0 THEN                               'number of steps per revolution for translating motor
                tran.rev = stp
                menu.color(menu.pos) = 7
                menu.pos = 4
                menu.color(4) = 15
            ELSEIF stp$ <> "" THEN
                BEEP
            END IF CASE 21
            LOCATE 22
            PRINT SPACES(79); : PRINT SPACES(79);
            LOCATE 22
            COLOR 15
            PRINT TAB(14); "number of steps per revolution of the rotating motor"
            COLOR 7
            LOCATE 9, 69
            PRINT SPACES(10);
            LOCATE 9, 69
            INPUT "", stp$
            stp = ABS(INT(VAL(stp$)))
            IF stp > 0 THEN                               'make sure number is greater than zero
                rot.rev = stp
                menu.color(menu.pos) = 7
                menu.pos = 4
                menu.color(4) = 15
```

```
            ELSEIF stp$ <> "" THEN
                BEEP
            END IF

CASE 22                                                 'low scan limit on A/D board (0-15)
        LOCATE 22
        PRINT SPACES(79); : PRINT SPACES(79);
        LOCATE 22
        COLOR 15
        PRINT TAB(11); "enter the lower scan probe number (0-15) of the A/D board"
        COLOR 7
        LOCATE 14, 56
        PRINT SPACES(10);
        LOCATE 14, 56
        INPUT "", low$
        low = ABS(INT(VAL(low$)))
        IF (low$ = "0") OR ((low > 0 AND low < 16) THEN    'make sure limit is between 0-15
            low.scan = low
            menu.color(menu.pos) = 7
            menu.pos = 9
            menu.color(9) = 15
        ELSEIF low$ <> "" THEN
            BEEP
        END IF CASE 23                                                 'low scan limit on A/D board (0-15)
        LOCATE 22
        PRINT SPACES(79); : PRINT SPACES(79);
        LOCATE 22
        COLOR 15
        PRINT TAB(11); "enter the higher scan probe number (0-15) of the A/D board"
        COLOR 7
        LOCATE 14, 72
        PRINT SPACES(7);
        LOCATE 14, 72
        INPUT "", high$
        high = ABS(INT(VAL(high$)))
        IF (high$ = "0") OR (high > 0 AND high < 16) THEN  'make sure limit is between 0-15
            high.scan = high
            menu.color(menu.pos) = 7
            menu.pos = 9
            menu.color(9) = 15
        ELSEIF high$ <> "" THEN
            BEEP
        END IF END SELECT
    GOSUB config.menu.on
    GOSUB config.menu
RETURN save.tube.def:
    GOSUB keys.off
    OPEN config.path$ + config.name$ + config.exten$ FOR OUTPUT AS #1    'save configuration in selected .CON file
```

```
         IF path.quit$ = "y" THEN          'if path is incorrect, return to menu
            path.quit$ = "n"
            BEEP
            CLS
            LOCATE 12
            PRINT TAB(22); "Invalid Path Specified for Data File"
            PRINT
            PRINT TAB(22); "press any key to return to the menu"
            zz$ = INPUT$(1)
            GOSUB config.menu.on
            GOSUB config.menu
            RETURN
         END IF
         PRINT #1, tube.paths
         PRINT #1, tube.name$
         PRINT #1, save.tube$
         PRINT #1, peak.paths
         PRINT #1, peak.name$
         PRINT #1, save.peak$
         PRINT #1, spline.path$
         PRINT #1, spline.name$
         PRINT #1, save.spline$
         PRINT #1, volume.path$
         PRINT #1, volume.name$
         PRINT #1, save.volume$
         PRINT #1, config.path$
         PRINT #1, config.name$
         PRINT #1, save.config$
         PRINT #1, slice
         PRINT #1, number
         PRINT #1, dist.interval
         PRINT #1, step.interval
         PRINT #1, type.tubes
         PRINT #1, scan.start
         PRINT #1, scan.end
         PRINT #1, length
         PRINT #1, motor.ports
         PRINT #1, translator
         PRINT #1, rotator
         PRINT #1, tran.speed
         PRINT #1, rot.speed
         PRINT #1, tran.rev
         PRINT #1, rot.rev
         PRINT #1, screw.rev
         PRINT #1, sample
         PRINT #1, timer.rate
         PRINT #1, n1
         PRINT #1, n2
         PRINT #1, timer.freq
         PRINT #1, low.scan
         PRINT #1, high.scan
```

```
PRINT #1, io.add
PRINT #1, interrupt
PRINT #1, dma.level
PRINT #1, thickness
PRINT #1, errtol
PRINT #1, incout
PRINT #1, max.pk.wid
PRINT #1, min.pk.wid
PRINT #1, pos.thresh
PRINT #1, neg.thresh
PRINT #1, max.consec
PRINT #1, min.plateau
PRINT #1, move.average
PRINT #1, find.peaks
PRINT #1, printer.port$
PRINT #1, scrtype$
PRINT #1, key.break$
PRINT #1, "Version"; program.version
PRINT #1, DATE$
PRINT #1, scr
IF config.name$ = "DEF" THEN                            'if user saves on DEF.CON then change tube defaults
    IF type.tube$ = "Aluminum" THEN                     'if the current tube is aluminum, change its defaults
        PRINT #1, scan.start
        PRINT #1, scan.end
        PRINT #1, length
        PRINT #1, steel.start
        PRINT #1, steel.end
        PRINT #1, steel.length
    ELSEIF type.tube$ = "Stainless Steel" THEN          'if the current tube is steel, change its defaults
        PRINT #1, alum.start
        PRINT #1, alum.end
        PRINT #1, alum.length
        PRINT #1, scan.start
        PRINT #1, scan.end
        PRINT #1, length
    ELSE                                                'if the current tube is an other, don't change defaults
        PRINT #1, alum.start
        PRINT #1, alum.end
        PRINT #1, alum.length
        PRINT #1, steel.start
        PRINT #1, steel.end
        PRINT #1, steel.length
    END IF
ELSE                                                    'if the config file is not DEF.CON, save old defaults
    PRINT #1, alum.start
    PRINT #1, alum.end
    PRINT #1, alum.length
    PRINT #1, steel.start
    PRINT #1, steel.end
    PRINT #1, steel.length
END IF
```

```
              PRINT #1, base.path$
              PRINT #1, base.name$
       CLOSE #1
       GOSUB config.menu.on
       GOSUB config.menu
RETURN load.tube.def:
       GOSUB keys.off
       OPEN config.path$ + config.name$ + config.exten$ FOR INPUT AS #1    'load configuration from selected .CON file
              IF path.quit$ = "y" THEN                                      'if path is incorrect, return to menu
                     path.quit$ = "n"
                     BEEP
                     CLS
                     LOCATE 12
                     PRINT TAB(22); "Invalid Path Specified for Data File"
                     PRINT
                     PRINT TAB(22); "press any key to return to the menu"
                     zz$ = INPUT$(1)
                     GOSUB config.menu.on
                     GOSUB config.menu
                     RETURN
              END IF INPUT #1, tube.path$
              INPUT #1, tube.name$
              INPUT #1, save.tube$
              INPUT #1, peak.path$
              INPUT #1, peak.name$
              INPUT #1, save.peak$
              INPUT #1, spline.path$
              INPUT #1, spline.name$
              INPUT #1, save.spline$
              INPUT #1, volume.path$
              INPUT #1, volume.name$
              INPUT #1, save.volume$
              INPUT #1, config.path$
              INPUT #1, config.name$
              INPUT #1, save.config$
              INPUT #1, slice
              INPUT #1, number
              INPUT #1, dist.interval
              INPUT #1, step.interval
              INPUT #1, type.tube$
              INPUT #1, scan.start
              INPUT #1, scan.end
              INPUT #1, length
              INPUT #1, motor.port$
              INPUT #1, translator
              INPUT #1, rotator
```

```
INPUT #1, tran.speed
INPUT #1, rot.speed
INPUT #1, tran.rev
INPUT #1, rot.rev
INPUT #1, screw.rev
INPUT #1, sample
INPUT #1, timer.rate
INPUT #1, n1
INPUT #1, n2
INPUT #1, timer.freq
INPUT #1, low.scan
INPUT #1, high.scan
INPUT #1, io.add
INPUT #1, interrupt
INPUT #1, dma.level
INPUT #1, thickness
INPUT #1, errtol
INPUT #1, incout
INPUT #1, max.pk.wid
INPUT #1, min.pk.wid
INPUT #1, pos.thresh
INPUT #1, neg.thresh
INPUT #1, max.consec
INPUT #1, min.plateau
INPUT #1, move.average
INPUT #1, find.peak$
INPUT #1, printer.port$
INPUT #1, scrtype$
INPUT #1, key.break$
INPUT #1, file.version$
INPUT #1, file.date$
INPUT #1, scr
INPUT #1, alum.start
INPUT #1, alum.end
INPUT #1, alum.length
INPUT #1, steel.start
INPUT #1, steel.end
INPUT #1, steel.length
INPUT #1, base.path$
INPUT #1, base.name$
CLOSE #1 min.samp.rate = (timer.freq / 65535) / 65535
max.samp.rate = timer.freq / 4

SELECT CASE scrtype$
    CASE "Mono"
        scr = 2                          'set screen mode to 2 - Monochrome
        yaxismin = 13                    'set minimum y position for graphical display
        yaxismax = 169                   'set maximum y position for graphical display
        ticky = 188                      'sets y position of tick mark below x-axis
```

'sets the minimum sampling rate
'sets the maximum sampling rate

```
                    marky = 193                  'sets y position of marked peaks
              CASE "Hi-Res Color"
                    scr = 9                      'set screen mode to 9 - Color
                    yaxismin = 30                'set minimum y position for graphical display
                    yaxismax = 296               'set maximum y position for graphical display
                    ticky = 333                  'sets y position of tick mark below x-axis
                    marky = 340                  'sets y position of marked peaks
         END SELECT
         CLOSE #1
         GOSUB config.menu.on
         GOSUB config.menu
RETURN
'---------------- printing menu ----------------
'----------------------------------------------- disk:
         current.menu$ = "disk"                  'set current menu to disk menu
         GOSUB keys.off                          'turn off key trapping
         GOSUB disk.menu.init                    'initialize disk menu key trapping
         GOSUB disk.menu.on                      'turn on key trapping
         GOSUB disk.menu                         'display disk menu
RETURN disk.menu.init:                                  'initialize disk menu key trapping KEY 15, CHR$(160) + CHR$(72)            'up--up
         KEY 16, CHR$(160) + CHR$(75)            'left--up
         KEY 17, CHR$(160) + CHR$(77)            'right--down
         KEY 18, CHR$(160) + CHR$(80)            'down--down
         KEY 19, CHR$(32) + CHR$(28)             'RET--change
         KEY 25, CHR$(32) + CHR$(1)              'ESC-quit ON KEY(1) GOSUB main                    'F1--goto main menu
         ON KEY(2) GOSUB config                  'F2--goto config menu
         ON KEY(3) GOSUB printing                'F3--goto print menu
         ON KEY(11) GOSUB d.up                   'up(cursor)--move up one menu item
         ON KEY(12) GOSUB d.up                   'left(cursor)--move up one menu item
         ON KEY(15) GOSUB d.up                   'up(keypad)--move up one menu item
         ON KEY(16) GOSUB d.up                   'left(keypad)--move up one menu item
         ON KEY(13) GOSUB d.down                 'right(cursor)--move down one menu item
         ON KEY(14) GOSUB d.down                 'down(cursor)--move down one menu item
         ON KEY(17) GOSUB d.down                 'right(keypad)--move down one menu item
         ON KEY(18) GOSUB d.down                 'down(keypad)--move down one menu item
         ON KEY(19) GOSUB d.change               'RET--select menu item
         ON KEY(25) GOSUB d.quit                 'ESC--exit program FOR x = 1 TO 19
             menu.color(x) = 7                   'deselect menu items (low intensity white)
         NEXT x
         menu.color(1) = 15                      'hilight 1st menu item (high intensity white)
         menu.pos = 1                            'move cursor to 1st menu item
```

```
        RETURN disk.menu.on:
        FOR x = 11 TO 19                                        'turn key trapping on
            KEY(x) ON NEXT x
        KEY(1) ON
        KEY(2) ON
        KEY(3) ON
        KEY(25) ON
        RETURN disk.menu:
        CLS                                                     'display disk/hardware menu
        PRINT TAB(20); "Data File and Computer Configuration Menu"
        PRINT "-----------------------------------------------------------------------------"
        PRINT
        COLOR menu.color(1): PRINT TAB(5); "Computer Screen Type";
        COLOR 7: PRINT TAB(60); scrtype$
        PRINT
        PRINT TAB(40); "name/path"; TAB(68); "save file?"
        COLOR menu.color(2): PRINT TAB(5); "Scanned Tube Data";
        COLOR menu.color(10): PRINT TAB(30); tube.path$ + tube.name$ + "*" + tube.exten$;
        COLOR menu.color(11): PRINT TAB(72); save.tube$
        COLOR menu.color(3): PRINT TAB(5); "Marked Peaks Data";
        COLOR menu.color(12): PRINT TAB(30); peak.path$ + peak.name$ + "*" + peak.exten$;
        COLOR menu.color(13): PRINT TAB(72); save.peak$
        COLOR menu.color(4): PRINT TAB(5); "Spline Fit Data";
        COLOR menu.color(14): PRINT TAB(30); spline.path$ + spline.name$ + "*" + spline.exten$;
        COLOR menu.color(15): PRINT TAB(72); save.spline$
        COLOR menu.color(5): PRINT TAB(5); "Volume Report";
        COLOR menu.color(16): PRINT TAB(30); volume.path$ + volume.name$ + volume.exten$;
        COLOR menu.color(17): PRINT TAB(72); save.volume$
        COLOR menu.color(6): PRINT TAB(5); "Configurations";
        COLOR menu.color(18): PRINT TAB(30); config.path$ + config.name$ + config.exten$;
        COLOR menu.color(19): PRINT TAB(72); save.config$
        PRINT
        COLOR menu.color(7): PRINT TAB(5); "Change All Data File Locations"
        COLOR menu.color(8): PRINT TAB(5); "Disk Directory"
        COLOR menu.color(9): PRINT TAB(5); "Clear All Data Files With Current Locations"
        COLOR 7
        PRINT
        PRINT
        PRINT TAB(10); "F1-Main Menu    F2-Configuration Menu    F3-Print Menu    ESC-Quit"
        RETURN d.quit: IF menu.pos > 9 THEN                                    'if in a sub menu, return to disk menu
            menu.color(menu.pos) = 7
            SELECT CASE menu.pos
                CASE 10, 11                                     'scanned tube submenu
```

```
            CASE 12, 13
                menu.pos = 2                    'peak submenu
            CASE 14, 15
                menu.pos = 3                    'spline submenu
            CASE 16, 17
                menu.pos = 4                    'volume report submenu
            CASE 18, 19
                menu.pos = 5
                menu.pos = 6                    'configuration submenu
        END SELECT
        menu.color(menu.pos) = 15
        GOSUB d.down
    ELSE
        GOSUB quit                              'exit program
        GOSUB disk.menu.on                      'otherwise turn key trapping on
        GOSUB d.down                            '???? otherwise it hi-lights the next item up
        GOSUB disk.menu                         'display disk menu
    END IF d.up:
    IF menu.pos = 1 THEN                        'move cursor up one menu item
        menu.pos = 9                            'if cursor is at 1st item, move to last
        menu.color(1) = 7
    ELSEIF menu.pos > 9 AND INT(menu.pos / 2) = menu.pos / 2 THEN  'move between items in sub menu
        menu.pos = menu.pos + 1
        menu.color(menu.pos) = 15
        menu.color(menu.pos - 1) = 7
    ELSEIF menu.pos > 9 AND INT(menu.pos / 2) <> menu.pos / 2 THEN 'move between items in sub menu
        menu.pos = menu.pos - 1
        menu.color(menu.pos) = 15
        menu.color(menu.pos + 1) = 7
    ELSE                                        'otherwise move cursor up
        menu.pos = menu.pos - 1
        menu.color(menu.pos + 1) = 7
    END IF
    menu.color(menu.pos) = 15                   'hilight menu item
    GOSUB disk.menu
RETURN d.down:
    IF menu.pos = 9 THEN                        'move cursor down one menu item
        menu.pos = 1                            'if cursor is at last item, move to 1st
        menu.color(9) = 7
    ELSEIF menu.pos > 9 AND INT(menu.pos / 2) = menu.pos / 2 THEN  'move between items in sub menu
        menu.pos = menu.pos + 1
        menu.color(menu.pos) = 15
        menu.color(menu.pos - 1) = 7
    ELSEIF menu.pos > 9 AND INT(menu.pos / 2) <> menu.pos / 2 THEN 'move between items in sub menu
        menu.pos = menu.pos - 1
        menu.color(menu.pos) = 15
        menu.color(menu.pos + 1) = 7
```

```
        ELSE
            menu.pos = menu.pos + 1                                 'move cursor down
            menu.color(menu.pos - 1) = 7
        END IF
        menu.color(menu.pos) = 15                                   'hilight menu item
        GOSUB disk.menu
    RETURN d.change:
    GOSUB keys.off
    SELECT CASE menu.pos
        CASE 1                                                      'select menu item
            exit$ = "n"
            DO
                LOCATE 21
                COLOR 15
                PRINT TAB(16); "choose type of screen M)ono or H)i-res color:  ";   'choose type of monitor
                COLOR 7
                scr$ = UCASE$(INPUT$(1))
                PRINT scr$
                exit$ = "y"
                SELECT CASE scr$
                    CASE "M"
                        scrtype$ = "Mono"
                        scr = 2                                     'set screen mode to 2 - Monochrome
                        yaxismin = 13                               'set minimum y position for graphical display
                        yaxismax = 169                              'set maximum y position for graphical display
                        ticky = 188                                 'sets y position of tick mark below x-axis
                        marky = 193                                 'sets y position of marked peaks
                    CASE "H"
                        scrtype$ = "Hi-Res Color"
                        scr = 9
                        yaxismin = 30                               'set minimum y position for graphical display
                        yaxismax = 296                              'set maximum y position for graphical display
                        ticky = 333                                 'sets y position of tick mark below x-axis
                        marky = 340                                 'sets y position of marked peaks
                    CASE CHR$(13)
                    CASE ELSE
                        exit$ = "n"
                END SELECT
            LOOP UNTIL exit$ = "y"
            exit$ = "n"
        CASE 2                                                      'select tube data file characteristics
            menu.pos = 10
            menu.color(2) = 7
            menu.color(10) = 15
            GOSUB disk.menu
        CASE 3                                                      'select peak data file characteristics
            menu.pos = 12
            menu.color(3) = 7
            menu.color(12) = 15
```

```
CASE 4    GOSUB disk.menu                              'select spline data file characteristics menu.pos = 14
          menu.color(4) = 7
          menu.color(14) = 15
          GOSUB disk.menu CASE 5    menu.pos = 16                                'select volume data file characteristics
          menu.color(5) = 7
          menu.color(16) = 15
          GOSUB disk.menu CASE 6    menu.pos = 18                                'select config data file characteristics
          menu.color(6) = 7
          menu.color(18) = 15
          GOSUB disk.menu CASE 7    LOCATE 22                                    'enter base path and name for all files
          COLOR 15
          PRINT TAB(9); "enter the path and basename (up tp 6 char.) for the tube data"
          COLOR 7
          INPUT "", bs$
          bs$ = UCASE$(bs$)
          IF LEN(bs$) > 0 THEN
              check$ = "y"
              CALL check.name.path(check$, bs$, bs.nm$, bs.pt$)
              IF check$ = "n" THEN                     'check that file has correct format
                  BEEP                                 ' beep if it doesn't
              ELSE                                     ' otherwise change file names
                  base.path$ = bs.pt$
                  base.name$ = bs.nm$
                  tube.path$ = bs.pt$
                  tube.name$ = bs.nm$
                  peak.path$ = bs.pt$
                  peak.name$ = bs.nm$
                  spline.path$ = bs.pt$
                  spline.name$ = bs.nm$
                  volume.path$ = bs.pt$
                  volume.name$ = bs.nm$
                  config.path$ = bs.pt$
                  config.name$ = bs.nm$
              END IF
          END IF CASE 8    exit$ = "n"                                  'display directory of current files
          DO
              LOCATE 21
              COLOR 15
              PRINT "D)isplay T)ube P)eak S)pline V)olume C)onfiguration or A)ll files? ";
              COLOR 7
```

```
which$ = UCASE$(INPUT$(1))
PRINT which$
exit$ = "y"
okay$ = "y"
SELECT CASE which$
    CASE "T"
        CLS
        PRINT "Directory Path = "; UCASE$(tube.path$)
        PRINT "Current Path = ";
        FILES tube.path$ + "*" + tube.exten$
        IF okay$ = "n" THEN
            PRINT
            PRINT "There are no tube files with the "; tube.exten$; " extension in this directory"
            PRINT
        END IF
        PRINT "press any key to continue"
        x$ = INPUT$(1)
    CASE "P"
        CLS
        PRINT "Directory Path = "; UCASE$(tube.path$)
        PRINT "Current Path = ";
        FILES peak.path$ + "*" + peak.exten$
        IF okay$ = "n" THEN
            PRINT
            PRINT "There are no peak files with the "; peak.exten$; " extension in this directory"
            PRINT
        END IF
        PRINT "press any key to continue"
        x$ = INPUT$(1)
    CASE "S"
        CLS
        PRINT "Directory Path = "; UCASE$(spline.path$)
        PRINT "Current Path = ";
        FILES spline.path$ + "*" + spline.exten$
        IF okay$ = "n" THEN
            PRINT
            PRINT "There are no spline fit files with the "; spline.exten$; " extension in this directory"
            PRINT
        END IF
        PRINT "press any key to continue"
        x$ = INPUT$(1)
    CASE "V"
        CLS
        PRINT "Directory Path = "; UCASE$(tube.path$)
        PRINT "Current Path = ";
        FILES volume.path$ + "*" + volume.exten$
        IF okay$ = "n" THEN
            PRINT
            PRINT "There are no volume profile files with the "; volume.exten$; " extension in this directory"
            PRINT
        END IF
```

```
                    PRINT "press any key to continue"
                    x$ = INPUT$(1)
              CASE "C"
                    CLS
                    PRINT "Directory Path = "; UCASE$(par.path$)
                    PRINT "Current Path = ";
                    FILES config.path$ + "*" + config.exten$
                    IF okay$ = "n" THEN
                          PRINT
                          PRINT "There are no parameter files with the "; config.exten$; " extension in this directory"
                          PRINT
                    END IF
                    PRINT "press any key to continue"
                    x$ = INPUT$(1)
              CASE "A"
                    INPUT "Enter path of directory: "; path$
                    IF path$ <> "" THEN
                          IF RIGHT$(path$, 1) <> "\" THEN path$ = path$ + "\"
                          CLS
                          PRINT "Directory Path = "; UCASE$(path$)
                          PRINT "Current Path = ";
                          FILES path$
                          IF okay$ = "n" THEN
                                PRINT
                                PRINT "There are no files in this directory"
                                PRINT
                          END IF
                          PRINT "press any key to continue"
                          x$ = INPUT$(1)
                    END IF
              CASE CHR$(13)
              CASE ELSE
                    exit$ = "n"
        END SELECT
        okay$ = "y"
  LOOP UNTIL exit$ = "y"
  exit$ = "n"
CASE 9
        DO                                      'delete selected files
              LOCATE 21
              COLOR 15
              PRINT TAB(14); "delete the selected name of which type of data files"
              PRINT TAB(10); "T)ube  P)eak  S)pline  V)olume  C)onfiguration  A)ll  or  E)xit: ";
              COLOR 7
              which$ = UCASE$(INPUT$(1))
              PRINT which$
              exit$ = "y"
              SELECT CASE which$
                    CASE "T"
                          PRINT TAB(30); "Are you sure (y/n): ";
                          sure$ = UCASE$(INPUT$(1))
```

```
                        PRINT sure$
                        IF sure$ = "y" THEN KILL tube.path$ + tube.name$ + "?" + tube.extens$
                CASE "P"
                        PRINT TAB(30); "Are you sure (y/n): ";
                        sure$ = UCASE$(INPUT$(1))
                        PRINT sure$
                        IF sure$ = "y" THEN KILL peak.path$ + peak.name$ + "?" + peak.extens$
                CASE "S"
                        PRINT TAB(30); "Are you sure (y/n): ";
                        sure$ = UCASE$(INPUT$(1))
                        PRINT sure$
                        IF sure$ = "y" THEN KILL spline.path$ + spline.name$ + "?" + spline.extens$
                CASE "V"
                        PRINT TAB(30); "Are you sure (y/n): ";
                        sure$ = UCASE$(INPUT$(1))
                        PRINT sure$
                        IF sure$ = "y" THEN KILL volume.path$ + volume.name$ + volume.extens$
                CASE "C"
                        PRINT TAB(30); "Are you sure (y/n): ";
                        sure$ = UCASE$(INPUT$(1))
                        PRINT sure$
                        IF sure$ = "y" THEN KILL config.path$ + config.name$ + config.extens$
                CASE "A"
                        PRINT TAB(30); "Are you sure (y/n): ";
                        sure$ = UCASE$(INPUT$(1))
                        PRINT sure$
                        IF sure$ = "y" THEN
                                KILL tube.path$ + tube.name$ + "*.tub"
                                KILL peak.path$ + peak.name$ + "*.pk"
                                KILL spline.path$ + spline.name$ + "*.spl"
                                KILL volume.path$ + volume.name$ + ".vol"
                                KILL config.path$ + config.name$ + ".con"
                        END IF
                CASE "E"
                CASE CHR$(13)
                CASE ELSE
                        exit$ = "n"
                END SELECT
        LOOP UNTIL exit$ = "y"
        exit$ = "n"
CASE 10, 12, 14, 16, 18
        LOCATE 21
        PRINT SPACES(79); : PRINT SPACES(79);
        LOCATE 21
        COLOR 15
        PRINT TAB(15); "enter the location and basename to save this data"
        COLOR 7
        LOCATE (menu.pos / 2 + 2), 30
        PRINT SPACES(40);
        LOCATE (menu.pos / 2 + 2), 30
```
'change path and name of data file

```
INPUT "", files
files = UCASE$(files)
IF LEN(files) > 0 THEN
    check$ = "y"
    CALL check.name.path(check$, files, file.name$, file.path$)    'check file format
    IF check$ = "n" THEN                                           ' beep if it's wrong
        BEEP
    ELSE                                                           ' otherwise change file names
        SELECT CASE menu.pos
            CASE 10
                tube.path$ = file.path$
                tube.name$ = file.name$
            CASE 12
                peak.path$ = file.path$
                peak.name$ = file.name$
            CASE 14
                spline.path$ = file.path$
                spline.name$ = file.name$
            CASE 16
                volume.path$ = file.path$
                volume.name$ = file.name$
            CASE 18
                config.path$ = file.path$
                config.name$ = file.name$
        END SELECT
        menu.color(menu.pos) = 7
        menu.pos = menu.pos / 2 - 3                                'return to menu
        menu.color(menu.pos) = 15
    END IF
END IF CASE 11, 13, 15, 17, 19                 'enable/disable saving of data files
    LOCATE 21
    PRINT SPACES(79); : PRINT SPACES(79);
    LOCATE 21
    COLOR 15
    PRINT TAB(16); "enable (Y) or disable (N) the saving of this data"
    COLOR 7
    LOCATE ((menu.pos - 1) / 2 + 2), 70
    PRINT SPACES(9);
    DO
        exit$ = "y"
        LOCATE ((menu.pos - 1) / 2 + 2), 72
        enable$ = UCASE$(INPUT$(1))
        PRINT enable$
        SELECT CASE enable$
            CASE "y"                                               'enable saving
                SELECT CASE menu.pos
                    CASE 11
                        save.tube$ = "y"
                    CASE 13
                        save.peak$ = "y"
```

```
                            CASE 15
                                save.splines = "y"
                            CASE 17
                                save.volumes = "y"
                            CASE 19
                                save.configs = "y"
                        END SELECT
                        menu.color(menu.pos) = 7
                        menu.pos = (menu.pos - 1) / 2 - 3
                        menu.color(menu.pos) = 15
                CASE "N"                                            'return to menu
                    SELECT CASE menu.pos
                            CASE 11
                                save.tubes = "n"
                            CASE 13
                                save.peaks = "n"
                            CASE 15
                                save.splines = "n"
                            CASE 17
                                save.volumes = "n"
                            CASE 19
                                save.configs = "n"                  'disable saving
                        END SELECT
                        menu.color(menu.pos) = 7
                        menu.pos = (menu.pos - 1) / 2 - 3
                        menu.color(menu.pos) = 15
                CASE CHR$(13)
                CASE ELSE
                        exit$ = "n"
            END SELECT
        LOOP UNTIL exit$ = "y"
    END SELECT
    GOSUB disk.menu.on
    GOSUB disk.menu
RETURN
'--------------- scan data -----------------------------------------------------   'return to menu
'-------------------------------------------------------------------------------
scanning:
    GOSUB keys.off
    IF save.configs = "y" THEN                                      'save configuration and begin scan
        OPEN config.paths + config.name$ + config.exten$ FOR OUTPUT AS #1
            IF path.quit$ = "y" THEN                                'if path is incorrect, return to menu
                path.quit$ = "n"
                BEEP
                CLS
                LOCATE 12
                PRINT TAB(22); "Invalid Path Specified for Data File"
                PRINT
                PRINT TAB(22); "press any key to return to main menu"
```

```
        zz$ = INPUT$(1)
        GOSUB main.menu.on
        GOSUB main.menu
        RETURN
END IF PRINT #1, tube.paths
PRINT #1, tube.names
PRINT #1, save.tubes
PRINT #1, peak.paths
PRINT #1, peak.names
PRINT #1, save.peaks
PRINT #1, spline.paths
PRINT #1, spline.names
PRINT #1, save.splines
PRINT #1, volume.paths
PRINT #1, volume.names
PRINT #1, save.volumes
PRINT #1, config.paths
PRINT #1, config.names
PRINT #1, save.configs
PRINT #1, slice
PRINT #1, number
PRINT #1, dist.interval
PRINT #1, step.interval
PRINT #1, type.tubes
PRINT #1, scan.start
PRINT #1, scan.end
PRINT #1, length
PRINT #1, motor.ports
PRINT #1, translator
PRINT #1, rotator
PRINT #1, tran.speed
PRINT #1, rot.speed
PRINT #1, tran.rev
PRINT #1, rot.rev
PRINT #1, screw.rev
PRINT #1, sample
PRINT #1, timer.rate
PRINT #1, n1
PRINT #1, n2
PRINT #1, timer.freq
PRINT #1, low.scan
PRINT #1, high.scan
PRINT #1, io.add
PRINT #1, interrupt
PRINT #1, dma.level
PRINT #1, thickness
PRINT #1, errtol
PRINT #1, incout
```

```
        PRINT #1, max.pk.wid
        PRINT #1, min.pk.wid
        PRINT #1, pos.thresh
        PRINT #1, neg.thresh
        PRINT #1, max.consec
        PRINT #1, min.plateau
        PRINT #1, move.average
        PRINT #1, find.peak$
        PRINT #1, printer.port$
        PRINT #1, scrtype$
        PRINT #1, key.break$
        PRINT #1, "Version"; program.version
        PRINT #1, DATE$
        PRINT #1, scr
        PRINT #1, alum.start
        PRINT #1, alum.end
        PRINT #1, alum.length
        PRINT #1, steel.start
        PRINT #1, steel.end
        PRINT #1, steel.length
        PRINT #1, base.path$
        PRINT #1, base.name$
        CLOSE #1
    END IF
    CHAIN "scanner"
RETURN
'---------------- print or analyze data -----------------
'--------------------------------------------------------
print.analyze:
    GOSUB keys.off
    okay$ = "y"
    OPEN config.path$ + config.name$ + config.exten$ FOR INPUT AS #1   'load configuration and analyze data
    IF path.quit$ = "y" THEN                                            'if path is incorrect, return to menu
        path.quit$ = "n"
        BEEP
        CLS
        LOCATE 12
        PRINT TAB(22); "Invalid Path Specified for Data Files"
        PRINT
        PRINT TAB(22); "press any key to return to main menu"
        zz$ = INPUT$(1)
        GOSUB main.menu.on
        GOSUB main.menu
        RETURN
    END IF IF okay$ = "y" THEN
        old.scr = scr
```

```
old.scrtypes = scrtypes
INPUT #1, tube.paths
INPUT #1, tube.names
INPUT #1, save.tubes
INPUT #1, peak.paths
INPUT #1, peak.names
INPUT #1, save.peaks
INPUT #1, spline.paths
INPUT #1, spline.names
INPUT #1, save.splines
INPUT #1, volume.paths
INPUT #1, volume.names
INPUT #1, save.volumes
INPUT #1, config.paths
INPUT #1, config.names
INPUT #1, save.configs
INPUT #1, slice
INPUT #1, number
INPUT #1, dist.interval
INPUT #1, step.interval
INPUT #1, type.tubes
INPUT #1, scan.start
INPUT #1, scan.end
INPUT #1, length
INPUT #1, motor.ports
INPUT #1, translator
INPUT #1, rotator
INPUT #1, tran.speed
INPUT #1, rot.speed
INPUT #1, tran.rev
INPUT #1, rot.rev
INPUT #1, screw.rev
INPUT #1, sample
INPUT #1, timer.rate
INPUT #1, n1
INPUT #1, n2
INPUT #1, timer.freq
INPUT #1, low.scan
INPUT #1, high.scan
INPUT #1, io.add
INPUT #1, interrupt
INPUT #1, dma.level
INPUT #1, thickness
INPUT #1, errtol
INPUT #1, incout
INPUT #1, max.pk.wid
INPUT #1, min.pk.wid
INPUT #1, pos.thresh
INPUT #1, neg.thresh
INPUT #1, max.consec
INPUT #1, min.plateau
```

```
            INPUT #1, move.average
            INPUT #1, find.peak$
            INPUT #1, printer.port$
            INPUT #1, scrtype$
            INPUT #1, key.break$
            INPUT #1, file.version$
            INPUT #1, file.date$
            INPUT #1, scr
            INPUT #1, alum.start
            INPUT #1, alum.end
            INPUT #1, alum.length
            INPUT #1, steel.start
            INPUT #1, steel.end
            INPUT #1, steel.length
            INPUT #1, base.path$
            INPUT #1, base.name$
            CLOSE #1 min.samp.rate = ((timer.freq / 65535) / 65535    'sets the minimum sampling rate
            max.samp.rate = timer.freq / 4                    'sets the maximum sampling rate
            scr = old.scr                                     'retain screen format
            scrtype$ = old.scrtype$
       ELSE
            CLS
            LOCATE 12
            PRINT TAB(12); "The Program Could Not Find the Selected Parameter File"
            PRINT TAB(22); "Please Re-Check the Entered Values"
            PRINT
            PRINT TAB(27); "press any key to continue"
            zz$ = INPUT$(1)
            okay$ = "y"
            GOSUB main.menu.on
            GOSUB main.menu
            RETURN
       END IF IF print.or.analyze$ = "analyze" THEN
            CHAIN "analyzer"
       ELSE
            CHAIN "printer"
       END IF
RETURN
SUB check.name.path (check$, file$, name$, path$)
'------------ checks format of file paths and names ------------
'---------------------------------------------------------------
       IF LEN(file$) < 4 THEN                                 'at least 4 characters long (c:\x)
            check$ = "n"
       ELSE
            IF ASC(LEFT$(file$, 1)) < 65 OR ASC(LEFT$(file$, 1)) > 90 THEN check$ = "n"   'first character is a letter (signifies drive)
            IF MID$(file$, 2, 2) <> ":\" THEN check$ = "n"    'next two are :\
```

```
          start = 3
          FOR x = 4 TO LEN(files)
                IF (ASC(MID$(files, x, 1)) < 48 AND ASC(MID$(files, x, 1)) <> 45) OR (ASC(MID$(files, x, 1)) > 90 AND ASC(MID$(files, x, 1)) <> 92) THEN  'rest are legal characters
                      check$ = "n"
                IF MID$(files, x, 1) = "\" THEN                          'no directories or filenames are greater than 8 characters
                      dist = x - start - 1
                      IF dist > 8 THEN check$ = "n"
                      start = x
                END IF
          NEXT x
          FOR x = LEN(files) TO 3 STEP -1                                'find file name by working backwards from end to \
                IF MID$(files, x, 1) = "\" THEN                          ' and making sure not more than 6 characters
                      dist = LEN(files) - x - 1
                      IF dist > 6 THEN
                            check$ = "n"
                      ELSE  name.start.pos = x
                            EXIT FOR
                      END IF
                END IF
          NEXT x
          END IF
          IF check$ <> "n" THEN                                          'if everything is okay, pass name and path
                name$ = RIGHT$(files, LEN(files) - x)
                path$ = LEFT$(files, x)
          END IF
END SUB '*********************************************************************
'*********************************************************************
'**********                                                 **********
'**********    Interferometric Measuring Device Scanner     **********
'**********                      v. 2                       **********
'**********                                                 **********
'**********            Written by: Robert Wagner            **********
'**********                    7-18-91                      **********
'**********                                                 **********
'*********************************************************************
'*********************************************************************

DECLARE SUB das16 (md%, dio%, flag%)
COMMON tube.path$, tube.name$, save.tube$, peak.path$, peak.name$, save.peak$
COMMON spline.path$, spline.name$, save.spline$, volume.path$, volume.name$
COMMON save.volume$, config.path$, config.name$, save.config$, slice
COMMON number, dist.interval, step.interval, type.tube$, scan.start, scan.end
COMMON length, motor.port$, translator, rotator, tran.speed, rot.speed
COMMON tran.rev, rot.rev, screw.rev, sample, timer.rate, n1, n2, timer.freq
COMMON low.scan, high.scan, io.add, interrupt, dma.level, thickness, errtol
COMMON incout, max.pk.wid, min.pk.wid, pos.thresh, neg.thresh, max.consec
```

```
COMMON min.plateau, move.average, find.peaks, printer.port$
COMMON scrtype$, key.break$, scr, alum.start, alum.end, alum.length
COMMON steel.start, steel.end, steel.length, base.path$, base.name$ COMMON tube.exten$, peak.exten$, spline.exten$, volume.exten$, config.exten$
COMMON already.running$, xexismin, xexismax, yexismin, yexismax, ticky, marky
COMMON current.menu$, max.number, max.slices, max.samples, program.version ON ERROR GOTO error.handler '------------- define variables ----------------

DIM menu.color(5)

quit$ = "n"
    max.signal = 4095              'maximum signal value of data from A/D board
    max.sample = 1000              'sets maximum number of samplings per data point DIM x%(1000)                   'need a number for A/D board to work DIM check.key$(6)              'arrays dimensioned for use by Arrick stepper motor routines
    DIM check.limit$(6)
    DIM current.position(6)
    DIM direction$(6)
    DIM last.pattern%(6)
    DIM p%(8)
    DIM pn%(8)
    DIM power.down$(6)
    DIM speed%(6)
    DIM steps.to.move(6)
    DIM step.type$(6)
    DIM target.position(6)

DIM dio%(4)                    'array dimensioned for use by A/D board

DIM scan.data(max.number)      'arrays where scanned data is stored
    DIM scan.pos(max.number)

'------------- check to see if this program was called or run directly ----------

IF already.running$ <> "y" THEN
    CLS
    LOCATE 13
    PRINT TAB(24); "Please run the NRL-IMD program first."
    PRINT TAB(25); "This program is not executable."
    END
END IF '------------- main program ----------------
```

```
            GOSUB scan
        DO
        LOOP
    END

'------------------------------ main subroutines ------------------------------
'
'
'
error.handler:                                  'handles errors
    SELECT CASE ERR
        CASE 53        okay$ = "n"              'file not found error
        CASE 61                                 'disk full error
            BEEP
            PRINT
            PRINT TAB(28); "The Current Disk is Full"
            PRINT
            PRINT TAB(15); "press any key to return to the main menu ";
            which$ = UCASE$(INPUT$(1))
            CLOSE
            SCREEN 0
            full.quit$ = "y"
        CASE 76                                 'path not found error
            CLOSE
            path.quit$ = "y"
        CASE ELSE
            BEEP
            PRINT
            PRINT "Error "; ERR; " occurred.  Program aborted."
            PRINT
            CLOSE                               'close all files
            SCREEN 0
            CHAIN "NRL-IMD"
    END SELECT
RESUME NEXT keys.off:                                       'turns off key trapping
    FOR x = 1 TO 25
        KEY(x) OFF
    NEXT x
RETURN quit:                                           'exits program
    GOSUB keys.off
    CLOSE                                       'close all files
    PRINT
```

```
          PRINT TAB(21); "Are you sure you want to quit (Y/N)? ";
          leave$ = UCASE$(INPUT$(1))
          PRINT leave$
          IF leave$ = "Y" THEN END
RETURN
'---------------- scanning menu ----------------
'-----------------------------------------------
scan:
          GOSUB scan.menu.init                'sets up scanning menu
          GOSUB scan.menu.on                  'initializes key trapping for scanning menu
          GOSUB scan.menu                     'turns on key trapping
RETURN                                        'prints scanning menu scan.menu.init:                               'initializes key trapping KEY 15, CHR$(160) + CHR$(72)        'up--up
          KEY 16, CHR$(160) + CHR$(75)        'left--up
          KEY 17, CHR$(160) + CHR$(77)        'right-down
          KEY 18, CHR$(160) + CHR$(80)        'down--down
          KEY 19, CHR$(32)  + CHR$(28)        'RET-change
          KEY 25, CHR$(32)  + CHR$(1)         'ESC-quit ON KEY(1)  GOSUB main.menu          'F1--goto main menu NRL.IMD
          ON KEY(11) GOSUB s.up               'up(cursor)--up one menu item
          ON KEY(12) GOSUB s.up               'left(cursor)--up one menu item
          ON KEY(15) GOSUB s.up               'up(keypad)--up one menu item
          ON KEY(16) GOSUB s.up               'left(keypad)--up one menu item
          ON KEY(13) GOSUB s.down             'right(cursor)--down one menu item
          ON KEY(14) GOSUB s.down             'down(cursor)--down one menu item
          ON KEY(17) GOSUB s.down             'right(keypad)--down one menu item
          ON KEY(18) GOSUB s.down             'down(keypad)--down one menu item
          ON KEY(19) GOSUB s.change           'RET-select menu item
          ON KEY(25) GOSUB s.quit             'ESC--return to scanning menu FOR x = 1 TO 5                      'deselect all menu items (low intensity white)
                menu.color(x) = 7
          NEXT x
          menu.color(1) = 15                  'hilight 1st menu item (high intensity white)
          menu.pos = 1                        'position "cursor" on 1st menu item
RETURN scan.menu.on:
          FOR x = 11 TO 19                    'turn on key trapping
                KEY(x) ON
          NEXT x
          KEY(1) ON
          KEY(25) ON
RETURN scan.menu:                                    'print scanning menu
```

```
         SCREEN 0
         CLS
         PRINT TAB(32); "Scan JFTOT Tube"
         PRINT "--------------------------------------------------------"
         PRINT
         PRINT
         PRINT
         COLOR menu.color(1): PRINT TAB(25); "Scan an Entire Tube"
         COLOR menu.color(2): PRINT TAB(25); "Scan a Range of Slices on a Tube"
         COLOR menu.color(3): PRINT TAB(25); "Scan a Single Slice"
         PRINT
         COLOR menu.color(4): PRINT TAB(25); "Home Translating Probe"
         COLOR menu.color(5): PRINT TAB(25); "Keyboard Break During Scanning";
         COLOR 7: PRINT TAB(65); key.break$
         PRINT
         PRINT
         PRINT TAB(27); "F1-Main Menu          ESC-Quit"
         RETURN                                                        'display scanning menu s.quit:
         GOSUB quit
         GOSUB scan.menu.on
         GOSUB scan.menu
         RETURN s.up:
         IF menu.pos = 1 THEN                                          'move "cursor" up one menu item
                 menu.pos = 5                                          'if cursor is at 1st item, move to last
                 menu.color(1) = 7
         ELSE
                 menu.pos = menu.pos - 1                               'otherwise move cursor up
                 menu.color(menu.pos + 1) = 7
         END IF
         menu.color(menu.pos) = 15
         GOSUB scan.menu
         RETURN s.down:
         IF menu.pos = 5 THEN                                          'move "cursor" down one menu item
                 menu.pos = 1                                          'if cursor is at last item, move to 1st
                 menu.color(5) = 7
         ELSE
                 menu.pos = menu.pos + 1                               'otherwise move cursor down
                 menu.color(menu.pos - 1) = 7
         END IF
         menu.color(menu.pos) = 15
         GOSUB scan.menu
         RETURN s.change:
         GOSUB keys.off                                                'select menu item
         SELECT CASE menu.pos
```

```
CASE 1    start = 1                                              'scan entire tube
          finish = slice                                         'set first slice as 1
          GOSUB scan.tube                                        'set last slice as slice CASE 2    LOCATE 21                                              'scan a range of slices
          COLOR 15
          PRINT TAB(22); "scan a range of slices on this tube"
          PRINT TAB(27); "start - ";
          COLOR 7
          INPUT "", srt$
          COLOR 15
          LOCATE 22, 44
          PRINT "end - ";
          COLOR 7
          INPUT "", fsh$
          srt = INT(VAL(srt$))
          fsh = INT(VAL(fsh$))
          IF srt > 0 AND srt <= fsh AND srt <= slice AND fsh <= slice THEN
                  start = srt                                    'set starting scanning slice
                  finish = fsh                                   'set ending scanning slice
                  GOSUB scan.tube
          ELSE
                  BEEP
          END IF CASE 3    LOCATE 21                                              'scan one slice
          COLOR 15
          PRINT TAB(24); "scan which slice on this tube: ";
          COLOR 7
          INPUT "", srt$
          srt = INT(VAL(srt$))
          IF srt > 0 AND srt <= slice THEN
                  start = srt                                    'set starting slice = ending slice
                  finish = srt
                  GOSUB scan.tube
          ELSE
                  BEEP
          END IF CASE 4    LOCATE 20                                              'return translating motor to "home" position
          COLOR 15
          PRINT TAB(28); "Homing Translating Motor"
          COLOR 7

'------- Initialize Motors -------                     'initialize motors
          GOSUB md2.init
          motor% = translator
          GOSUB md2.off                                          'make sure translator is off
          motor% = rotator
          GOSUB md2.off                                          'make sure rotator is off
```

```
           step.type$(translator) = "H"              'set half step sizes (.9 degree per step)
           power.down$(translator) = "Y"             'make sure motors are powered down
           power.down$(rotator) = "Y"
           check.key$(translator) = "N"              'stop keyboard check to stop motors '---------- Move Translator to origin ----------
'this routine moves the translator to a specific origin set by the limit switch
           motor% = translator                       'set current motor to translator
           speed%(translator) = tran.speed           'set user-defined speed of translator
           direction$(translator) = "F"              'set direction -- F is actually reverse
           check.limits(translator) = "Y"            'make sure limit switch checking is on
           move.action$ = "C"                        'set continuous movement
           GOSUB md2.move                            'move until motor hits limit switch
           check.limits(translator) = "N"            'turn off limit switch checking
           direction$(translator) = "B"              'set direction -- B is actually forwards
           move.action$ = "S"                        'set step movement
           steps.to.move(translator) = 100           'move the translator 100 steps to free limit switch
           GOSUB md2.move                            'move motor
           check.limits(translator) = "Y"            'turn limit switch checking on
                                                     'enable keyboard interrupt of scanning CASE 5
           DO
             LOCATE 19, 1
             COLOR 15
             PRINT TAB(11); "pressing a key on the keyboard will stop the scan (Y/N) ";
             COLOR 7
             which$ = UCASE$(INPUT$(1))
             exit$ = "Y"
             SELECT CASE which$
                  CASE "Y"
                       key.break$ = "yes"
                  CASE "N"
                       key.break$ = "no"
                  CASE CHR$(13)
                  CASE ELSE
                       exit$ = "n"
             END SELECT
           LOOP UNTIL exit$ = "Y"

END SELECT
     GOSUB scan.menu.on
     GOSUB scan.menu
RETURN main.menu:
     SCREEN 0                                        'return to main menu NRL-IMD
     current.menu$ = "main"                          'set text screen
     CHAIN "NRL-IMD"                                 'set main menu
RETURN '---------- scan tube ----------
```

```
scan.tube:

CLS

'----------- Initialize Motors ----------
      GOSUB md2.init                              'initialize motors
      motor% = translator
      GOSUB md2.off                               'make sure translator is off
      motor% = rotator
      GOSUB md2.off                               'make sure rotator is off step.type$(translator) = "H"                'set half step sizes (.9 degree per step)
      step.type$(rotator) = "H"
      power.down$(translator) = "Y"               'make sure motors are powered down
      power.down$(rotator) = "Y"
      IF key.break$ = "yes" THEN
          check.key$(translator) = "Y"            'set keyboard check to stop scanning
          check.key$(rotator) = "Y"
      ELSE
          check.key$(translator) = "N"            'set keyboard check to not stop scanning
          check.key$(rotator) = "N"
      END IF
      check.limit$(translator) = "Y"              'set translating motor limit switch check on
      check.limit$(rotator) = "N"                 'set rotating motor limit switch check off - not used '----------- Initialize A/D Board ----------
      md% = 0
      flag% = 99
      dio%(0) = io.add                            'sets mode 0 -- page 25 of Metrabyte manual
      dio%(1) = interrupt                         'sets I/O address
      dio%(2) = dma.level                         'sets interrupt level
      CALL das16(md%, dio%(0), flag%)             'sets DMA level
                                                  'accesses A/D board IF flag% = 22 THEN                          'checks to see if A/D board is at correct address
          CLS
          LOCATE 12
          PRINT "Incorrect I/O base address for A/D board.  Please check and reconfigure set-up."
          DO
              LOCATE 14
              PRINT TAB(25); "Press Q to return to scan menu"
              ret$ = UCASE$(INPUT$(1))
              IF ret$ = "Q" THEN RETURN
          LOOP
      END IF '----------- Set Scanning Limits on Multiplexer ---------- md% = 1                                     'sets mode 1 -- page 27 of Metrabyte manual
```

```
dioX(0) = low.scan                                          'sets lower scanning limit
dioX(1) = high.scan                                         'sets upper scanning limit
flagX = 99
CALL das16(mdX, dioX(0), flagX)                             'accesses A/D board IF flagX = 6 OR flagX = 7 THEN                              'checks the low and high scan limits
   CLS
   LOCATE 12
   PRINT TAB(25); "The low and/or high scan limits for the A/D board are incorrect."
   DO
      LOCATE 14
      PRINT TAB(8); "Press Q to return to scan menu"
      ret$ = UCASE$(INPUT$(1))
      IF ret$ = "Q" THEN RETURN
   LOOP
END IF '------------- Set Sampling Rate ------------- mdX = 17                                                    'sets mode 17 -- page 50 of Metrabyte manual
dioX(0) = n1                                                'sets one counter
dioX(1) = n2                                                'sets other counter
flagX = 99
CALL das16(mdX, dioX(0), flagX)                             'accesses A/D board '------------- Prompt User to Remove Tubes to Initialize Motor Placement -------------

LOCATE 10, 1
PRINT TAB(20); "Remove any tubes from the Tube Reader"
PRINT
PRINT TAB(22); "Press any key to initialize motors"
x$ = INPUT$(1)
CLS '------------- Move Rotator One Complete Revolution -------------
'this routine moves the translator one full revolution before the tube is inserted to get the motor ready before scanning LOCATE 12
PRINT TAB(30); "Initializing Rotator"
motorX = rotator                                            'set current motor to rotator
speedX(rotator) = rot.speed                                 'set user-defined speed of rotator
direction$(rotator) = "F"                                   'set direction of rotation
move.action$ = "S"                                          'set step controlled movement
steps.to.move(rotator) = rot.rev                            'set motor to move one complete revolution
GOSUB md2.move                                              'move motor '------------- Move Translator to Origin -------------
'this routine moves the translator to a specific origin set by the limit switch LOCATE 14
PRINT TAB(29); "Initializing Translator"
```

```
motorX = translator                                    'set current motor to translator
speedX(translator) = tran.speed                        'set user-defined speed of translator
directionS(translator) = "F"                           'set direction -- F is actually reverse
move.actionS = "C"                                     'set continuous movement
GOSUB md2.move                                         'move until motor hits limit switch
directionS(translator) = "B"                           'set direction -- B is actually forwards
move.actionS = "S"                                     'set step movement
check.limitS(translator) = "N"                         'turn off limit switch check to move probe off limit switch
steps.to.move(translator) = 100                        'move the translator 100 steps to free limit switch
GOSUB md2.move                                         'move motor
check.limitS(translator) = "Y"                         'turn limit switch back on '------------- Set-up User Conditions ------------- speedX(translator) = tran.speed                        'set translator motor speed
speedX(rotator) = rot.speed                            'set rotator motor speed
directionS(translator) = "B"                           'set translator motor direction to forwards -- B
move.actionS = "S"                                     'set step oriented movement '------------- Operator Inserts Tube ------------- quitS = "n"
DO
    CLS
    LOCATE 10, 1
    PRINT TAB(15); "Please Insert the Tube to be Read in the Reader"
    PRINT
    PRINT TAB(18); "press R to Read, Q to return to main menu"
    optS = UCASES(INPUTS(1))
    SELECT CASE optS
        CASE "R"
            quitS = "y"
            mainS = "n"
        CASE "Q"
            quitS = "y"
            mainS = "y"
        CASE ELSE
            quitS = "n"
    END SELECT
LOOP WHILE quitS <> "y"

IF mainS = "y" THEN RETURN

'------------- Move Translator to Starting Position -------------

CLS
LOCATE 12
PRINT TAB(25); "Moving Motor to Starting Position"
motorX = translator                                    'set current motor to translator
steps.to.move(translator) = scan.start * tran.rev / screw.rev    'set steps to move to move translator to starting position
GOSUB md2.move                                         'move motor
```

```
SELECT CASE return.status$
    CASE "L"
        BEEP
        CLS
        LOCATE 12
        PRINT TAB(13); "The translating motor has encountered a limit switch."
        PRINT
        PRINT TAB(8); "The scan exceeds the length of the tube, so the scan was aborted"
        PRINT TAB(6); "to avoid damaging the equipment.  Please recheck entered parameters."
        PRINT
        PRINT TAB(18); "press any key to return to the scanning menu"
        zz$ = INPUT$(1)
        RETURN CASE "K"
        BEEP
        DO
            LOCATE 23, 10
            PRINT SPACE$(60);
            LOCATE 23
            PRINT TAB(25); "Key Pressed - Abort Scan (Y/N) ";
            abort$ = UCASE$(INPUT$(1))
            exit$ = "y"
            SELECT CASE abort$
                CASE "Y"
                    RETURN
                CASE "N"
                    LOCATE 23, 25
                    PRINT SPC(35);
                CASE ELSE
                    exit$ = "n"
            END SELECT
        LOOP UNTIL exit$ = "y"
END SELECT '-------- Set-up Rotator Variable's --------------- rot.pos = 0                                           'set rotational position to zero
rot.interval = INT(rot.rev / slice)                   'define number of steps between slices '-------- Rotate Tube to Correct Starting Slice --------

FOR rot.slice = 1 TO start - 1
    motor% = rotator                                  'set motor to rotator
    steps.to.move(rotator) = rot.interval             'move to the next slice
    GOSUB md2.move                                    'move motor
    IF return.status$ = "K" THEN
        BEEP
        DO
            LOCATE 23, 25
            PRINT "Key Pressed - Abort Scan (Y/N) ";
            abort$ = UCASE$(INPUT$(1))
```

```
            exit$ = "y"
            SELECT CASE abort$
                CASE "y"
                    RETURN
                CASE "n"
                    LOCATE 23, 25
                    PRINT SPACES(35);
                CASE ELSE
                    exit$ = "n"
            END SELECT
        LOOP UNTIL exit$ = "y"
    END IF
    rot.pos = rot.pos + rot.interval          'increase rotational position counter
NEXT rot.slice '---------- Begin Scanning ----------

FOR current.slice = start TO finish           'loop from first slice to last slice '---------- initialize translator position variables ---------- step.pos = 0
    dist.pos = 0

'---------- draw and set-up output graph ----------

SCREEN scr
    CLS
    PRINT TAB(5); "Scanning data for tube: "; tube.name$ + LTRIM$(STR$(current.slice)) + tube.exten$; TAB(56); "press <space> to abort"
    mult = (yaxismax - yaxismin) / 9

'---------- draw x-axis ----------

LINE (xaxismin, yaxismax + 1)-(xaxismax, yaxismax + 1), 2
    FOR y = 1 TO 14
        LINE (y * 41 + xaxismin, yaxismax + 1)-(y * 41 + xaxismin, yaxismax + 6), 2
    NEXT y LOCATE 23, 4
    PRINT "0 mm"
    LOCATE 23, 74
    PRINT length '---------- draw y-axis ----------

LOCATE 8
    PRINT "i"
    PRINT "n"
    PRINT "t"
    PRINT "e"
    PRINT "n"
    PRINT "s"
```

```
                PRINT "!"
                PRINT "t"
                PRINT "y"
                LINE (xaxismin - 1, yaxismin)-(xaxismin - 1, yaxismax), 2
                FOR y = 1 TO 9
                    LINE (xaxismin - 6, yaxismax - y * mult)-(xaxismin - 1, yaxismax - y * mult), 2
                NEXT y
'------------ draw in grids ------------

IF scr = 9 THEN

'------------ draw horizontal grid ------------
                FOR y = 1 TO 9
                    FOR xpos = xaxismin TO xaxismax STEP 10
                        PSET (xpos, yaxismax - y * mult), 7
                    NEXT xpos
                NEXT y '------------ draw vertical grid ------------
                FOR y = 1 TO 14
                    FOR ypos = yaxismin TO yaxismax STEP 10
                        PSET (y * 41 + xaxismin, ypos), 7
                    NEXT ypos
                NEXT y

END IF

'------------ set up initial variables for scanning a slice ------------ motor% = translator                                     'set motor to translator
        steps.to.move(translator) = step.interval               'set number of steps to move between each point FOR current.number = 1 TO number                        'scan along a slice '------------ move motor and motor position pointers ------------

GOSUB md2.move                                      'move translator
            SELECT CASE return.status$
                CASE "L"
                    BEEP
                    CLS
                    LOCATE 12
                    PRINT TAB(13); "The translating motor has encountered a limit switch."
                    PRINT
                    PRINT TAB(8); "The scan exceeds the length of the tube, so the scan was aborted"
                    PRINT TAB(6); "to avoid damaging the equipment.  Please recheck entered parameters."
                    PRINT
                    PRINT TAB(18); "press any key to return to the scanning menu"
                    zz$ = INPUT$(1)
                    RETURN
```

```
        CASE "K"
            BEEP
            DO
                LOCATE 23, 10
                PRINT SPACE$(60);
                LOCATE 23, 25
                PRINT "Key Pressed - Abort Scan (Y/N) ";
                abort$ = UCASE$(INPUT$(1))
                exit$ = "y"
                SELECT CASE abort$
                    CASE "Y"
                        RETURN
                    CASE "N"
                        LOCATE 23, 25
                        PRINT SPC(35);
                    CASE ELSE
                        exit$ = "n"
                END SELECT
            LOOP UNTIL exit$ = "y"
END SELECT '----------- increment position counters ----------- step.pos = step.pos + step.interval              'increment step counter
dist.pos = dist.pos + dist.interval              'increment distance counter '----------- sample data at this location sample times ----------- md% = 4                                          'use mode 4 -- pg 31 of Metrabyte manual -- to sample each pt sample # of times
dio%(0) = sample                                 'set number of samples to be taken
dio%(2) = 1                                      'set computer controlled trigger to start data
flag% = 99
dio%(1) = VARPTR(x%(1))                          'puts data into array x%()
CALL das16(md%, dio%(0), flag%)                  'access A/D board '----------- Average Data ----------- sum = 0
FOR y = 1 TO sample                              'sums data to be averaged
    sum = sum + x%(y)
NEXT y scan.data(current.number) = sum / sample         'stores averaged data
scan.pos(current.number) = dist.pos              'stores position in mm '----------- print to screen graph -----------

PSET (scan.pos(current.number) * (xaxismax - xaxismin) / length + xaxismin, (yaxismax - scan.data(current.number) * (yaxismax
```

```
            LOCATE 23, 23
            PRINT "Number: "; current.number
            LOCATE 23, 53
            PRINT "Slice: "; current.slice NEXT current.number '--------- one slice completed ---------------

'--------- check to see if file already exists ---------------

IF save.tube$ = "y" THEN
            okay$ = "y"
            save.data$ = "y"
            path.quit$ = "n"
            full.quit$ = "n"

IF current.slice = 100 THEN
                OPEN tube.path$ + tube.name$ + "00" + tube.exten$ FOR INPUT AS #1
            ELSE
                OPEN tube.path$ + tube.name$ + LTRIM$(STR$(current.slice)) + tube.exten$ FOR INPUT AS #1
            END IF
            CLOSE #1

IF path.quit$ = "y" THEN           'if path is incorrect, return to menu
                path.quit$ = "n"
                RETURN
            END IF IF okay$ = "y" THEN                'if there is no file by this name, the error.handler will turn okay$ into "n"
                BEEP
                quit$ = "n"
                DO
                    CLS
                    PRINT "This file already exists"
                    PRINT
                    PRINT "Continue Scan and ..."
                    PRINT "    1.  Replace just this file with the scanned data"
                    PRINT "    2.  Replace ALL the files to be scanned with newly scanned data"
                    PRINT "    3.  Do not save data and continue scanning"
                    PRINT
                    PRINT "P.  Print Directory of Current Path"
                    PRINT "Q.  Quit Sampling and Return to Main Menu"
                    PRINT
                    PRINT "Enter Selection: ";
                    select$ = UCASE$(INPUT$(1))
                    PRINT select$ SELECT CASE select$
                        CASE "1"
```

```
            PRINT
            PRINT "are you sure you want to replace this file (Y/N)? ";
            del.files = UCASE$(INPUT$(1))
            PRINT del.files
            IF del.files = "Y" THEN
                IF current.slice = 100 THEN
                    KILL tube.path$ + tube.name$ + "00" + tube.exten$
                ELSE
                    KILL tube.path$ + tube.name$ + LTRIM$(STR$(current.slice)) + tube.exten$
                END IF
                PRINT
                PRINT "File Deleted"
            END IF
            quit$ = "y"
            save.data$ = "y"
    CASE "2"
            PRINT
            PRINT "are you sure you want to replace all these files (Y/N)? ";
            del.files = UCASE$(INPUT$(1))
            PRINT del.files
            IF del.files = "Y" THEN
                IF slice = 100 THEN
                    FOR y = current.slice TO slice - 1
                        KILL tube.path$ + tube.name$ + LTRIM$(STR$(y)) + tube.exten$
                    NEXT y
                    KILL tube.path$ + tube.name$ + "00" + tube.exten$
                ELSE
                    FOR y = current.slice TO slice
                        KILL tube.path$ + tube.name$ + LTRIM$(STR$(y)) + tube.exten$
                    NEXT y
                END IF
                PRINT
                PRINT "Files Deleted"
            END IF
            quit$ = "y"
            save.data$ = "y"
    CASE "3"
            quit$ = "y"
            save.data$ = "n"
    CASE "p"
            PRINT
            PRINT "Directory of: "; tube.path$ + "*.*"
            FILES tube.path$ + "*.*"
            PRINT
            PRINT "press any key to continue"
            x$ = INPUT$(1)
    CASE "q"
            '-------- Turn Off Motors ------------
            motor% = translator
            GOSUB md2.off                                       'turn off translator
            motor% = rotator
```

```
                        GOSUB md2.off            'turn off rotator
        END SELECT      RETURN
     LOOP UNTIL quit$ = "y"

quit$ = "n"
     CLS

END IF

'--------- save slice to disk ---------

IF save.data$ = "y" THEN
     SCREEN 0
     CLS
     LOCATE 12
     PRINT TAB(28); "Saving Data for Slice "; current.slice
     IF current.slice = 100 THEN
         OPEN tube.path$ + tube.name$ + "00" + tube.exten$ FOR OUTPUT AS #1
     ELSE
         OPEN tube.path$ + tube.name$ + LTRIM$(STR$(current.slice)) + tube.exten$ FOR OUTPUT AS #1
     END IF
     PRINT #1, CHR$(34) + "Version"; program.version; CHR$(34); CHR$(34) + DATE$ + CHR$(34)
     PRINT #1, number
     FOR y = 1 TO number
         PRINT #1, USING "###.###"; CLNG(1000 * scan.pos(y)) / 1000;
         PRINT #1, USING " ###.#"; CLNG(10 * scan.data(y)) / 10
         IF full.quit$ = "y" THEN           'if disk is full, return to menu
             full.quit$ = "n"
             RETURN
         END IF
     NEXT y
     CLOSE #1
     save.data$ = "y"
 END IF '--------- return motor to start ---------

PRINT
 PRINT TAB(23); "Returning Motor to Begin Next Slice"
 motor% = translator                              'set motor to translator
 direction$(translator) = "r"                     'set direction to reverse -- R
 steps.to.move(translator) = step.pos             'move an equal number of setps back to original starting position
 GOSUB md2.move                                   'move motor
 SELECT CASE return.status$
     CASE "L"
         BEEP
         CLS
         LOCATE 12
```

```
                PRINT TAB(13); "The translating motor has encountered a limit switch."
                PRINT
                PRINT TAB(8); "The scan exceeds the length of the tube, so the scan was aborted"
                PRINT TAB(6); "to avoid damaging the equipment.  Please recheck entered parameters."
                PRINT
                PRINT TAB(18); "press any key to return to the scanning menu"
                zz$ = INPUT$(1)
                RETURN
        CASE "K"
                BEEP
                DO
                        LOCATE 23, 10
                        PRINT SPACE$(60);
                        LOCATE 23, 25
                        PRINT "Key Pressed - Abort Scan (Y/N) ";
                        abort$ = UCASE$(INPUT$(1))
                        exit$ = "y"
                        SELECT CASE abort
                                CASE "Y"
                                        RETURN
                                CASE "N"
                                        LOCATE 23, 25
                                        PRINT SPC(35);
                                CASE ELSE
                                        exit$ = "n"
                        END SELECT
                LOOP UNTIL exit$ = "y"
        END SELECT direction$(translator) = "B"                    'set direction back to forwards -- B '------------- rotate tube ------------- motor% = rotator                                'set motor to rotator
        steps.to.move(rotator) = rot.interval           'move to the next slice
        GOSUB md2.move                                  'move motor
        IF return.status$ = "K" THEN
                BEEP
                DO
                        LOCATE 23, 10
                        PRINT SPACE$(60);
                        LOCATE 23, 25
                        PRINT "Key Pressed - Abort Scan (Y/N) ";
                        abort$ = UCASE$(INPUT$(1))
                        exit$ = "y"
                        SELECT CASE abort
                                CASE "Y"
                                        RETURN
                                CASE "N"
                                        LOCATE 23, 25
                                        PRINT SPACE$(35);
```

```
                    CASE ELSE
                        exit$ = "n"
                    END SELECT
            LOOP UNTIL exit$ = "y"
        END IF rot.pos = rot.pos + rot.interval        'increase rotational position counter NEXT current.slice '---------- Tube Scanning Complete ----------

'---------- Turn Off Motors ---------- motor% = translator
GOSUB md2.off                                   'turn off translator
motor% = rotator
GOSUB md2.off                                   'turn off rotator '---------- Inform User Scanning Done ----------

BEEP
CLS
LOCATE 11
PRINT TAB(30); "Tube Scanning Complete"
PRINT
PRINT
PRINT TAB(28); "press any key to continue"
x$ = INPUT$(1)

RETURN

'*********************************************************
'*********************                       *************
'*********************                       *************
'*********************  MD-2 QUICK-BASIC SUBROUTINES  ****
'*********************                       *************
'*********************  COPYRIGHT (C) 1988,1989  *********
'*********************     ARRICK ROBOTICS       *********
'*********************   ALL RIGHTS RESERVED     *********
'*********************                       *************
'*********************                       *************
'*********************************************************

'PROGRAM NAME:  MD-2SUBQ.BAS
'DESCRIPTION:   MD-2 QUICK-BASIC SUBROUTINES
'DOCUMENTATION: MD-2SUBQ.DOC
```

```
'PROGRAMMER:     Roger Arrick
'LANGUAGE:       QUICK-BASIC V4.0
'VERSION:        1.59
'EDIT DATE:      1/17/89
'EDIT SESSION:   59

'******************* INITIALIZE *******************
'
'INITIALIZE VARIABLES
'
md2.init:
        'DIMENSION ARRAYS
        'PUT THIS AT FRONT OF PROGRAM
        'MOVE FROM HERE IF NEEDED 'SET PORT ADDRESSES
        ADDR.12% = &H3BC        'MOTOR 1 & 2
        ADDR.34% = &H378        'MOTOR 3 & 4
        ADDR.56% = &H278        'MOTOR 5 & 6

'TURN OFF ALL PHASES OF ALL MOTORS
        OUT ADDR.12%, &HFF
        OUT ADDR.34%, &HFF
        OUT ADDR.56%, &HFF

'SET INITIAL MOVEMENT PARAMETERS
        move.action$ = "P"
        FOR i = 0 TO 6
                check.key$(i) = "Y"
                check.limit$(i) = "Y"
                current.position(i) = 0
                direction$(i) = "F"
                last.pattern%(i) = &HE
                power.down$(i) = "Y"
                speed%(i) = 0
                steps.to.move(i) = 0
                step.type$(i) = "H"
                target.position(i) = 0
        NEXT i
        RETURN '***************** MD-2 ON *****************
'
'TURN ON MOTOR DRIVER AND SET MOTOR PHASES OF MOTOR% TO LAST PATTERN
'IF ONLY ONE MOTOR SELECTED THEN THE OTHER MOTOR AT THAT PORT IS LEFT ALONE.
'
MD2.ON:
        IF motor% = 1 THEN
                OUT ADDR.12%, ((INP(ADDR.12%) AND &HF0) OR last.pattern%(1))
```

```
            END IF
            OUT ADDR.12% + 2, &HED
        IF motor% = 2 THEN
            OUT ADDR.12%, (((INP(ADDR.12%) AND &HF) OR (last.pattern%(2) * &H10))
            OUT ADDR.12% + 2, &HED
        END IF
        IF motor% = 3 THEN
            OUT ADDR.34%, (((INP(ADDR.34%) AND &HF0) OR last.pattern%(3))
            OUT ADDR.34% + 2, &HED
        END IF
        IF motor% = 4 THEN
            OUT ADDR.34%, (((INP(ADDR.34%) AND &HF) OR (last.pattern%(4) * &H10))
            OUT ADDR.34% + 2, &HED
        END IF
        IF motor% = 5 THEN
            OUT ADDR.56%, (((INP(ADDR.56%) AND &HF0) OR last.pattern%(5))
            OUT ADDR.56% + 2, &HED
        END IF
        IF motor% = 6 THEN
            OUT ADDR.56%, (((INP(ADDR.56%) AND &HF) OR (last.pattern%(6) * &H10))
            OUT ADDR.56% + 2, &HED
        END IF
        IF motor% = 12 THEN
            OUT ADDR.12%, ((last.pattern%(2) * &H10) OR last.pattern%(1))
            OUT ADDR.12% + 2, &HED
        END IF
        IF motor% = 34 THEN
            OUT ADDR.34%, ((last.pattern%(4) * &H10) OR last.pattern%(3))
            OUT ADDR.34% + 2, &HED
        END IF
        IF motor% = 56 THEN
            OUT ADDR.56%, ((last.pattern%(6) * &H10) OR last.pattern%(5))
            OUT ADDR.56% + 2, &HED
        END IF
RETURN '**************** MD-2 OFF ****************************
'
'TURN ON MOTOR DRIVER AND TURN OFF MOTOR PHASES OF MOTOR%
'IF ONLY ONE MOTOR SELECTED THEN THE OTHER MOTOR AT THAT PORT IS LEFT ALONE.
md2.off:
        IF motor% = 1 THEN
            OUT ADDR.12%, (((INP(ADDR.12%) AND &HF0) OR &HF)
            OUT ADDR.12% + 2, &HED
        END IF
        IF motor% = 2 THEN
            OUT ADDR.12%, (((INP(ADDR.12%) AND &HF) OR &HF0)
            OUT ADDR.12% + 2, &HED
        END IF
```

```
        IF motor% = 3 THEN
            OUT ADDR.34%, (((INP(ADDR.34%) AND &HF0) OR &HF)
            OUT ADDR.34% + 2, &HED
        END IF
        IF motor% = 4 THEN
            OUT ADDR.34%, (((INP(ADDR.34%) AND &HF) OR &HF0)
            OUT ADDR.34% + 2, &HED
        END IF
        IF motor% = 5 THEN
            OUT ADDR.56%, (((INP(ADDR.56%) AND &HF0) OR &HF)
            OUT ADDR.56% + 2, &HED
        END IF
        IF motor% = 6 THEN
            OUT ADDR.56%, (((INP(ADDR.56%) AND &HF) OR &HF0)
            OUT ADDR.56% + 2, &HED
        END IF
        IF motor% = 12 THEN
            OUT ADDR.12%, &HFF
            OUT ADDR.12% + 2, &HED
        END IF
        IF motor% = 34 THEN
            OUT ADDR.34%, &HFF
            OUT ADDR.34% + 2, &HED
        END IF
        IF motor% = 56 THEN
            OUT ADDR.56%, &HFF
            OUT ADDR.56% + 2, &HED
        END IF
        RETURN '****************** MD-2 MOVE ******************
'
'VARIABLES USED:
'ADDR.12%,34%,56%                MD-2 DRIVER ADDRESSES
'CHECK.KEYS(MOTOR%)              CHECK FOR KEYSTROKE, Y=YES,N=NO
'CHECK.LIMITS(MOTOR%)            CHECK FOR LIMIT SWITCH, Y=YES,N=NO
'CURRENT.POSITION(MOTOR%)        # OF STEPS FROM REVERSE LIMIT
'DIRECTIONS(MOTOR%)              F=FORWARD, R=REVERSE
'LAST.PATTERN%(MOTOR%)           LAST STEP PATTERN GIVEN
'MOVE.ACTIONS                    P-TO POSITION, S-# STEPS, C-CONTINUOUSLY
'MOTOR%                          MOTOR NUMBER 1-6,12,34,56
'POWER.DOWNS(MOTOR%)             POWER DOWN WHEN DONE Y=YES,N=NO
'RETURN.STATUS$                  RETURN STATUS, O=ok, K=keypressed, L=limit
'SPEED%(MOTOR%)                  MOTOR SPEED 0 - 32000, 0=FASTEST
'STEPS.TO.MOVE(MOTOR%)           # OF STEPS TO MOVE MOTOR
'STEP.TYPES(MOTOR%)              S=SINGLE, D=DOUBLE, H=HALF
'TARGET.POSITION(MOTOR%)         TARGET POSITION md2.move:
        'SET UP VARIABLES FOR MOVE.LOOP BASED ON MOTOR #
```

```
     IF motorX = 1 THEN
          aX = ADDR.12X: KS = check.keyS(1)
          DX = speedX(1): M1X = 1: M2X = 0
          GOTO MD2.LC
     END IF
     IF motorX = 2 THEN
          aX = ADDR.12X: KS = check.keyS(2)
          DX = speedX(2): M1X = 0: M2X = 2
          GOTO MD2.LC
     END IF
     IF motorX = 3 THEN
          aX = ADDR.34X: KS = check.keyS(3)
          DX = speedX(3): M1X = 3: M2X = 0
          GOTO MD2.LC
     END IF
     IF motorX = 4 THEN
          aX = ADDR.34X: KS = check.keyS(4)
          DX = speedX(4): M1X = 0: M2X = 4
          GOTO MD2.LC
     END IF
     IF motorX = 5 THEN
          aX = ADDR.56X: KS = check.keyS(5)
          DX = speedX(5): M1X = 5: M2X = 0
          GOTO MD2.LC
     END IF
     IF motorX = 6 THEN
          aX = ADDR.56X: KS = check.keyS(6)
          DX = speedX(6): M1X = 0: M2X = 6
          GOTO MD2.LC
     END IF
     IF motorX = 12 THEN
          aX = ADDR.12X: KS = check.keyS(1)
          DX = speedX(1): M1X = 1: M2X = 2
          GOTO MD2.LC
     END IF
     IF motorX = 34 THEN
          aX = ADDR.34X: KS = check.keyS(3)
          DX = speedX(3): M1X = 3: M2X = 4
          GOTO MD2.LC
     END IF
     IF motorX = 56 THEN
          aX = ADDR.56X: KS = check.keyS(5)
          DX = speedX(5): M1X = 5: M2X = 6
          GOTO MD2.LC
     END IF
MD2.LC:
     'SET LIMIT CHECKING
     IF M1X = 0 THEN L1S = "N" ELSE L1S = check.limitS(M1X)
     IF M2X = 0 THEN L2S = "N" ELSE L2S = check.limitS(M2X)

'SET POWER DOWN WHEN DONE
```

```
          IF M1% = 0 THEN P1$ = "N" ELSE P1$ = power.down$(M1%)
          IF M2% = 0 THEN P2$ = "N" ELSE P2$ = power.down$(M2%)

'SET STEP COUNT
IF move.action$ = "C" THEN
          IF M1% = 0 THEN S1& = 0 ELSE S1& = 8
          IF M2% = 0 THEN S2& = 0 ELSE S2& = 8
END IF
IF move.action$ = "S" THEN
          IF M1% = 0 THEN S1& = 0 ELSE S1& = steps.to.move(M1%)
          IF M2% = 0 THEN S2& = 0 ELSE S2& = steps.to.move(M2%)
END IF
IF move.action$ = "P" THEN
          IF M1% = 0 THEN
                    S1& = 0
          ELSE
                    S1& = target.position(M1%) - current.position(M1%)
                    IF S1& < 0 THEN
                              S1& = S1& * -1
                              direction$(M1%) = "R"
                    ELSE
                              direction$(M1%) = "F"
                    END IF
          END IF
          IF M2% = 0 THEN
                    S2& = 0
          ELSE
                    S2& = target.position(M2%) - current.position(M2%)
                    IF S2& < 0 THEN
                              S2& = S2& * -1
                              direction$(M2%) = "R"
                    ELSE
                              direction$(M2%) = "F"
                    END IF
          END IF
END IF 'CREATE STEP PATTERNS
step.type$ = step.type$(M2%)
M% = M2%
GOSUB GET.PATTERN
'PUT PATTERN IN HIGH NIBBLE
FOR i% = 1 TO 8
          pn%(i%) = p%(i%) * &H10
NEXT i%
step.type$ = step.type$(M1%)
M% = M1%
GOSUB GET.PATTERN
'PUT PATTERN IN LOW NIBBLE
FOR i% = 1 TO 8
          pn%(i%) = pn%(i%) OR p%(i%)
```

```
        NEXT i%
        'PUT NEW FOUND PATTERN IN P1%-P8%
        P1% = pn%(1): P2% = pn%(2): P3% = pn%(3): P4% = pn%(4)
        P5% = pn%(5): P6% = pn%(6): P7% = pn%(7): P8% = pn%(8)

'MOVE THE MOTORS!
        GOSUB MD2.MOVE.LOOP

'ADJUST POSITION VALUES
        IF move.action$ = "C" THEN RETURN
        IF M1% <> 0 THEN
            IF direction$(M1%) = "F" THEN
                current.position(M1%) = current.position(M1%) + S3&
            END IF
            IF direction$(M1%) = "R" THEN
                current.position(M1%) = current.position(M1%) - S3&
            END IF
        END IF
        IF M2% <> 0 THEN
            IF direction$(M2%) = "F" THEN
                current.position(M2%) = current.position(M2%) + S4&
            END IF
            IF direction$(M2%) = "R" THEN
                current.position(M2%) = current.position(M2%) - S4&
            END IF
        END IF
        END IF
        RETURN GET.PATTERN:
        'GET STEP PATTERN BASED ON STEP TYPE
        IF M% = 0 THEN
            FOR i = 1 TO 8
                p%(i) = &HF
            NEXT i
            RETURN
        END IF
        IF step.type$ = "H" THEN
            p%(1) = &HE: p%(2) = &HC: p%(3) = &HD: p%(4) = &H9
            p%(5) = &HB: p%(6) = &H3: p%(7) = &H7: p%(8) = &H6
        END IF
        IF step.type$ = "S" THEN
            p%(1) = &HE: p%(2) = &HD: p%(3) = &HB: p%(4) = &H7
            p%(5) = &HE: p%(6) = &HD: p%(7) = &HB: p%(8) = &H7
        END IF
        IF step.type$ = "D" THEN
            p%(1) = &HC: p%(2) = &HC: p%(3) = &H9: p%(4) = &H6
            p%(5) = &HC: p%(6) = &HC: p%(7) = &H9: p%(8) = &H6
        END IF
        'ADJUST FOR CORRECT DIRECTION
        IF direction$(M%) = "F" THEN
            SWAP p%(1), p%(8): SWAP p%(2), p%(7)
```

```
                        SWAP pX(3), pX(6): SWAP pX(4), pX(5)
        END IF
        'ADJUST FOR CORRECT STARTING PATTERN
        'RX = # OF TIMES TO ROTATE PATTERN
        IF last.patternX(MX) = pX(1) THEN RX = 1
        IF last.patternX(MX) = pX(2) THEN RX = 2
        IF last.patternX(MX) = pX(3) THEN RX = 3
        IF last.patternX(MX) = pX(4) THEN RX = 4
        IF last.patternX(MX) = pX(5) THEN RX = 5
        IF last.patternX(MX) = pX(6) THEN RX = 6
        IF last.patternX(MX) = pX(7) THEN RX = 7
        IF last.patternX(MX) = pX(8) THEN RX = 8
        IF last.patternX(MX) = 0 THEN RX = 8
        FOR iX = 1 TO RX
            pX = pX(1)
            pX(1) = pX(2): pX(2) = pX(3): pX(3) = pX(4): pX(4) = pX(5)
            pX(5) = pX(6): pX(6) = pX(7): pX(7) = pX(8): pX(8) = pX
        NEXT iX
        RETURN '**************** MD-2 MOVE LOOP ******************
'FAST MOVE LOOP THAT OUTPUTS STEP PATTERNS, COUNTS
'STEPS, CHECKS LIMIT SWITCHES AND KEYBOARD.

'p1X-p8X = STEP PATTERNS
'    AX  = DRIVER ADDRESS
'    KS  = CHECK FOR KEY PRESSED, Y=YES, N=NO
'    DX  = DELAY BETWEEN STEPS, 0=FAST
'    S1& = # OF STEPS TO MOVE FOR FIRST MOTOR, 0=NONE
'    S2& = # OF STEPS TO MOVE FOR SECOND MOTOR, 0=NONE
'    S3& = # OF STEPS COMPLETED ON FIRST MOTOR
'    S4& = # OF STEPS COMPLETED ON SECOND MOTOR
'    D1$ = FIRST MOTOR DONE?, Y=YES, N=NO
'    D2$ = SECOND MOTOR DONE?, Y=YES, N=NO
'    L1$ = CHECK FOR LIMIT SWITCHES, Y=YES, N=NO
'    L2$ = CHECK FOR LIMIT SWITCHES, Y=YES, N=NO
'    P1$ = POWER DOWN WHEN DONE, Y=YES, N=NO
'    P2$ = POWER DOWN WHEN DONE, Y=YES, N=NO

MD2.MOVE.LOOP:
        D1$ = "N": D2$ = "N": S3& = S1&: S4& = S2&: return.status$ = "O"

'CHECK FOR SPACE BAR TO EMERGENCY STOP MOTORS
ML1:    IF KS = "N" THEN GOTO ML2
        IF INKEY$ = " " THEN return.status$ = "K": GOSUB ML.STOP.1: GOSUB ML.STOP.2

'STEP 1
ML2:    'CHECK & UPDATE STEP COUNTS
        IF S1& = 0 THEN GOSUB ML.STOP.1
```

```
            S1& = S1& - 1
            IF S2& = 0 THEN GOSUB ML.STOP.2
            S2& = S2& - 1

'OUTPUT THE STEP PATERN
            OUT a%, P1%

'CHECK LIMIT SWITCHES
            IF L1$ = "Y" THEN IF (INP(a% + 1) AND &H20) = 0 THEN return.status$ = "L": GOSUB ML.STOP.1
            IF L2$ = "Y" THEN IF (INP(a% + 1) AND &H10) = 0 THEN return.status$ = "L": GOSUB ML.STOP.2

'DO DELAY LOOP FOR SPEED CONTROL
            IF D% = 0 THEN GOTO ML4
            i% = D%
   ML3:     i% = i% - 1
            IF i% <> 0 THEN GOTO ML3

'ADD TO STEP COUNT FOR CONTINOUS MOVEMENT
   ML4:     IF move.action$ = "C" THEN S1& = S1& + 8: S2& = S2& + 8

'STEP 2
            IF S1& = 0 THEN GOSUB ML.STOP.1
            S1& = S1& - 1
            IF S2& = 0 THEN GOSUB ML.STOP.2
            S2& = S2& - 1
            OUT a%, P2%
            IF L1$ = "Y" THEN IF (INP(a% + 1) AND &H20) = 0 THEN return.status$ = "L": GOSUB ML.STOP.1
            IF L2$ = "Y" THEN IF (INP(a% + 1) AND &H10) = 0 THEN return.status$ = "L": GOSUB ML.STOP.2
            IF D% = 0 THEN GOTO ML6
            i% = D%
   ML5:     i% = i% - 1
            IF i% <> 0 THEN GOTO ML5

'STEP 3
   ML6:     IF S1& = 0 THEN GOSUB ML.STOP.1
            S1& = S1& - 1
            IF S2& = 0 THEN GOSUB ML.STOP.2
            S2& = S2& - 1
            OUT a%, P3%
            IF D% = 0 THEN GOTO ML8
            i% = D%
   ML7:     i% = i% - 1
            IF i% <> 0 THEN GOTO ML7

'STEP 4
   ML8:     IF S1& = 0 THEN GOSUB ML.STOP.1
            S1& = S1& - 1
            IF S2& = 0 THEN GOSUB ML.STOP.2
            S2& = S2& - 1
            OUT a%, P4%
            IF L1$ = "Y" THEN IF (INP(a% + 1) AND &H20) = 0 THEN return.status$ = "L": GOSUB ML.STOP.1
```

```
ML9:       IF L2$ = "Y" THEN IF (INP(aX + 1) AND &H10) = 0 THEN return.status$ = "L": GOSUB ML.STOP.2
           IF DX = 0 THEN GOTO ML10
           iX = DX
           iX = iX - 1
           IF iX <> 0 THEN GOTO ML9

ML10:      'STEP 5
           IF S1& = 0 THEN GOSUB ML.STOP.1
           S1& = S1& - 1
           IF S2& = 0 THEN GOSUB ML.STOP.2
           S2& = S2& - 1
           OUT aX, P5%
           IF L1$ = "Y" THEN IF (INP(aX + 1) AND &H20) = 0 THEN return.status$ = "L": GOSUB ML.STOP.1
           IF L2$ = "Y" THEN IF (INP(aX + 1) AND &H10) = 0 THEN return.status$ = "L": GOSUB ML.STOP.2
           IF DX = 0 THEN GOTO ML12
           iX = DX
ML11:      iX = iX - 1
           IF iX <> 0 THEN GOTO ML11

ML12:      'STEP 6
           IF S1& = 0 THEN GOSUB ML.STOP.1
           S1& = S1& - 1
           IF S2& = 0 THEN GOSUB ML.STOP.2
           S2& = S2& - 1
           OUT aX, P6%
           IF L1$ = "Y" THEN IF (INP(aX + 1) AND &H20) = 0 THEN return.status$ = "L": GOSUB ML.STOP.1
           IF L2$ = "Y" THEN IF (INP(aX + 1) AND &H10) = 0 THEN return.status$ = "L": GOSUB ML.STOP.2
           IF DX = 0 THEN GOTO ML14
           iX = DX
ML13:      iX = iX - 1
           IF iX <> 0 THEN GOTO ML13

ML14:      'BOTH MOTORS DONE?
           IF D1$ = "Y" AND D2$ = "Y" THEN RETURN

'STEP 7
           IF S1& = 0 THEN GOSUB ML.STOP.1
           S1& = S1& - 1
           IF S2& = 0 THEN GOSUB ML.STOP.2
           S2& = S2& - 1
           OUT aX, P7%
           IF L1$ = "Y" THEN IF (INP(aX + 1) AND &H20) = 0 THEN return.status$ = "L": GOSUB ML.STOP.1
           IF L2$ = "Y" THEN IF (INP(aX + 1) AND &H10) = 0 THEN return.status$ = "L": GOSUB ML.STOP.2
           IF DX = 0 THEN GOTO ML16
           iX = DX
ML15:      iX = iX - 1
           IF iX <> 0 THEN GOTO ML15

ML16:      'STEP 8
           IF S1& = 0 THEN GOSUB ML.STOP.1
           S1& = S1& - 1
```

```
            IF S2& = 0 THEN GOSUB ML.STOP.2
            S2& = S2& - 1
            OUT a%, P8%
            IF L1$ = "Y" THEN IF (INP(a% + 1) AND &H20) = 0 THEN return.status$ = "L": GOSUB ML.STOP.1
            IF L2$ = "Y" THEN IF (INP(a% + 1) AND &H10) = 0 THEN return.status$ = "L": GOSUB ML.STOP.2
            IF D% = 0 THEN GOTO ML1
            i% = D%
ML17:       i% = i% - 1
            IF i% <> 0 THEN GOTO ML17

GOTO ML1

'MOTOR # 1 DONE
ML.STOP.1:
            IF D1$ = "Y" THEN RETURN
            IF (INP(a%) AND &HF) <> &HF THEN last.pattern%(M1%) = INP(a%) AND &HF
            'TURN POWER OFF MOTOR 1?
            IF P1$ = "Y" THEN
                    x% = (INP(a%) AND &HF)
                    P1% = ((P1% AND &HF0) OR x%)
                    P2% = ((P2% AND &HF0) OR x%)
                    P3% = ((P3% AND &HF0) OR x%)
                    P4% = ((P4% AND &HF0) OR x%)
                    P5% = ((P5% AND &HF0) OR x%)
                    P6% = ((P6% AND &HF0) OR x%)
                    P7% = ((P7% AND &HF0) OR x%)
                    P8% = ((P8% AND &HF0) OR x%)
            ELSE
            'SET CURRENT MOTOR 1 PATTERN IN ALL P%'S
                    P1% = P1% OR &HF
                    P2% = P2% OR &HF
                    P3% = P3% OR &HF
                    P4% = P4% OR &HF
                    P5% = P5% OR &HF
                    P6% = P6% OR &HF
                    P7% = P7% OR &HF
                    P8% = P8% OR &HF
            END IF
            D1$ = "Y": L1$ = "N": S3& = S3& - S1&
            RETURN 'MOTOR # 2 DONE
ML.STOP.2:
            IF D2$ = "Y" THEN RETURN
            IF (INP(a%) AND &HF0) <> &HF0 THEN last.pattern%(M2%) = (INP(a%) AND &HF0) / &H10
            'TURN POWER OFF MOTOR 2?
            IF P2$ = "Y" THEN
                    P1% = P1% OR &HF0
                    P2% = P2% OR &HF0
                    P3% = P3% OR &HF0
```

```
                    P4% = P4% OR &HF0
                    P5% = P5% OR &HF0
                    P6% = P6% OR &HF0
                    P7% = P7% OR &HF0
                    P8% = P8% OR &HF0
         ELSE
                    x% = (INP(a%) AND &HF0)
                    P1% = ((P1% AND &HF) OR x%)
                    P2% = ((P2% AND &HF) OR x%)
                    P3% = ((P3% AND &HF) OR x%)
                    P4% = ((P4% AND &HF) OR x%)
                    P5% = ((P5% AND &HF) OR x%)
                    P6% = ((P6% AND &HF) OR x%)
                    P7% = ((P7% AND &HF) OR x%)
                    P8% = ((P8% AND &HF) OR x%)
         END IF
         D2$ = "Y": L2$ = "N": S4& = S4& - S2&
RETURN

END
RETURN
```

```
'************************************************************
'************************************************************
'******                                                 ******
'******       Interferometric Measuring Device Analyzer ******
'******                    Version 2                    ******
'******                                                 ******
'******       Written by: Robert Wagner      7-21-89    ******
'******                   Modified: 7-22-91             ******
'******                                                 ******
'************************************************************
'************************************************************

DECLARE SUB checkfile (path$, name$, extension$, okay$, current.slice, slice, type$, save.date$, finish)
DECLARE FUNCTION spline! (numpeaks%, peakdom!(), peakran!(), incout!, errtol, spline.name$, spline.path$, current.slice!, slice, okay$, xaxismin, xaxismax, yaxismax, scr, spline.exten$, length, scan.start, scan.end, finish, numout, outdom(), funcval(), max.thickness)
        yaxismin, '-------- declare common variables --------
COMMON tube.path$, tube.name$, save.tube$, peak.path$, peak.name$, save.peak$
COMMON spline.path$, spline.name$, save.spline$, volume.path$, volume.name$
COMMON save.volume$, config.path$, config.name$, save.config$, slice
COMMON number, dist.interval, step.interval, type.tube$, scan.start, scan.end
COMMON length, motor.port$, translator, rotator, tran.speed, rot.speed
COMMON tran.rev, rot.rev, screw.rev, sample, timer.rate, n1, n2, timer.freq
COMMON low.scan, high.scan, io.add, interrupt, dma.level, thickness, errtol
COMMON incout, max.pk.wid, min.pk.wid, pos.thresh, neg.thresh, max.consec
COMMON min.plateau, move.average, find.peak$, printer.port$
COMMON scrtype$, key.break$, scr, alum.start, alum.end, alum.length
COMMON steel.start, steel.end, steel.length, base.path$, base.name$
```

```
COMMON tube.extent$, peak.extent$, spline.extent$, volume.extent$, config.extent$
COMMON already.running$, xaxismin, xaxismax, yaxismin, yaxismax, ticky, marky
COMMON current.menu$, max.number, max.slices, max.sample, program.version

'$DYNAMIC

'---------------- variables ----------------

DIM menu.color(10)                          'used in menu routines
    DIM xcurs(1 TO 200)  AS INTEGER             'horizontal cursor image
    DIM ycurs(1 TO 650)  AS INTEGER             'vertical cursor image
    DIM plus(1 TO 20) AS INTEGER                'plus sign image
    DIM minus(1 TO 20) AS INTEGER               'minus sign image
    DIM equal(1 TO 20) AS INTEGER               'equal sign image DIM domain(1)                               'domain of tube data
    DIM range(1)                                'range of tube data
    DIM peaks(1)                                'type of peak at each tube data point
    DIM first(1)                                'first derivative of scanned data
    DIM peak.pos.max(1, 2)                      'location and value of maximas in peak recognition
    DIM peak.pos.min(1, 2)                      'location and value of minimas in peak recognition
    DIM smooth(1)                               'smoothed values of tube data
    DIM scalsmooth(1)                           'scaled smoothed values of tube data for plot DIM scaldom(1)                              'scaled domain of tube data for plot
    DIM scalran(1)                              'scaled range of tube data for plot
    DIM peakdom(1)                              'position of peak
    DIM peakran(1)                              'thickness of peak
    DIM splinevol(number)                       'volume of individual slices
    DIM loaded.dom(1)                           'domain of loaded peak file
    DIM loaded.ran(1)                           'range of loaded peak file
    DIM outdom(1)                               'domain of spline fit data
    DIM funcval(1)                              'range of spline fit data called.from.markings$ = "n"                 'variable to determine when config menu is called
    print.smooth$ = "n"                         'variable to display/not display smoothed data
    old.analysis$ = "n"                         'variable to allow user to look at old analysis
    selected.option$ = "start"                  'no options selected yet ON ERROR GOTO error.handler '------- check to see if this program was called or run directly -------

IF already.running$ <> "y" THEN
        CLS
        LOCATE 12
        PRINT TAB(23); "Please run the NRL-IMD program first."
        PRINT
        PRINT TAB(24); "This program is called from NRL-IMD."
        END
    END IF
```

```
'--------------- main program ---------------

GOSUB analyze

DO
        LOOP

END
'--------------- subroutines --------------- error.handler:
    SELECT CASE ERR                         'handles all errors
        CASE 53                             'file not found error
            okay$ = "n"
            CLOSE
            RESUME NEXT
        CASE 61                             'disk full error
            BEEP
            CLS
            LOCATE 12
            PRINT TAB(28); "The Current Disk is Full"
            PRINT
            PRINT TAB(19); "press any key to return to the main menu ";
            zz$ = INPUT$(1)
            CLOSE
            current.menu$ = "main"
            CHAIN "NRL-IMD"
        CASE 76                             'path not found error
            BEEP
            CLS
            LOCATE 12
            PRINT TAB(22); "Invalid Path Specified for Data File"
            PRINT
            PRINT TAB(22); "press any key to return to main menu"
            zz$ = INPUT$(1)
            CLOSE
            current.menu$ = "main"
            CHAIN "NRL-IMD"
        CASE ELSE
            PRINT
            PRINT
            PRINT TAB(20); "Error "; ERR; " has caused the program to abort."
            PRINT
            PRINT TAB(22); "Press any key to return to main menu"
            zz$ = INPUT$(1)
            CLOSE
            SCREEN 0
            current.menu$ = "main"
            CHAIN "NRL-IMD"
    END SELECT
```

```
keys.off:
        FOR x = 1 TO 25
                KEY(x) OFF                                      'turns off all key-trapping
        NEXT x
        RETURN anal.keys.on:
        FOR y = 10 TO 23
                KEY(y) ON                                       'turn key trapping back on
        NEXT y
        FOR y = 1 TO 6
                KEY(y) ON
        NEXT y
        KEY(25) ON
        RETURN print.pos:
        LOCATE 23, 18
        PRINT USING "x pos: ###.###"; CLNG(1000 * domain(coord)) / 1000;
        PRINT TAB(38); USING "y pos: ####.#"; CLNG(10 * range(coord)) / 10;
        PRINT TAB(58); "slice: "; current.slice
        RETURN
menu.quit:
        GOSUB keys.off                                          'turn off keys
        CLOSE                                                   'close all files PRINT
        PRINT TAB(21); "Are you sure you want to quit (Y/N)? ";
        leave$ = UCASE$(INPUT$(1))
        PRINT leave$
        IF leave$ = "Y" THEN END
        RETURN main.menu:
        current.menu$ = "main"
        CHAIN "NRL-IMD"                                         'return to main menu in NRL-IMD
        RETURN '--------------- analyzing menu ---------------
'---------------------------------------------- analyze:
        GOSUB analyze.menu.init                                 'set up all key trapping definitions
        GOSUB analyze.menu.on                                   'turn key trapping on
        GOSUB analyze.menu                                      'goto analyzing menu
        RETURN analyze.menu.init:
```

```
KEY 15, CHR$(160) + CHR$(72)          'up--up
KEY 16, CHR$(160) + CHR$(75)          'left--up
KEY 17, CHR$(160) + CHR$(77)          'right-down
KEY 18, CHR$(160) + CHR$(80)          'down--down
KEY 19, CHR$(32) + CHR$(28)           'RET--change
KEY 25, CHR$(32) + CHR$(1)            'ESC--quit ON KEY(1) GOSUB main.menu             'F1--goto main menu in NRL-IMD
ON KEY(2) GOSUB peak                  'data smoothing/peak recognition config menu
ON KEY(11) GOSUB a.up                 'up(cursor)--up
ON KEY(12) GOSUB a.up                 'left(cursor)--up
ON KEY(15) GOSUB a.up                 'up(keypad)--up
ON KEY(16) GOSUB a.up                 'left(keypad)--up
ON KEY(13) GOSUB a.down               'right(cursor)--down
ON KEY(14) GOSUB a.down               'down(cursor)--down
ON KEY(17) GOSUB a.down               'right(keypad)--down
ON KEY(18) GOSUB a.down               'down(keypad)--down
ON KEY(19) GOSUB a.change             'RET--goto routine to select item
ON KEY(25) GOSUB a.quit               'ESC--goto quit routine FOR x = 1 TO 5                        'set all the menu items to non-selected (low intensity white)
    menu.color(x) = 7
NEXT x
menu.color(1) = 15                    'set the 1st menu item to selected (high-intensity white)
a.menu.pos = 1                        'put the "cursor" at the 1st menu item
RETURN analyze.menu.on:                      'turns on the key-trapping for the analysis menu
    FOR x = 11 TO 19
        KEY(x) ON
    NEXT x
    KEY(1) ON
    KEY(2) ON
    KEY(25) ON
RETURN analyze.menu:                         'prints the analysis menu with currently selected menu item
CLS
PRINT TAB(32); "Analyze JFTOT Tube"
PRINT "---------------------------------------------------------"
PRINT
PRINT
PRINT
COLOR menu.color(1): PRINT TAB(25); "Analyze an Entire Tube"
COLOR menu.color(2): PRINT TAB(25); "Analyze a Range of Slices on a Tube"
COLOR menu.color(3): PRINT TAB(25); "Analyze a Single Slice"
PRINT
COLOR menu.color(4): PRINT TAB(25); "Generate New Volume Report"
PRINT
COLOR menu.color(5): PRINT TAB(25); "Peak Recognition Mode";
COLOR 7
SELECT CASE find.peak$
```

```
            CASE "a"
                    PRINT TAB(55); "Automatic Peak Marking"
            CASE "c"
                    PRINT TAB(55); "User Confirmation"
            CASE "m"
                    PRINT TAB(55); "Manually Mark"
        END SELECT
        PRINT
        PRINT
        PRINT TAB(15); "F1-Main Menu   F2-Smooth/Peak Config Menu   ESC-Quit"
    RETURN a.quit:
        GOSUB menu.quit                         'allows user to quit
        GOSUB analyze.menu.on                   'otherwise turn key-trapping back on
        GOSUB analyze.menu                      'reprint analysis menu
    RETURN a.up:
        IF a.menu.pos = 1 THEN                  'move "cursor" up one item
                a.menu.pos = 5                  'if "cursor" is at the top, move it to the bottom
                menu.color(1) = 7
        ELSE
                a.menu.pos = a.menu.pos - 1     'if "cursor" is anywhere else, move it up one
                menu.color(a.menu.pos + 1) = 7
        END IF
        menu.color(a.menu.pos) = 15             'hilight new menu item
        GOSUB analyze.menu                      'reprint analysis menu
    RETURN a.down:
        IF a.menu.pos = 5 THEN                  'move "cursor" down one item
                a.menu.pos = 1                  'if "cursor" at the bottom, move it to the top
                menu.color(5) = 7
        ELSE
                a.menu.pos = a.menu.pos + 1     'if "cursor" is anywhere else, move it down one
                menu.color(a.menu.pos - 1) = 7
        END IF
        menu.color(a.menu.pos) = 15             'hilight new menu item
        GOSUB analyze.menu                      'reprint analysis menu
    RETURN a.change:
        GOSUB keys.off                          'when user selects a menu item, do whatever
        SELECT CASE a.menu.pos
            CASE 1                              'analyze entire tube
                start = 1                       'begin scan with first slice
                finish = slice                  'end scan with last slice
                GOSUB analyze.tube
            CASE 2                              'analyze a range of slices
                LOCATE 21
```

```
        COLOR 15
        PRINT TAB(22); "analyze a range of slices on this tube"
        PRINT TAB(27); "start - ";
        COLOR 7
        INPUT "", srt$
        COLOR 15
        LOCATE 22, 44
        PRINT "end - ";
        COLOR 7
        INPUT "", fsh$
        srt = INT(VAL(srt$))
        fsh = INT(VAL(fsh$))
        IF srt > 0 AND srt <= fsh AND fsh <= slice THEN
            start = srt                         'begin analysis with slice start
            finish = fsh                        'end analysis with slice end
            GOSUB analyze.tube
        ELSE
            BEEP
        END IF
CASE 3
        LOCATE 21
        COLOR 15
        PRINT TAB(24); "analyze which slice on this tube: ";
        COLOR 7
        INPUT "", srt$
        srt = INT(VAL(srt$))
        IF srt > 0 AND srt <= slice THEN
            start = srt
            finish = srt                        'analyze one slice
            GOSUB analyze.tube
        ELSE
            BEEP
        END IF
CASE 4  GOSUB volume.report                     'recalcuate total volume of tube
CASE 5. LOCATE 22
        COLOR 15
        PRINT "Automatically Mark Peaks, Auto Mark w/User Confirm, or Manually Mark (A/C/M)  ";
        COLOR 7
        DO
            LOCATE 22, 78
            fd.pk$ = UCASE$(INPUT$(1))
            exit$ = "y"
            SELECT CASE fd.pk$
                CASE "A"
                            find.peak$ = "a"    'automatic
                CASE "C"
                            find.peak$ = "c"    'user confirmed
                CASE "M"
                            find.peak$ = "m"    'manual
```

```
                    CASE CHR$(13)
                    CASE ELSE
                        exits = "n"
            END SELECT
        LOOP UNTIL exits = "n"
    END SELECT
    IF a.menu.pos < 5 THEN
        GOSUB analyze
    ELSE
        GOSUB analyze.menu.on              'otherwise turn key-trapping back on
        GOSUB analyze.menu                 'reprint analysis menu
    END IF
RETURN '----------- data smoothing/peak recognition configuration menu -----------
'------------------------------------------------------------------------- peak:
    SCREEN 0
    current.menu$ = "peak"                 'set current menu to peak
    GOSUB keys.off                         'turn off key trapping
    GOSUB peak.menu.init                   'initialize peak key trapping
    GOSUB peak.menu.on                     'turn on key trapping
    GOSUB peak.menu                        'display peak menu
RETURN peak.menu.init:

KEY 15, CHR$(160) + CHR$(72)           'up--up
    KEY 16, CHR$(160) + CHR$(75)           'left--up
    KEY 17, CHR$(160) + CHR$(77)           'right-down
    KEY 18, CHR$(160) + CHR$(80)           'down--down
    KEY 19, CHR$(32) + CHR$(28)            'RET-change
    KEY 25, CHR$(32) + CHR$(1)             'ESC-quit IF called.from.marking$ = "y" THEN
        ON KEY(1) GOSUB return.to.marking
    ELSE
        ON KEY(1) GOSUB analyze            'F1--goto analysis menu
    END IF
    ON KEY(11) GOSUB p.up                  'up(cursor)--move up one menu item
    ON KEY(12) GOSUB p.up                  'left(cursor)--move up one menu item
    ON KEY(15) GOSUB p.up                  'up(keypad)--move up one menu item
    ON KEY(16) GOSUB p.up                  'left(keypad)--move up one menu item
    ON KEY(13) GOSUB p.down                'right(cursor)--move down one menu item
    ON KEY(14) GOSUB p.down                'down(cursor)--move down one menu item
    ON KEY(17) GOSUB p.down                'right(keypad)--move down one menu item
    ON KEY(18) GOSUB p.down                'down(keypad)--move down one menu item
    ON KEY(19) GOSUB p.change              'RET--select menu item
    ON KEY(25) GOSUB p.quit                'ESC--quit program
```

```
        FOR x = 1 TO 7                              'deselect menu items (low intensity white)
            menu.color(x) = 7
        NEXT x
        menu.color(1) = 15                          'hilight 1st menu item (high intensity white)
        menu.pos = 1                                'set position to 1st menu item
RETURN peak.menu.on:
        FOR x = 11 TO 19                            'turn key trapping on
            KEY(x) ON
        NEXT x
        KEY(1) ON
        KEY(25) ON
RETURN peak.menu:                                          'display peak menu
        CLS
        PRINT TAB(15); "Data Smoothing/Peak Recognition Configuration Menu"
        PRINT "------------------------------------------------------------------------"
        PRINT
        PRINT "Peak Recognition Variables"
        COLOR menu.color(1): PRINT TAB(10); "Minimum Peak Width";
        COLOR 7: PRINT TAB(65); min.pk.wid; " mm";
        COLOR menu.color(2): PRINT TAB(10); "Maximum Peak Width ";
        COLOR 7: PRINT TAB(65); max.pk.wid; " mm"
        COLOR menu.color(3): PRINT TAB(10); "Positive Peak Threshold";
        COLOR 7: PRINT TAB(65); pos.thresh
        COLOR menu.color(4): PRINT TAB(10); "Negative Peak Threshold";
        COLOR 7: PRINT TAB(65); neg.thresh
        COLOR menu.color(5): PRINT TAB(10); "Maximum Consecutive Points to Establish Peak";
        COLOR 7: PRINT TAB(65); max.consec
        PRINT
        COLOR menu.color(6): PRINT TAB(10); "Minimum Width to Indicate a Plateau";
        COLOR 7: PRINT TAB(65); min.plateau; " mm"
        COLOR menu.color(7): PRINT TAB(10); "Number of Points in Moving Average to Smooth Data";
        COLOR 7: PRINT TAB(65); move.average
        PRINT
        IF called.from.marking$ = "y" THEN
            PRINT TAB(28); "F1-Find Peaks     ESC-Quit"
        ELSE
            PRINT TAB(27); "F1-Analysis Menu   ESC-Quit"
        END IF
RETURN p.quit:                                             'exit select or program
        GOSUB menu.quit                             'exit program
        GOSUB peak.menu.on                          'otherwise turn key trapping on
        GOSUB peak.menu                             'display peak menu
RETURN
```

```
return.to.marking:
    quit$ = "true"
    RETURN p.up:                                                       'move up one menu item
        IF menu.pos = 1 THEN
                menu.pos = 7
                menu.color(1) = 7
        ELSE
                menu.pos = menu.pos - 1
                menu.color(menu.pos + 1) = 7
        END IF
        menu.color(menu.pos) = 15
        GOSUB peak.menu
    RETURN p.down:                                                     'move down one menu item
        IF menu.pos = 7 THEN
                menu.pos = 1
                menu.color(7) = 7
        ELSE
                menu.pos = menu.pos + 1
                menu.color(menu.pos - 1) = 7
        END IF
        menu.color(menu.pos) = 15
        GOSUB peak.menu
    RETURN p.change:                                                   'select menu item
        GOSUB keys.off
        SELECT CASE menu.pos
                CASE 1
                        COLOR 15
                        LOCATE 22
                        PRINT TAB(21); "set minimum width of a peak (in mm) ";
                        COLOR 7
                        INPUT "", min.wid$
                        min.wid = ABS(VAL(min.wid$))
                        IF min.wid > 0 THEN min.pk.wid = min.wid
                CASE 2
                        COLOR 15
                        LOCATE 22
                        PRINT TAB(21); "set maximum width of a peak (in mm) ";
                        COLOR 7
                        INPUT "", max.wid$
                        max.wid = ABS(VAL(max.wid$))
                        IF max.wid > 0 THEN max.pk.wid = max.wid
                CASE 3
                        COLOR 15
                        LOCATE 22
                        PRINT TAB(28); "set positive threshold ";
```

```
                COLOR 7
                INPUT "", pos.trg$
                pos.trg = ABS(VAL(pos.trg$))
                IF pos.trg > 0 THEN pos.thresh = pos.trg
        CASE 4
                COLOR 15
                LOCATE 22
                PRINT TAB(28); "set negative threshold ";
                COLOR 7
                INPUT "", neg.trg$
                neg.thresh = VAL(neg.trg$)
        CASE 5
                COLOR 15
                LOCATE 22
                PRINT TAB(21); "set maximum consecutive points ";
                COLOR 7
                INPUT "", max.con$
                max.con = ABS(VAL(max.con$))
                IF max.con > 0 THEN max.consec = max.con
        CASE 6
                COLOR 15
                LOCATE 22
                PRINT TAB(16); "set minimum width (in mm) to indicate a plateau ";
                COLOR 7
                INPUT "", min.plt$
                min.plt = ABS(VAL(min.plt$))
                IF min.plt > 0 THEN min.plateau = min.plt
        CASE 7
                COLOR 15
                LOCATE 22
                PRINT TAB(20); "set number of points in moving average ";
                COLOR 7
                INPUT "", mov.avg$
                mov.avg = ABS(VAL(mov.avg$))
                IF mov.avg > 0 THEN move.average = mov.avg
        END SELECT
        GOSUB peak.menu.on
        GOSUB peak.menu
RETURN '--------------- option menu ---------------
' options:
        GOSUB option.menu.init          'set-up options menu after scanning
        GOSUB option.menu.on            'initialize keys for key trapping
        GOSUB option.menu               'turn key trapping on
                                        'print option menu
RETURN
```

```
option.menu.init:                                   'initialize keys for option menu KEY 15, CHR$(160) + CHR$(72)                'up--up
        KEY 16, CHR$(160) + CHR$(75)                'left--up
        KEY 17, CHR$(160) + CHR$(77)                'right-down
        KEY 18, CHR$(160) + CHR$(80)                'down--down
        KEY 19, CHR$(32) + CHR$(28)                 'RET-change
        KEY 25, CHR$(32) + CHR$(1)                  'ESC-quit ON KEY(11) GOSUB o.up                       'up(cursor)--up
        ON KEY(12) GOSUB o.up                       'left(cursor)--up
        ON KEY(15) GOSUB o.up                       'up(keypad)--up
        ON KEY(16) GOSUB o.up                       'left(keypad)--up
        ON KEY(13) GOSUB o.down                     'right(cursor)--down
        ON KEY(14) GOSUB o.down                     'down(cursor)--down
        ON KEY(17) GOSUB o.down                     'right(keypad)--down
        ON KEY(18) GOSUB o.down                     'down(keypad)--down
        ON KEY(19) GOSUB o.change                   'RET--select menu item
        ON KEY(25) GOSUB o.quit                     'ESC--return to analysis menu FOR x = 1 TO 5                              'deselect all menu items (low intensity white)
            menu.color(x) = 7
        NEXT x
        menu.color(1) = 15                          'hilight 1st menu item (high intensity white)
        menu.pos = 1                                'set cursor at 1st menu item
RETURN option.menu.on:
        FOR x = 11 TO 19                            'turn on key trapping
            KEY(x) ON
        NEXT x
        KEY(25) ON
RETURN option.menu:                                        'print option menu
        CLS
        PRINT TAB(29); "Analyzing Options Menu"
        PRINT "--------------------------------------------------------------------------"
        PRINT
        PRINT
        PRINT
        COLOR menu.color(1): PRINT TAB(25); "Display Scanned Data and Remark Peaks"
        COLOR menu.color(2): PRINT TAB(25); "Show Table of Marked Peaks"
        COLOR menu.color(3): PRINT TAB(25); "Display Thickness Profile"
        PRINT
        COLOR menu.color(4): PRINT TAB(25); "Analyze Next Slice"
        COLOR menu.color(5): PRINT TAB(25); "Return to Analysis Menu"
        COLOR 7
RETURN o.quit:
```

```
        GOSUB menu.quit            'return to analysis menu
        GOSUB option.menu.on       'otherwise turn key trapping back on
        GOSUB option.menu          'reprint option menu
    RETURN o.up:
        IF menu.pos = 1 THEN       'move "cursor" up one item
            menu.pos = 5
            menu.color(1) = 7
        ELSE
            menu.pos = menu.pos - 1
            menu.color(menu.pos + 1) = 7
        END IF
        menu.color(menu.pos) = 15
        GOSUB option.menu
    RETURN o.down:
        IF menu.pos = 5 THEN       'move "cursor" down one item
            menu.pos = 1
            menu.color(5) = 7
        ELSE
            menu.pos = menu.pos + 1
            menu.color(menu.pos - 1) = 7
        END IF
        menu.color(menu.pos) = 15
        GOSUB option.menu
    RETURN o.change:
        GOSUB keys.off
        SELECT CASE menu.pos       'do whatever user selects
            CASE 1
                selected.option$ = "remark"   'remark scanned data
            CASE 2
                GOSUB print.peaks             'display all the marked peaks
                GOSUB option.menu.on
                GOSUB option.menu
            CASE 3
                GOSUB plot.thick              'display the thickness profile for that slice
                GOSUB option.menu.on
                GOSUB option.menu
            CASE 4
                selected.option$ = "continue" 'go on to next slice
            CASE 5
                selected.option$ = "analysis menu"  'return to analysis menu
        END SELECT
    RETURN
``` analyze.tube:

```
'------------ analyze tubes ------------

'------------ set-up initial parameters ------------

' defines graphics shapes that are used in the peak
' marking section and sets the screen parameters ' this creates the x and y lines and the plus, minus, and equal signs '------------ create cursor and axes ------------
      SCREEN scr                                                    'turn on selected graphics screen
      CLS LINE (0, yaxismin)-(0, yaxismax), 14
      LINE (0, ticky)-(0, ticky + 2), 14
      GET (0, yaxismin)-(0, ticky + 2), ycurs        'vertical cursor
      LINE (xaxismin, 0)-(xaxismax, 0), 14
      GET (xaxismin, 0)-(xaxismax, 0), xcurs         'horizontal cursor
      LINE (12, 10)-(12, 14), 11
      LINE (10, 12)-(14, 12), 11
      GET (10, 10)-(14, 14), plus                    'plus sign
      GET (10, 12)-(14, 12), minus                   'minus sign
      LINE (20, 21)-(24, 21), 11
      LINE (20, 23)-(24, 23), 11
      GET (20, 20)-(24, 24), equal                   'equal sign SCREEN 0                                       'turn on text screen FOR current.slice = start TO finish                  'analyze from beginning slice to ending slice CLS
      numpeaks% = 0                                  'set the number of marked peaks to zero
      status = 0                                     'set the difference between increasing and decreasing peaks to zero
      old.analysis$ = "n"                            'set-up for a new slice
      print.smooth$ = "n"
      selected.option$ = "start"

'------------ load data from data file ------------

' loads raw data to be used from disk
' this routine loads the data from the tube into memory '------------ load data ------------
      quit$ = "n"
      DO
                                    LOCATE 13
```

```
                    PRINT TAB(32); "Loading slice "; current.slice
                    PRINT
     okay$ = "y"

IF current.slice = 100 THEN
           OPEN tube.path$ + tube.name$ + "00" + tube.exten$ FOR INPUT AS #1
     ELSE
           OPEN tube.path$ + tube.name$ + LTRIM$(STR$(current.slice)) + tube.exten$ FOR INPUT AS #1
     END IF IF okay$ = "y" THEN                                              'if data file was found, load data
        '---------- load in data -----------------
        quit$ = "y"
        INPUT #1, file.version$, file.date$                           'load in program version and date
        INPUT #1, number                                              'load in number of scanned data points
        REDIM domain(number), range(number), peaks(number)            'setup data arrays
        INPUT #1, domain(1), range(1)                                 'make initial guess at min and max values
        maxran = range(1)
        minran = range(1)

'---------- load data and find min and max range -----------
        FOR y = 2 TO number
            INPUT #1, domain(y), range(y)
            IF range(y) > maxran THEN maxran = range(y)               'load rest of data
            IF range(y) < minran THEN minran = range(y)               'recheck for min and max values NEXT y
        CLOSE ELSE   exit$ = "n"                                               'if data file wasn't found, indicate error
            BEEP
            DO
               CLS
               LOCATE 12
               PRINT TAB(28); "Tube data file not found"
               PRINT
               PRINT TAB(20); "T)ry again or R)eturn to analysis menu ";
               x$ = UCASE$(INPUT$(1))
               PRINT x$
               SELECT CASE x$
                     CASE "R"
                           RETURN
                     CASE "T"
                           exit$ = "y"
                           quit$ = "n"
                     CASE ELSE
                           exit$ = "n"
               END SELECT
            LOOP UNTIL exit$ = "y"
     END IF
LOOP UNTIL quit$ = "y"
```

```
'--------- check to see if this is an old analysis and peak file exists ----------
     okay$ = "y"

IF current.slice = 100 THEN
        OPEN peak.path$ + peak.name$ + "00" + peak.exten$ FOR INPUT AS #1
     ELSE
        OPEN peak.path$ + peak.name$ + LTRIM$(STR$(current.slice)) + peak.exten$ FOR INPUT AS #1
     END IF IF (okay$ = "n" AND find.peaks = "c") OR find.peaks = "a" THEN      'if .PK file doesn't exist and user confirmed marking is selected
        GOSUB auto.find.peaks                                            ' or auto marking is selected then let the computer find peaks
     ELSEIF okay$ = "y" AND find.peaks = "c" THEN                        'if .PK file exists and user confirmed marking is selected,
        PRINT                                                            ' check to remark or use old analysis
        PRINT TAB(22); "This Slice Has Already Been Analyzed."
        PRINT TAB(12); "Use Old Analysis or Automatically Find New Peaks? (O/N) ";
        DO
           LOCATE 14, 72
           zz$ = UCASE$(INPUT$(1))
           IF zz$ = "O" OR zz$ = "N" THEN EXIT DO
        LOOP IF zz$ = "N" THEN
           CLOSE
           GOSUB auto.find.peaks
        ELSE
           '---------- load in peak data ---------
           CLS
           LOCATE 13
           PRINT TAB(30); "Loading Old Analysis"
           INPUT #1, file.version$, file.date$
           INPUT #1, dummy, numpeaks%
           REDIM loaded.dom(numpeaks% + 1), loaded.ran(numpeaks% + 1)    'load peaks into a temporary array
           FOR y = 1 TO numpeaks%
              INPUT #1, loaded.dom(y)
              INPUT #1, loaded.ran(y)
           NEXT y
           CLOSE
           old.analysis$ = "y"

'----------- place loaded peaks into current peak array ------------
           z = 1
           FOR y = 1 TO number
              IF domain(y) = loaded.dom(z) THEN
                 IF (loaded.ran(z) > loaded.ran(z - 1) THEN              'increasing peak
                    peaks(y) = 1
                    status = status + 1
                 ELSEIF loaded.ran(z) = loaded.ran(z - 1) THEN           'equal peak
                    peaks(y) = 2
                 ELSEIF loaded.ran(z) < loaded.ran(z - 1) THEN           'decreasing peak
                    peaks(y) = -1
                    status = status - 1
```

```
            END IF
            z = z + 1
         NEXT y
      END IF
   ELSEIF okay$ = "y" AND find.peak$ = "m" THEN
      '----------- load in peak data ----------
      CLS
      LOCATE 13
      PRINT TAB(30); "Loading Old Analysis"
      INPUT #1, file.version$, file.date$
      INPUT #1, dummy, numpeaks%
      REDIM loaded.dom(numpeaks% + 1), loaded.ran(numpeaks% + 1)      'load peaks into a temporary array
      FOR y = 1 TO numpeaks%
         INPUT #1, loaded.dom(y)
         INPUT #1, loaded.ran(y)
      NEXT y
      CLOSE
      old.analysis$ = "y"

'---------- place loaded peaks into current peak array ----------
      z = 1
      FOR y = 1 TO number
         IF domain(y) = loaded.dom(z) THEN
            IF loaded.ran(z) > loaded.ran(z - 1) THEN            'increasing peak
               peaks(y) = 1
               status = status + 1
            ELSEIF loaded.ran(z) = loaded.ran(z - 1) THEN        'equal peak
               peaks(y) = 2
            ELSEIF loaded.ran(z) < loaded.ran(z - 1) THEN        'decreasing peak
               peaks(y) = -1
               status = status - 1
            END IF
            z = z + 1
         END IF
      NEXT y
   END IF
   CLOSE '---------- find/mark peaks to obtain volume ----------
IF find.peak$ <> "a" THEN                                'if user confirmed/manual marking is selected, then display data
   DO
      plot.start = 0              'display all data -- leftmost point 0 mm
      plot.end = length           '                    -- rightmost point length mm
      plot.length = length        'length of display is length of tube
      plot.start.num = 1          'first diplayed point is first data point
      plot.end.num = number       'last displayed point is last data point
      plot.max = maxran           'maximum intensity in displayed range is maximum intensity of all data points
      plot.min = minran           'minimum intensity in displayed range is minimum intensity of all data points
```

```
        GOSUB plot.data
        GOSUB mark.peaks                     'goto peak marking routine IF selected.options$ = "analysis menu" THEN
            SCREEN 0
            RETURN
        END IF
        IF selected.options$ = "F1" THEN
            GOSUB translate
            GOSUB calc.volume
            GOSUB options
            DO
                IF selected.options$ = "remark" OR selected.options$ = "continue" OR selected.options$ = "analysis menu" THEN EXIT DO
            LOOP
        END IF
        IF selected.options$ = "analysis menu" THEN
            SCREEN 0
            RETURN
        END IF LOOP UNTIL selected.options$ = "continue"

ELSE
    GOSUB translate                          'translate peaks into thicknesses
    GOSUB calc.volume                        'calculate volume of slice
END IF '------------------ save peak data to disk ------------------
IF save.peaks$ = "y" THEN CALL checkfile(peak.path$, peak.name$, peak.exten$, okay$, current.slice, slice, "peak", save.data$, finish)    'see if file exists CLS
LOCATE 13
PRINT TAB(28); "Saving Peak Data to File"

IF save.data$ = "y" THEN
    IF current.slice = 100 THEN
        OPEN peak.path$ + peak.name$ + "00" + peak.exten$ FOR OUTPUT AS #1
    ELSE
        OPEN peak.path$ + peak.name$ + LTRIM$(STR$(current.slice)) + peak.exten$ FOR OUTPUT AS #1
    END IF PRINT #1, CHR$(34) + "Version"; program.version; CHR$(34), CHR$(34) + DATE$ + CHR$(34)   'prints version number and date
    PRINT #1, splinevol(current.slice)                                                       'prints volume of slice
    PRINT #1, numpeaks%                                                                      'print number of peaks
    FOR y = 1 TO numpeaks%                                                                   'print peaks
        PRINT #1, USING "###.###"; CLNG(1000 * peakdom(y)) / 1000;
        PRINT #1, USING " #.###"; CLNG(1000 * peakran(y)) / 1000
    NEXT y
    CLOSE
END IF
```

```
END IF     save.data$ = "y"

'---------- save spline data to disk ----------
IF save.splines = "y" THEN

CALL checkfile(spline.path$, spline.name$, spline.exten$, okay$, current.slice, slice, "spline", save.data$, finish)

CLS
    LOCATE 13
    PRINT TAB(26); "Saving Spline Curve-Fit Data"
        IF save.data$ = "y" THEN
            IF current.slice = 100 THEN
                OPEN spline.path$ + spline.name$ + "00" + spline.exten$ FOR OUTPUT AS #1
            ELSE
                OPEN spline.path$ + spline.name$ + LTRIM$(STR$(current.slice)) + spline.exten$ FOR OUTPUT AS #1
            END IF PRINT #1, CHR$(34) + "version"; program.version; CHR$(34), CHR$(34) + DATE$ + CHR$(34)      'prints version number and date IF numpeaks% = 0 THEN                                      'this saves zero values so that the display part of the program will work
                PRINT #1, 1                                            'one peak
                PRINT #1, 0                                            'zero volume
                PRINT #1, length                                       'length of tube
                PRINT #1, 0, 0                                         'zero height
            ELSEIF numpeaks% = 1 THEN                                  'this saves the only marked peak
                PRINT #1, 1                                            'one peak
                PRINT #1, 0                                            'zero volume
                PRINT #1, length                                       'length of tube
                PRINT #1, USING "###.###"; CLNG(1000 * peakdom(1)) / 1000;           'domain and range of only thickness point
                PRINT #1, USING " #.###"; CLNG(1000 * peakran(1)) / 1000
            ELSE                                                       'this saves all the spline data
                PRINT #1, numout - 1                                   'number of data points
                PRINT #1, USING "#.####"; splinevol(current.slice)     'volume of slice
                PRINT #1, length                                       'length of tube FOR j = 1 TO numout - 1
                    PRINT #1, USING "###.###"; CLNG(1000 * outdom(j)) / 1000;
                    PRINT #1, USING " #.###"; CLNG(1000 * funcval(j)) / 1000         'spline data
                NEXT j END IF
            CLOSE
        END IF
        save.data$ = "y"
    END IF NEXT current.slice '---------- return to analyzing menu ----------
    IF start = 1 AND finish = slice THEN GOSUB volume.report           'if all the slices were analyzed, make a volume report
    KEY(25) OFF

RETURN
```

```
'--------------- mark peaks on graph --------------- mark.peaks:

' this routine takes the raw data, scales it, plots it on the screen, and
' allows the user to mark the peaks '--------------- define.variables --------------- exit$ = "false"
    quit$ = "false"

'--------------- mark peaks ---------------

' this routine turns on the key trapping so that the cursor can move
' and mark peaks on the graph '--------------- variables --------------- coord = 1                                           'set cursor position to first data point
    old = 1                                             'set last position also to first data point PUT (scaldom(coord), yaxismin), ycurs, XOR          'plot cursor
    PUT (xaxismin, scalren(coord)), xcurs, XOR KEY 15, CHR$(32) + CHR$(81)                         '3(keypad)--move right one point
    KEY 16, CHR$(32) + CHR$(13)                         '= --mark equal thickness peak
    KEY 17, CHR$(32) + CHR$(73)                         '9(keypad)--move right 1/30th of screen
    KEY 18, CHR$(32) + CHR$(71)                         '7(keypad)--move left 1/30th of screen
    KEY 19, CHR$(32) + CHR$(79)                         '1(keypad)--move left one point
    KEY 20, CHR$(32) + CHR$(74)                         '-(keypad)--mark decreasing thickness peak
    KEY 21, CHR$(32) + CHR$(78)                         '+(keypad)--mark increasing thickness peak
    KEY 22, CHR$(32) + CHR$(51)                         '< --goto previously marked peak
    KEY 23, CHR$(32) + CHR$(52)                         '> --goto next marked peak '--------------- set key values ---------------

ON KEY(1)  GOSUB peaks.marked                       'marks are marked, calculate volume and goto option menu
    ON KEY(2)  GOSUB zoom                               'goto zoom-in feature
    ON KEY(3)  GOSUB full.view                          'view all data
    ON KEY(4)  GOSUB clear.peaks                        'clear all marked peaks
    ON KEY(5)  GOSUB display.smoothed                   'display smoothed data - only if user confirmed peak recog.
    ON KEY(6)  GOSUB change.config                      'change peak recognition variables - only if user confirmed peak recog.
    ON KEY(10) GOSUB save.smooth                        'save smoothed data to disk - only id user confirmed peak recog.
    ON KEY(11) GOSUB home                               '8(keypad)--goto 1st data point
    ON KEY(12) GOSUB left5                              '4(keypad)--move left 5 data points
    ON KEY(13) GOSUB right5                             '6(keypad)--move right 5 data points
    ON KEY(14) GOSUB endd                               '2(keypad)--goto last data point
    ON KEY(15) GOSUB rightone                           '3(keypad)--move right one data point
    ON KEY(16) GOSUB equal                              '= --mark equal thickness peak
    ON KEY(17) GOSUB right20                            '9(keypad)--move right 20 data points
```

```
ON KEY(18) GOSUB left20              '7(keypad)--move left 20 data points
ON KEY(19) GOSUB leftone             '1(keypad)--move left one data point
ON KEY(20) GOSUB decr                '-(keypad)--mark decreasing thickness peak
ON KEY(21) GOSUB incr                '+(keypad)--mark increasing thickness peak
ON KEY(22) GOSUB before              '< --move to previous marked peak
ON KEY(23) GOSUB after               '> --move to next marked peak
ON KEY(25) GOSUB leave               'ESC--return to main menu NRL-IMD '------------------------- turn on keys -----------------------

GOSUB anal.keys.on

'------------------------- set-up position display ------------

GOSUB print.pos

'------------------------- wait for key press -----------------

DO
LOOP UNTIL quit$ = "true"

quit$ = "false"

'------------------------- turn off keys ----------------------

FOR y = 1 TO 25
    KEY(y) OFF
NEXT y

RETURN translate:
'------------------------- translate peaks into thicknesses ---

SCREEN 0
CLS
LOCATE 13
PRINT TAB(30); "Calculating Peaks..."
PRINT

REDIM peakdom(numpeaks% + 2), peakran(numpeaks% + 2)     'set up an array to place peak data
current.thickness = 0                                     'set thickness to zero
max.thickness = 0                                         'set maximum thickness to zero
min.thickness = 0                                         'set minimum thickness to zero
peak.num = 0                                              'set current peak number to zero FOR y = 1 TO number
    IF peaks(y) = 1 THEN                                  'increasing peak
        current.thickness = current.thickness + thickness 'increase current thickness
```

```
            peak.num = peak.num + 1                          'increase current peak number
            peakdom(peak.num) = domain(y)                    'place position of peak into peak array
            peakran(peak.num) = current.thickness            'place thickness into peak array
        ELSEIF peaks(y) = -1 THEN                            'decreasing peak
            current.thickness = current.thickness - thickness 'decrease current thickness
            peak.num = peak.num + 1                          'increase current peak number
            peakdom(peak.num) = domain(y)                    'place position of peak into peak array
            peakran(peak.num) = current.thickness            'place thickness into peak array
        ELSEIF peaks(y) = 2 THEN                             'equal peak
            peak.num = peak.num + 1                          'increase current peak number
            peakdom(peak.num) = domain(y)                    'place position of peak into peak array
            peakran(peak.num) = current.thickness            'place thickness into peak array
        END IF
        IF current.thickness > max.thickness THEN max.thickness = current.thickness    'find maximum thickness
        IF current.thickness < min.thickness THEN min.thickness = current.thickness
    NEXT y
    IF min.thickness > 0 THEN min.thickness = 0
RETURN calc.volume:
'----------------------------- spline data -------------------------------
'
' takes peak locations and thickness and calculates the volume of
' deposit on the tube CLS
    LOCATE 13
    PRINT TAB(25); "Calculating Volume of Slice..."
    PRINT IF numpeaks% > 1 THEN
        splinevol(current.slice) = spline(numpeaks%, peakdom%, peakran(), peakdom(), incout, errtol, spline.names, spline.paths, current.slice, slice, okay$, xaxismin,
            xaxismax, yaxismin, yaxismax, scr, spline.extent$, length, scan.start, scan.end, finish, numout, outdom(), funcval(), max.thickness)
        CLS
        LOCATE 13
        PRINT TAB(21); "Volume of Slice"; current.slice; USING " = #.###"; splinevol(current.slice);
        PRINT " cubic mm"
        PRINT
    ELSE
        splinevol(current.slice) = 0                         'if there are zero or one marked peaks, set the volume to zero
        CLS
        LOCATE 13
        PRINT TAB(29); "No Deposit on Slice "; LTRIM$(STR$(current.slice))
        PRINT
        PRINT
    END IF IF find.peak$ <> "a" THEN
        DO
            LOCATE 21, 30
            PRINT "press C to continue"
```

```
            wait$ = UCASE$(INPUT$(1))
            LOCATE 21, 51
            PRINT wait$
            IF wait$ = "C" THEN EXIT DO
      LOOP
   END IF
RETURN '---------- calculate total volume of deposit ----------
'------------------------------------------------------- volume.report:
   CLS
   volume = 0
   FOR current.slice = 1 TO slice
      IF current.slice = 100 THEN
         OPEN peak.path$ + peak.name$ + "00" + peak.exten$ FOR INPUT AS #1
      ELSE
         OPEN peak.path$ + peak.name$ + LTRIM$(STR$(current.slice)) + peak.exten$ FOR INPUT AS #1
      END IF
      INPUT #1, file.version$, file.date$
      INPUT #1, splinevol(current.slice)
      CLOSE #1
      volume = volume + splinevol(current.slice)       'adds up the volumes of each slice
   NEXT current.slice '-------------- save the volume profile --------------
   IF save.volume$ = "y" THEN
      CALL checkfile(volume.path$, volume.name$, volume.exten$, okay$, current.slice, slice, "volume profile", save.data$, finish)

LOCATE 13
      PRINT TAB(29); "Saving Final Results..."
      PRINT

IF save.data$ = "y" THEN
         OPEN volume.path$ + volume.name$ + volume.exten$ FOR OUTPUT AS #1
            PRINT #1, CHR$(34) + "Version"; program.version; CHR$(34) + DATE$ + CHR$(34)    'prints version number and date
            PRINT #1, USING "#.####"; volume
            PRINT #1, slice
            FOR x = 1 TO slice
               PRINT #1, x, USING "#.####"; splinevol(x)
            NEXT x
         CLOSE #1
      END IF
      save.data$ = "y"
   END IF '----------- print the volume profile ----------
   CLS
   PRINT "Volume Profile for: "; volume.name$
```

```
        PRINT USING "Total Volume = #.###"; volume;
        PRINT " cu mm"
        PRINT "slice"; TAB(15); "volume (cu mm)"
        PRINT "------------------------------------"
        counter = 0
        FOR x = 1 TO slice
            counter = counter + 1
            PRINT x; TAB(15); USING "#.###"; splinevol(x)
            IF counter = 17 THEN
                LOCATE 23
                PRINT "press any key to continue"
                zz$ = INPUT$(1)
                LOCATE 5
                counter = 0
            END IF
        NEXT x
        DO
            LOCATE 23, 27
            PRINT "press R to return to menu"
            wait$ = UCASE$(INPUT$(1))
            LOCATE 23, 54
            PRINT wait$
            IF wait$ = "R" THEN EXIT DO
        LOOP
RETURN '--------------------- plot data on screen ---------------------
'
plot.data:
    CLS
    LOCATE 13
    PRINT TAB(32); "Creating Graph..."
    PRINT
'--------------------- scale data to fit graph ---------------------
    REDIM scaldom(number), scalran(number)           'creates arrays to store data rescaled for video display
    FOR y = plot.start.num TO plot.end.num
        scaldom(y) = (domain(y) - plot.start) * (xaxismax - xaxismin) / plot.length + xaxismin    'scale tube data position
        scalran(y) = yaxismax - (range(y) - plot.min) * (yaxismax - yaxismin) / (plot.max - plot.min)    'scale tube data intensity
        IF find.peaks = "c" AND print.smooth$ = "y" THEN scalsmooth(y) = yaxismax - (smooth(y) - plot.min) * (yaxismax - yaxismin) / (plot.max - plot.min)
                            'scale smoothed data intensity
    NEXT y
'--------------------- draw graph ---------------------
'this routine draws both axes and labels the min and max values
```

```
SCREEN scr
CLS mult = (yaxismax - yaxismin) / 9

PRINT "   F1-Continue   F2-Zoom   F3-Full   F4-Clear Peaks  ";
IF find.peak$ = "c" THEN
    PRINT "F5-Smooth   F6-Config"
ELSE
    PRINT
END IF IF current.slice = 100 THEN
    PRINT TAB(25); "Scanned Data for Tube: "; tube.name$ + "00" + tube.exten$
ELSE
    PRINT TAB(25); "Scanned Data for Tube: "; tube.name$ + LTRIM$(STR$(current.slice)) + tube.exten$
END IF '----------- draw x-axis ------------
LINE (xaxismin, yaxismax + 1)-(xaxismax, yaxismax + 1), 2
FOR y = 1 TO 14
    LINE (y * 41 + xaxismin, yaxismax + 1)-(y * 41 + xaxismin, yaxismax + 6), 2
NEXT y LOCATE 23, 4
PRINT CLNG(100 * plot.start) / 100; "mm"
LOCATE 23, 73
PRINT CLNG(100 * plot.end) / 100

'----------- draw y-axis ------------
LOCATE 8
PRINT "I"
PRINT "n"
PRINT "t"
PRINT "e"
PRINT "n"
PRINT "s"
PRINT "i"
PRINT "t"
PRINT "y"

LINE (xaxismin - 1, yaxismin)-(xaxismin - 1, yaxismax), 2
FOR y = 1 TO 9
    LINE (xaxismin - 6, yaxismax - y * mult)-(xaxismin - 1, yaxismax - y * mult), 2
NEXT y LOCATE 2
PRINT CLNG(1000 * plot.max) / 1000
LOCATE 22
PRINT CLNG(1000 * plot.min) / 1000
```

```
IF scr = 9 THEN
    '-------------- draw horizontal grid --------------
    FOR y = 1 TO 9
        FOR xpos = xaxismin TO xaxismax STEP 10
            PSET (xpos, yaxismax - y * mult), 7
        NEXT xpos
    NEXT y '-------------- draw vertical grid --------------
    FOR y = 1 TO 14
        FOR ypos = yaxismin TO yaxismax STEP 10
            PSET (y * 41 + xaxismin, ypos), 7
        NEXT ypos
    NEXT y
END IF '-------------- plot data --------------
' this just plots the scaled data on the graph FOR y = plot.start.num TO plot.end.num
    IF (plot.end.num - plot.start.num) > 500 THEN
        PSET (scaldom(y), scalran(y)), 11
        IF print.smooth$ = "y" THEN
            IF scalsmooth(y) < yaxismax THEN PSET (scaldom(y), scalsmooth(y)), 12   'print smoothed data, if selected
        END IF
    ELSEIF (plot.end.num - plot.start.num) > 100 THEN                               'with all data, just use dots for points
        CIRCLE (scaldom(y), scalran(y)), 1, 11
        PAINT (scaldom(y), scalran(y)), 11, 11
        IF print.smooth$ = "y" THEN                                                 'with most of the data, use small circles
            IF scalsmooth(y) < yaxismax THEN
                CIRCLE (scaldom(y), scalsmooth(y)), 1, 12
                PAINT (scaldom(y), scalsmooth(y)), 12, 12                           'print smoothed data, if selected
            END IF
        END IF
    ELSE
        CIRCLE (scaldom(y), scalran(y)), 2, 11                                      'with <100 points, use bigger circles
        PAINT (scaldom(y), scalran(y)), 11, 11
        IF print.smooth$ = "y" THEN
            IF scalsmooth(y) < yaxismax THEN
                CIRCLE (scaldom(y), scalsmooth(y)), 2, 12
                PAINT (scaldom(y), scalsmooth(y)), 12, 12                           'print smoothed data if selected
            END IF
        END IF
    END IF
    SELECT CASE peaks(y)
        CASE 1
            PUT (scaldom(y) - 2, marky), plus, XOR                                  'put in marked peaks
        CASE 2                                                                      'increasing peak
            PUT (scaldom(y) - 2, marky), equal, XOR                                 'decreasing peak
```

```
            CASE -1
                PUT (scaldom(y) - 2, marky + 2), minus, XOR    'equal peak
        END SELECT
    NEXT y
RETURN '--------------------- print marked peaks ---------------------
'--------------------------------------------------------------
print.peaks:
'--------------------- print results --------------------------
    CLS
    PRINT "    Marked Peak Thicknesses"
    PRINT
    PRINT "peak #"; TAB(15); "x pos"; TAB(30); "thickness"
    PRINT TAB(15); "(in mm)"; TAB(30); "(in microns)"
    PRINT "---------------------------------------------------"
    z = 0
    FOR y = 1 TO numpeaks%
        z = z + 1
        PRINT y; TAB(15); USING "###.###"; CLNG(1000 * peakdom(y)) / 1000;
        PRINT TAB(30); USING "#.###"; peakran(y)
        IF z = 16 THEN
            LOCATE 23
            PRINT "press any key to continue"
            zz$ = INPUT$(1)
            z = 0
            LOCATE 6
            FOR xx = 6 TO 23
                PRINT SPACES(80)
            NEXT xx
            LOCATE 6
        END IF
    NEXT y
    DO
        LOCATE 23, 27
        PRINT "press R to return to menu"
        wait$ = UCASE$(INPUT$(1))
        IF wait$ = "R" THEN EXIT DO
    LOOP
RETURN '--------------------- plot thickness profile ----------------
'-------------------------------------------------------------
plot.thick:
```

```
SCREEN scr
CLS mult = (yaxismax - yaxismin) / 9                    'set distance between grid points '---------- display title ----------
    LOCATE 1, 10
    IF current.slice = 100 THEN
        PRINT TAB(15); "Thickness Profile for Tube: "; spline.name$ + "00" + spline.exten$; TAB(60); "slice: "; current.slice
    ELSE
        PRINT TAB(15); "Thickness Profile for Tube: "; spline.name$ + LTRIM$(STR$(current.slice)) + spline.exten$; TAB(60); "slice: "; current.slice
    END IF '---------- draw x-axis ----------
    LINE (xaxismin, yaxismax + 1)-(xaxismax, yaxismax + 1), 2

FOR y = 1 TO 14
        LINE (y * 41 + xaxismin, yaxismax + 1)-(y * 41 + xaxismin, yaxismax + 6), 2
    NEXT y LOCATE 23, 4
    PRINT "0 mm"
    LOCATE 23, 74
    PRINT length '---------- draw y-axis ----------
    LOCATE 8
    PRINT "m"
    PRINT "i"
    PRINT "c"
    PRINT "r"
    PRINT "o"
    PRINT "n"
    PRINT "s"

LINE (xaxismin - 1, yaxismin)-(xaxismin - 1, yaxismax), 2
    FOR y = 1 TO 9
        LINE (xaxismin - 6, yaxismax - y * mult)-(xaxismin - 1, yaxismax - y * mult), 2
    NEXT y LOCATE 2
    PRINT USING "#.##"; max.thickness
    LOCATE 22
    PRINT USING "#.##"; min.thickness IF scr = 9 THEN '---------- draw horizontal grid ----------

FOR y = 1 TO 9
        FOR xDOS = xaxismin TO xaxismax STEP 10
```

```
                  PSET (xpos, yaxismax - y * mult), 7
          NEXT xpos
     NEXT y '------- draw vertical grid ---------------
     FOR y = 1 TO 14
          FOR ypos = yaxismin TO yaxismax STEP 10
               PSET (y * 41 + xaxismin, ypos), 7
          NEXT ypos
     NEXT y
END IF '------- plot thicknesses ---------------
     FOR j = 1 TO numout - 1
          dom = outdom(j) * (xaxismax - xaxismin) / length + xaxismin
          ran = yaxismax - (funcval(j) - min.thickness) * (yaxismax - yaxismin) / (max.thickness - min.thickness)
          PSET (dom, ran), 11
     NEXT j '------- wait for user to continue ---------------
     DO
          LOCATE 23, 27
          PRINT "press R to return to menu"
          wait$ = UCASE$(INPUT$(1))
          IF wait$ = "R" THEN EXIT DO
     LOOP
     SCREEN 0
     CLS
RETURN '------------- find peaks --------------
'---------------------------------------
auto.find.peaks:

'------- set-up variables ---------------
     CLS
     LOCATE 13
     PRINT TAB(26); "Automatically Marking Peaks"

REDIM first(number), smooth(number), peak.pos.max(number, 2), peak.pos.min(number, 2), scalsmooth(number)
     numpeaks.max = 0                      'set number of maxima to zero
     numpeaks.min = 0                      'set number of minima to zero
     numpeaks% = 0                         'set number of peaks to zero
     status = 0                            'set difference between increasing and decreasing peaks to zero
     old.analysis$ = "n"                   'indicates a new analysis FOR x = 1 TO number                   'unmark all peaks
```

```
                peaks(x) = 0
        NEXT x
'----------- calculate first derivative -----------
        FOR x = 1 TO number - 1
                first(x) = (range(x + 1) - range(x)) / (domain(x + 1) - domain(x))
        NEXT x
'----------- start scanning -----------
        FOR x = 1 TO number - 1
                IF first(x) > pos.thresh THEN        'if deriv. exceeds threshold -- possible maxima occurring
                        max = first(x)                'set maximum value to this value
                        max.pos = x                   'set maximum location to this location
                        min = ABS(first(x))           'set minimum value to this value
                        min.pos = x                   'set minimum location to this location
                        consec = 0                    'set # of consecutive points with deriv. exceeding threshold to one IF x + max.pk.wid / (2 * dist.interval) > number THEN    'if search will go beyond data, limit search
                                stop.search = number - 1
                        ELSE
                                stop.search = x + max.pk.wid / (2 * dist.interval)  'otherwise search to find maxima for 1/2 max. width of peak
                        END IF FOR y = x TO stop.search      'search for maxima
                                IF first(y) > max THEN    'find maximum deriv. position and value
                                        max = first(y)
                                        max.pos = y
                                ELSEIF ABS(first(y)) < min THEN   'find minimum deriv. position and value (went closest to zero)
                                        min = ABS(first(y))
                                        min.pos = y
                                END IF
                                IF first(y) > 0 THEN      'find maxima by looking when deriv. passes through zero
                                        consec = 0
                                ELSE
                                        consec = consec + 1
                                END IF
                                IF consec = max.consec THEN EXIT FOR
                        NEXT y IF 2 * (min.pos - max.pos) < max.pk.wid / dist.interval AND 2 * (min.pos - max.pos) > min.pk.wid / dist.interval THEN  'if deriv. has definitely changed direction, then have gone through maxima
                                IF min.pos + max.pk.wid / (2 * dist.interval) > number THEN    'make sure peak is not too narrow or too wide
                                        stop.search = number - 1                               'make sure search does not exceed data set
                                ELSE
                                        stop.search = min.pos + max.pk.wid / (2 * dist.interval)
                                END IF
                                consec = 0
                                FOR y = min.pos TO stop.search                                 'search from maxima to 1/2 max. peak width to make
                                        IF first(y) < neg.thresh THEN                          ' sure maxima is a peak and not a plateau
                                                consec = consec + 1
```

```
          ELSE
             consec = 0
          END IF
          IF consec = max.consec THEN
             numpeaks.max = numpeaks.max + 1                    'incr. number of maximas
             peak.pos.max(numpeaks.max, 1) = min.pos            'set position and value
             peak.pos.max(numpeaks.max, 2) = range(min.pos)
             peaks(min.pos) = 1                                 'assign peak temporarily to be increasing thickness
             EXIT FOR
          END IF
       NEXT y
       x = min.pos + 1
    END IF
 ELSEIF first(x) < neg.thresh THEN                              'if deriv goes below threshold, possible minima occurring
    max = ABS(first(x))                                         'set max to value of deriv.
    max.pos = x                                                 'set max position to position
    min = ABS(first(x))                                         'set min to value of deriv.
    min.pos = x                                                 'set min position to position
    consec = 0                                                  'set number of consec points with deriv. below threshold to one IF x + max.pk.wid / (2 * dist.interval) > number THEN       'make sure search stays within data
       stop.search = number
    ELSE
       stop.search = x + max.pk.wid / (2 * dist.interval)       'otherwise search to find minima for 1/2 max peak width
    END IF
    FOR y = x TO stop.search                                    'search for minima
       IF ABS(first(y)) < min THEN                              'find minimum deriv position and value
          min = ABS(first(y))
          min.pos = y
       ELSEIF ABS(first(y)) > max THEN                          'find maximum deriv position and value
          max = ABS(first(y))
          max.pos = y
       END IF
       IF first(y) < 0 THEN                                     'find minima by looking when deriv passes through zero
          consec = 0
       ELSE
          consec = consec + 1
       END IF
       IF consec = max.consec THEN EXIT FOR
    NEXT y
    IF 2 * (min.pos - max.pos) < max.pk.wid / dist.interval AND 2 * (min.pos - max.pos) > min.pk.wid / dist.interval THEN   'if deriv has definitely changed direction, have gone through minima
       IF min.pos + max.pk.wid / (2 * dist.interval) > number THEN                         'make sure peak is not too narrow or too wide
          stop.search = number                                                             'make sure search stays within data set
       ELSE
          stop.search = min.pos + max.pk.wid / (2 * dist.interval)
       END IF
       consec = 0
       FOR y = min.pos TO stop.search                           'scan from minima to 1/2 max peak width
          IF first(y) > pos.thresh THEN                         'make sure minima is a peak and not a plateau
```

```
                ELSE
                    consec = consec + 1
                    consec = 0
                END IF
                IF consec = max.consec THEN
                    numpeaks.min = numpeaks.min + 1        'incr number of peaks
                    peak.pos.min(numpeaks.min, 1) = min.pos  'set peak position and value
                    peak.pos.min(numpeaks.min, 2) = range(min.pos)
                    peaks(min.pos) = 1                      'temporarily assign peak to be increasing thickness
                    EXIT FOR
                END IF
            NEXT y
            x = min.pos + 1
        END IF
    NEXT x '------------- find first and last peak position ---------------

IF peak.pos.min(1, 1) < peak.pos.max(1, 1) THEN
        first.peak.pos = peak.pos.min(1, 1)
    ELSE
        first.peak.pos = peak.pos.max(1, 1)
    END IF IF peak.pos.min(numpeaks.min, 1) > peak.pos.max(numpeaks.max, 1) THEN    'find first peak
        last.peak.pos = peak.pos.min(numpeaks.min, 1)
    ELSE
        last.peak.pos = peak.pos.max(numpeaks.max, 1)                        'find last peak
    END IF '------------- smooth data to find maximum thickness point ---------------

IF first.peak.pos > INT(move.average / 2) AND last.peak.pos < number - INT(move.average / 2) THEN  'enough points on both sides of
        FOR x = first.peak.pos TO last.peak.pos                                                        ' peaks to smooth data
            total = 0
            FOR y = x - INT(move.average / 2) TO x + INT(move.average / 2)                             'smooth with moving average
                total = total + range(y)
            NEXT y
            smooth(x) = total / (2 * INT(move.average / 2) + 1)
        NEXT x
    ELSEIF first.peak.pos <= INT(move.average / 2) AND last.peak.pos < number - INT(move.average / 2) THEN  'not enough data on left of
        FOR x = first.peak.pos TO INT(move.average / 2)                                                     ' peaks to smooth data
            total = 0
            FOR y = 1 TO x + INT(move.average / 2)                                                          'smooth with as many points as possible
                total = total + range(y)
            NEXT y
            smooth(x) = total / (x + INT(move.average / 2))
        NEXT x
        FOR x = INT(move.average / 2) + 1 TO last.peak.pos
            total = 0
```

```
            FOR y = x - INT(move.average / 2) TO x + INT(move.average / 2)
                total = total + range(y)
            NEXT y
            smooth(x) = total / (2 * INT(move.average / 2) + 1)
        NEXT x
    ELSEIF first.peak.pos > INT(move.average / 2) AND last.peak.pos >= number - move.average THEN   'not enough data to right
        FOR x = first.peak.pos TO number - (INT(move.average / 2) + 1)
            total = 0
            FOR y = x - INT(move.average / 2) TO x + INT(move.average / 2)
                total = total + range(y)
            NEXT y
            smooth(x) = total / (2 * INT(move.average / 2) + 1)                                     'smooth normally
        NEXT x
        FOR x = number - INT(move.average / 2) TO last.peak.pos
            total = 0
            FOR y = x - INT(move.average / 2) TO number
                total = total + range(y)
            NEXT y
            smooth(x) = total / (number - x + INT(move.average / 2))                                'smooth with as many points as possible
        NEXT x
    ELSEIF first.peak.pos <= INT(move.average / 2) AND last.peak.pos >= number - INT(move.average / 2) AND number > 100 THEN  'not enough data to lf or rt
        FOR x = first.peak.pos TO INT(move.average / 2)
            total = 0
            FOR y = 1 TO x + INT(move.average / 2)
                total = total + range(y)
            NEXT y
            smooth(x) = total / (x + INT(move.average / 2))                                         'smooth with as much as possible
        NEXT x
        FOR x = INT(move.average / 2) + 1 TO number - (INT(move.average / 2) + 1)
            total = 0
            FOR y = x - INT(move.average / 2) TO x + INT(move.average / 2)
                total = total + range(y)
            NEXT y
            smooth(x) = total / (2 * INT(move.average / 2) + 1)                                     'smooth normally
        NEXT x
        FOR x = number - INT(move.average / 2) TO last.peak.pos
            total = 0
            FOR y = x - INT(move.average / 2) TO number
                total = total + range(y)
            NEXT y
            smooth(x) = total / (number - x + INT(move.average / 2))                                'smooth with as much as possible
        NEXT x
    END IF '---------- find maximum thickness point ---------- max.thick.point = first.peak.pos
    max.thick = smooth(first.peak.pos)                                                              'set initial guess at first peak position
    FOR x = first.peak.pos TO last.peak.pos                                                         'find minimum in smoothed data and set it to be maximum thickness point
        IF smooth(x) < max.thick THEN
```

```
              max.thick = smooth(x)
              max.thick.point = x
          END IF
   NEXT x '-------------- convert peaks to program format -------------- numpeaks% = numpeaks.min + numpeaks.max          'set total number of peaks num.decr.pks = 0                                 'set number of decr. thickness peaks to zero FOR y = max.thick.point TO number
       IF peaks(y) = 1 THEN                         'set all peaks from maximum thickness to end to be decr. thickness
          peaks(y) = -1
          num.decr.pks = num.decr.pks + 1           'increment decr. peaks counter
       END IF
   NEXT y status = (numpeaks% - num.decr.pks) - num.decr.pks   'set status of peaks to be difference in incr. and decr. peaks '-------------- see if plateau occurs -------------- consec = 0                                       'set consec "flat" points to zero
   plateau$ = "n"                                   'indicate no plateau at this time
   FOR x = first.peak.pos TO last.peak.pos          'scan from first to last peak
       IF first(x) < pos.thresh AND first(x) > neg.thresh THEN    'if data is below threshold, possible plateau
          consec = consec + 1                       'see how long this lasts
       ELSE
          consec = 0                                'if data goes back above threshold, no plateau
       END IF
       IF consec > min.plateau / dist.interval THEN 'if enough data is flat, its a plateau
          plateau$ = "y"
          plateau.pos = CINT(x - min.plateau / dist.interval)
          EXIT FOR
       END IF
   NEXT x
   IF plateau$ = "y" THEN                           'if a plateau is indicated, change next peak to equal thickness
       FOR x = plateau.pos TO last.peak.pos         'loop from plateau point to last peak
           IF peaks(x) = 1 THEN                     'if next peak is incr., set to equal and adjust parameters
              peaks(x) = 2
              status = status - 1
              EXIT FOR
           ELSEIF peaks(x) = -1 THEN                'if next peak is decr., set to equal and adjust parameters
              peaks(x) = 2
              status = status + 1
              EXIT FOR
           END IF
       NEXT x
   END IF

RETURN
```

```
'------------------------- cursor routines ------------------------
'-----------------------------------------------------------------
' these routines are used in the peak marking section.  they are
' the cursor control routines leave:                                        'if ESC pressed return to main menu
        GOSUB keys.off
        LOCATE 23, 10
        PRINT SPACES(60);
        DO
                LOCATE 23, 25
                PRINT "Return to Analysis Menu (Y/N)";
                leave$ = UCASE$(INPUT$(1))
                IF leave$ = "Y" THEN
                        selected.option$ = "analysis menu"
                        quit$ = "true"
                        EXIT DO
                ELSEIF leave$ = "N" THEN
                        LOCATE 23, 10
                        PRINT SPACES(60);
                        GOSUB print.pos
                        EXIT DO
                END IF
        LOOP
        GOSUB anal.keys.on
RETURN
peaks.marked:                                 'exit peak marking routine
        GOSUB keys.off
        IF status < 0 THEN                    'make sure there are not more decr than incr peaks
                BEEP
                LOCATE 23
                PRINT SPACES(79)
                LOCATE 23, 10
                PRINT "There are more decr than incr peaks (neg thickness) continue (y/n)"
                DO
                        zz$ = UCASE$(INPUT$(1))
                        IF zz$ = "Y" THEN
                                quit$ = "true"
                                selected.option$ = "f1"
                                EXIT DO
                        ELSEIF zz$ = "N" THEN
                                quit$ = "false"
                                EXIT DO
                        END IF
                LOOP
                LOCATE 23
                PRINT SPACES(79)
                LOCATE 23, 4
```

```
            PRINT "0 mm"
            GOSUB print.pos
            LOCATE 23, 71
            PRINT length
      ELSE
            quit$ = "true"
            selected.options = "F1"
      END IF
      GOSUB anal.keys.on
RETURN zoom:                                          'data zoom in routine
      IF coord < plot.end.num THEN             'make sure cursor is not at last point
            KEY(1) OFF                         'turn off function keys  F1-finished marking
            KEY(4) OFF                         '   F4-clear peaks
            KEY(5) OFF                         '   F5-display smoothed data
            KEY(6) OFF                         '   F6-change configurations
            KEY(16) OFF                        'turn off peak marking keys  =-equal thickness
            KEY(20) OFF                        '   --decr. peak
            KEY(21) OFF                        '   +-incr. peak
            ON KEY(2) GOSUB zoom.boundary      'on F2 goto zoom boundary routine
            ON KEY(25) GOSUB exit.zoom         'on ESC goto quit zooming routine plot.start = domain(coord + 1)     'set leftmost distance to cursor position + 1
            old.plot.start.num = plot.start.num 'place old leftmost point into buffer, so old display can be restored
            plot.start.num = coord + 1         'set leftmost point to cursor position + 1
            PUT (xaxismin, scalran(coord)), xcurs, XOR  'remove horizontal part of cursor
            old = coord + 1                    'put cursor on next point, so zoom is over at least two points
            coord = coord + 1
            PUT (xaxismin, scalran(coord)), xcurs, XOR
            PUT (scaldom(coord), yaxismin), ycurs, XOR
            GOSUB print.pos                    'replot cursor LOCATE 1
      PRINT SPACES(80);
      LOCATE 1, 15
      PRINT "Mark Right Edge of Zoom and Press F2 (ESC to quit)"

right.zoom$ = "in"
      DO                                       'loop until user has positioned cursor at pressed RET
            KEY(1) OFF                         'turn off function keys  F1-finished marking
            KEY(4) OFF                         '   F4-clear peaks
            KEY(5) OFF                         '   F5-display smoothed data
            KEY(6) OFF                         '   F6-change configurations
            KEY(16) OFF                        'turn off peak marking keys  =-equal thickness
            KEY(20) OFF                        '   --decr. peak
            KEY(21) OFF                        '   +-incr. peak
            IF right.zoom$ = "q" THEN
                  ON KEY(2) GOSUB zoom
                  ON KEY(25) GOSUB leave
                  GOSUB anal.keys.on
                  RETURN                       'exit if user hits ESC
```

```
            END IF
   LOOP UNTIL right.zoom$ = "y"

GOSUB keys.off

'--------- find new min and max intensities for scaling data ---------
         plot.min = range(plot.start.num)
         plot.max = range(plot.start.num)
         FOR y = plot.start.num + 1 TO plot.end.num
             IF range(y) > plot.max THEN plot.max = range(y)
             IF range(y) < plot.min THEN plot.min = range(y)
         NEXT y '--------- display new zoomed data ---------
         GOSUB plot.data coord = plot.start.num
         old = plot.start.num
         PUT (scaldom(coord), yaxismin), ycurs, XOR      'set cursor position to leftmost point
         PUT (xaxismin, scalran(coord)), xcurs, XOR      'set last position to leftmost point
         GOSUB print.pos                                 'plot cursor at leftmost point '--------- turn peak marking keys on / zoom keys off ---------
         GOSUB anal.keys.on
         ON KEY(2) GOSUB zoom
         ON KEY(25) GOSUB leave

ELSE
         BEEP
     END IF
   RETURN zoom.boundary:
     IF coord >= plot.start.num THEN
         right.zoom$ = "y"
         plot.start = domain(plot.start.num - 1)             'set boundaries for zoomed data
         plot.start.num = plot.start.num - 1                 'make sure rightmost is not also leftmost
         plot.end = domain(coord)                            'right boundary has been marked
         plot.length = plot.end - plot.start                 'reset starting position of zoom
         plot.end.num = coord                                ' (moved so at least two points in zoom)
                                                             'set rightmost distance to cursor position
                                                             'calculate new length
                                                             'set rightmost point to cursor position
     ELSE
         BEEP
     END IF
   RETURN exit.zoom:
     PUT (scaldom(plot.start.num), yaxismin), ycurs, XOR     'exit zoom option and restore display
     plot.start.num = old.plot.start.num                     'remove left zoom boundary
     right.zoom$ = "q"                                       'reset leftmost point
                                                             'abort zoom LOCATE 1
     PRINT "  F1-Continue    F2-Zoom    F3-Full    F4-Clear Peaks   ";
     IF find.peak$ = "c" THEN
```

```
          ELSE
              PRINT "F5-Smooth     F6-Config"
              PRINT
          END IF
     RETURN
full.view:
     GOSUB keys.off
                                               'display all of the data plot.start = 0                            'display all data -- leftmost point 0 mm
     plot.end = length                         '                -- rightmost point length mm
     plot.length = length                      'length of display is length of tube
     plot.start.num = 1                        'first diplayed point is first data point
     plot.end.num = number                     'last displayed point is last data point
     plot.max = maxran                         'maximum intensity in displayed range is maximum intensity of all data points
     plot.min = minran                         'minimum intensity in displayed range is minimum intensity of all data points GOSUB plot.data                           'replot data coord = plot.start.num
     old = plot.start.num                      'set cursor position to first point
     PUT (scaldom(coord), yaxismin), ycurs, XOR
     PUT (xaxismin, scalran(coord)), xcurs, XOR
     GOSUB print.pos                           'plot cursor GOSUB anal.keys.on
     RETURN
clear.peaks:
     GOSUB keys.off                            'clear all marked peaks
     LOCATE 23, 18                             'turn key trapping off
     PRINT SPACES(50);
     DO
          LOCATE 23, 30
          PRINT "Clear All Peaks (Y/N)";
          which$ = UCASE$(INPUT$(1))
          exit$ = "y"
          SELECT CASE which$
               CASE "Y"
                    numpeaks% = 0              'set number of peaks to zero
                    status = 0                 'set difference between increasing and decreasing peaks to zero
                    FOR x = 1 TO number        'unmark all peaks
                         peaks(x) = 0
                    NEXT x
                    FOR x = 0 TO 5
                         LINE (xaxismin, marky + x)-(xaxismax, marky + x), 0   'blank peak line on screen display
                    NEXT x
               CASE "N"
               CASE ELSE
                    exit$ = "n"
          END SELECT
     LOOP UNTIL exit$ = "y"
```

```
'------------- turn key trapping back on --------------
         LOCATE 23, 30
         PRINT SPACE$(25)
         GOSUB print.pos                                           'print cursor position GOSUB anal.keys.on RETURN
display.smoothed:
    IF find.peak$ = "c" AND old.analysis$ = "n" THEN               'if user confirmed peak marking is selected, allow user
         GOSUB keys.off                                            ' to plot smoothed curve to look at quality of marking IF print.smooth$ = "y" THEN
              print.smooth$ = "n"
         ELSE
              print.smooth$ = "y"
         END IF GOSUB plot.data                                           'replot data coord = plot.start.num                                    'set cursor position to first point
         old = plot.start.num
         PUT (scaldom(coord), yaxismin), ycurs, XOR
         PUT (xaxismin, scalran(coord)), xcurs, XOR                'plot cursor
         GOSUB print.pos GOSUB anal.keys.on END IF
RETURN
change.config:
    IF find.peak$ = "c" THEN                                       'if user confirmed peak marking is selected, allow user to
         GOSUB keys.off                                            ' change peak marking configurations and remark peaks
         called.from.marking$ = "y"
         quit$ = "false"

GOSUB peak
         DO
         LOOP UNTIL quit$ = "true"
         GOSUB auto.find.peaks
         option.selected$ = "F6"

GOSUB anal.keys.on

END IF
RETURN
save.smooth:
    IF find.peak$ = "c" AND old.analysis$ = "n" THEN               'allow user to save smoothed data curve if user confirmed marking
         GOSUB keys.off                                            'turn key trapping off
         LOCATE 23, 8
         PRINT SPACE$(60)
         LOCATE 23, 9
         INPUT "enter file to save smoothed: ", smooth.file$
```

```
            IF smooth.file$ <> "" THEN
                OPEN smooth.file$ FOR OUTPUT AS #1
                    PRINT #1, CHR$(34) + "version"; program.version; CHR$(34), DATE$
                    FOR x = first.peak.pos TO last.peak.pos
                        PRINT #1, x * dist.interval, smooth(x)
                    NEXT x
                CLOSE #1
            END IF '---------- turn key trapping back on ------------
                GOSUB anal.keys.on LOCATE 23, 8
            PRINT SPACE$(71)
            LOCATE 23, 18
            GOSUB print.pos
        END IF
RETURN leftone:                                'moves the cursor left 1 point
    GOSUB keys.off
    IF coord > plot.start.num THEN
        old = coord                                             'make sure cursor isn't at start
                                                                'save old position
        coord = coord - 1                                       'decrease cursor position by one
        PUT (xaxismin, sca(ran(old)), xcurs, XOR               'remove old cursor
        PUT (scaldom(old), yaxismin), ycurs, XOR
        PUT (xaxismin, sca(ran(coord)), xcurs, XOR             'plot new cursor
        PUT (scaldom(coord), yaxismin), ycurs, XOR
    END IF
    GOSUB print.pos
    GOSUB anal.keys.on
RETURN left5:                                  'moves the cursor left 5 points
    GOSUB keys.off
    old = coord                                                 'save old position
    IF coord > plot.start.num THEN                              'make sure cursor isn't at start
        IF coord > plot.start.num + 4 THEN                      'if cursor is beyond 5 points of the start
            coord = coord - 5                                   '  move it 5 points to the left
        ELSE                                                    'otherwise move it to the start
            coord = plot.start.num
        END IF
        PUT (xaxismin, sca(ran(old)), xcurs, XOR               'remove old cursor
        PUT (scaldom(old), yaxismin), ycurs, XOR
        PUT (xaxismin, sca(ran(coord)), xcurs, XOR             'plot new cursor
        PUT (scaldom(coord), yaxismin), ycurs, XOR
    END IF
    GOSUB print.pos
    GOSUB anal.keys.on
RETURN
```

```
left20:                        'moves the cursor left 1/30th of the graph
    GOSUB keys.off
    old = coord                                    'save old position
    IF coord > plot.start.num THEN                 'make sure cursor isn't at start
        IF coord > plot.start.num + 19 THEN        'if cursor is beyond 5 points of the start
            coord = coord - 20                     ' move it 5 points to the left
        ELSE                                       'otherwise move it to the start
            coord = plot.start.num
        END IF
        PUT (xaxismin, scalran(old)), xcurs, XOR   'remove old cursor
        PUT (scaldom(old), yaxismin), ycurs, XOR
        PUT (xaxismin, scalran(coord)), xcurs, XOR 'plot new cursor
        PUT (scaldom(coord), yaxismin), ycurs, XOR
    END IF
    GOSUB print.pos
    GOSUB anal.keys.on
    RETURN rightone:                      'moves the cursor right 1 point
    GOSUB keys.off
    IF coord < plot.end.num THEN                   'make sure cursor isn't at the end
        old = coord                                'save old position
        coord = coord + 1                          'move cursor one point to the right
        PUT (xaxismin, scalran(old)), xcurs, XOR   'remove old cursor
        PUT (scaldom(old), yaxismin), ycurs, XOR
        PUT (xaxismin, scalran(coord)), xcurs, XOR 'plot new cursor
        PUT (scaldom(coord), yaxismin), ycurs, XOR
    END IF
    GOSUB print.pos
    GOSUB anal.keys.on
    RETURN right5:                        'moves the cursor right 5 points
    GOSUB keys.off
    old = coord                                    'save old position
    IF coord < plot.end.num THEN                   'make sure cursor isn't at the end
        IF coord < plot.end.num - 4 THEN           'if cursor is more than 5 pts from the end
            coord = coord + 5                      ' move it 5 points to the right
        ELSE                                       'otherwise move cursor to the end
            coord = plot.end.num
        END IF
        PUT (xaxismin, scalran(old)), xcurs, XOR   'remove cursor
        PUT (scaldom(old), yaxismin), ycurs, XOR
        PUT (xaxismin, scalran(coord)), xcurs, XOR 'plot new cursor
        PUT (scaldom(coord), yaxismin), ycurs, XOR
    END IF
    GOSUB print.pos
    GOSUB anal.keys.on
    RETURN
```

```
right20:    GOSUB keys.off                              'moves the cursor right 1/30th of the graph
            old = coord                                 'save old position
            IF coord < plot.end.num THEN                'make sure cursor isn't at the end
                IF coord < plot.end.num - 19 THEN       'if cursor is more than 5 pts from the end
                    coord = coord + 20                  '   move it 5 points to the right
                ELSE
                    coord = plot.end.num                'otherwise move cursor to the end
                END IF
                PUT (xaxismin, scalran(old)), xcurs, XOR    'remove cursor
                PUT (scaldom(old), yaxismin), ycurs, XOR
                PUT (xaxismin, scalran(coord)), xcurs, XOR  'plot new cursor
                PUT (scaldom(coord), yaxismin), ycurs, XOR
            END IF
            GOSUB print.pos
            GOSUB anal.keys.on
            RETURN home:       GOSUB keys.off                              'moves the cursor to the first point
            old = coord                                 'save old position
            coord = plot.start.num                      'move cursor to start
            PUT (xaxismin, scalran(old)), xcurs, XOR    'remove old cursor
            PUT (scaldom(old), yaxismin), ycurs, XOR
            PUT (xaxismin, scalran(coord)), xcurs, XOR  'plot new cursor
            PUT (scaldom(coord), yaxismin), ycurs, XOR
            GOSUB print.pos
            GOSUB anal.keys.on
            RETURN endd:       GOSUB keys.off                              'moves the cursor to the last point
            old = coord                                 'save old position
            coord = plot.end.num                        'move cursor to end
            PUT (xaxismin, scalran(old)), xcurs, XOR    'remove old cursor
            PUT (scaldom(old), yaxismin), ycurs, XOR
            PUT (xaxismin, scalran(coord)), xcurs, XOR  'plot new cursor
            PUT (scaldom(coord), yaxismin), ycurs, XOR
            GOSUB print.pos
            GOSUB anal.keys.on
            RETURN decr:       GOSUB keys.off                              'marks decreasing peak
            IF peaks(coord) = 0 THEN                    'if no previously marked peak,
                peaks(coord) = -1                       '   set to decr peak
                numpeaksX = numpeaksX + 1               '   increase number of peaks
                status = status - 1                     '   adjust status
```

```
        ELSEIF peaks(coord) = 1 THEN              'if already an incr peak,
            peaks(coord) = -1                     ' set to decr peak
            PUT (scaldom(coord) - 2, marky), plus, XOR   ' remove + sign
            status = status - 2                   ' adjust status
        ELSEIF peaks(coord) = 2 THEN              'if already an equal peak,
            peaks(coord) = -1                     ' set to decr peak
            PUT (scaldom(coord) - 2, marky), equal, XOR  ' remove = sign
            status = status - 1                   ' adjust status
        ELSE                                      'if already a decr peak,
            peaks(coord) = 0                      ' remove it -- set to no peaks
            numpeaksX = numpeaksX - 1             ' decrease number of peaks
            status = status + 1                   ' adjust status
        END IF
        PUT (scaldom(coord) - 2, marky + 2), minus, XOR  'plot a - sign (this will remove a - sign if it is already there)

GOSUB anal.keys.on
RETURN incr:                                             'marks increasing peak
        GOSUB keys.off
        IF peaks(coord) = 0 THEN                  'if no previously marked peaks,
            peaks(coord) = 1                      ' set to incr peak
            numpeaksX = numpeaksX + 1             ' increase number of peaks
            status = status + 1                   ' adjust status
        ELSEIF peaks(coord) = -1 THEN             'if already a decr peak,
            peaks(coord) = 1                      ' set to incr peak
            PUT (scaldom(coord) - 2, marky + 2), minus, XOR  ' remove - sign
            status = status + 2                   ' adjust status
        ELSEIF peaks(coord) = 2 THEN              'if already an equal peak,
            peaks(coord) = 1                      ' set to incr peak
            PUT (scaldom(coord) - 2, marky), equal, XOR  ' remove = sign
            status = status + 1                   ' adjust status
        ELSE                                      'if already an incr peak,
            peaks(coord) = 0                      ' remove it (set to no peak)
            numpeaksX = numpeaksX - 1             ' decrease number of peaks
            status = status - 1                   ' adjust status
        END IF
        PUT (scaldom(coord) - 2, marky), plus, XOR    'plot + sign (will remove + sign if it's already there)

GOSUB anal.keys.on
RETURN equal:                                            'marks level peak
        GOSUB keys.off
        IF peaks(coord) = 0 THEN                  'if no previously marked peaks,
            peaks(coord) = 2                      ' set to equal peak
            numpeaksX = numpeaksX + 1             ' increase number of peaks
        ELSEIF peaks(coord) = 1 THEN              'if already incr peak,
            peaks(coord) = 2                      ' set to equal peak
```

```
              PUT (scaldom(coord) - 2, marky), plus, XOR    ' remove + sign
              status = status - 1                           ' adjust status
          ELSEIF peaks(coord) = -1 THEN                     'if already decr peak,
              peaks(coord) = 2                              ' set to equal peak
              PUT (scaldom(coord) - 2, marky + 2), minus, XOR  ' remove - sign
              status = status + 1                           ' adjust status
          ELSE                                              'if already equal peak,
              peaks(coord) = 0                              ' remove it (set to no peaks)
              numpeaks% = numpeaks% - 1                     ' decrease number of peaks
          END IF
          PUT (scaldom(coord) - 2, marky), equal, XOR       'plot = sign (will remove it if it's already there)

GOSUB anal.keys.on
    RETURN before:                                                      'moves cursor to previous peak
    GOSUB keys.off
    FOR y = coord - 1 TO plot.start.num STEP -1
        IF peaks(y) = 1 OR peaks(y) = -1 OR peaks(y) = 2 THEN  'scan from peak to beginning of data
            PUT (xaxismin, scalran(coord)), xcurs, XOR         'if any peaks exist,
            PUT (scaldom(coord), yaxismin), ycurs, XOR         ' remove old cursor
            coord = y
            PUT (xaxismin, scalran(coord)), xcurs, XOR         ' move cursor
            PUT (scaldom(coord), yaxismin), ycurs, XOR         ' plot new cursor
            EXIT FOR
        END IF
    NEXT y
    GOSUB print.pos
    GOSUB anal.keys.on
    RETURN after:                                                       'moves cursor to next peak
    GOSUB keys.off
    FOR y = coord + 1 TO plot.end.num
        IF peaks(y) = 1 OR peaks(y) = -1 OR peaks(y) = 2 THEN  'scan from peak to end of data
            PUT (xaxismin, scalran(coord)), xcurs, XOR         'if any peak exists,
            PUT (scaldom(coord), yaxismin), ycurs, XOR         ' remove old cursor
            coord = y
            PUT (xaxismin, scalran(coord)), xcurs, XOR         ' move cursor
            PUT (scaldom(coord), yaxismin), ycurs, XOR         ' plot new cursor
            EXIT FOR
        END IF
    NEXT y
    GOSUB print.pos
    GOSUB anal.keys.on
    RETURN
```

```
REM $STATIC
SUB checkfile (path$, name$, extension$, okay$, current.slice, slice, type$, save.data$, finish)
'-----------------------------------------------------------------------
'this routine checks to see if a given file exists, and if so allows the user to delete it
'-----------------------------------------------------------------------
    save.data$ = "y"
    okay$ = "y"

OPEN path$ + name$ + LTRIM$(STR$(current.slice)) + extension$ FOR INPUT AS #1

IF okay$ = "y" THEN              'if there is no file by this name, the error.handler will turn okay$ into "n"
        BEEP
        CLOSE #1
        DO
            CLS
            LOCATE 12
            IF current.slice = 100 THEN
                PRINT TAB(15); "This "; type$; " data file ("; path$; name$; "00"; extension$; ") already exists"
            ELSE
                PRINT TAB(15); "This "; type$; " data file ("; path$; name$; LTRIM$(STR$(current.slice)); extension$; ") already exists"
            END IF
            PRINT
            PRINT TAB(20); "do you want to replace this file (Y/N)? ";
            del.file$ = UCASE$(INPUT$(1))
            PRINT del.file$
            IF del.file$ = "Y" THEN
                IF current.slice = 100 THEN
                    KILL tube.path$ + tube.name$ + "00" + tube.exten$
                ELSE
                    KILL tube.path$ + tube.name$ + LTRIM$(STR$(current.slice)) + tube.exten$
                END IF
                PRINT
                PRINT "File Deleted"
                save.data$ = "y"
                EXIT DO
            ELSEIF del.file$ = "N" THEN
                save.data$ = "n"
                EXIT DO
            END IF
        LOOP
    END IF

END SUB

FUNCTION spline (numpeaks%, peakdom(), peakran(), incout, errtol, spline.path$, spline.name$, spline.exten$, current.slice, slice, okay$, xaxismin, xaxismax, yaxismin, yaxismax, scr, spline.exten$, length, scan.start, scan.end, finish, numout, outdom(), funcval(), max.thickness)

' this routine calculates the volume of deposit from the peak locations
' and thicknesses.  the routine will then allow the user to save the curve
' that has been created
```

```
'------------------------------------------
'         cubic spline fit of x-y data
' from tempstor-p computer programming book, pg.147
'              adapted by R.E. Morris
'           further adapted by R. Wagner
'------------------------------------------

'---------------- initial set-up ---------------- peakdom(0) = peakdom(1) - incout                  'create another peak just before first with same thickness
peakran(0) = peakran(1)
peakdom(numpeaks% + 1) = peakdom(numpeaks%) + incout   'create another peak just after last peak with same thickness
peakran(numpeaks% + 1) = peakran(numpeaks%)
numpeaks% = numpeaks% + 2

FOR i = 0 TO numpeaks% - 1
    peakdom(i) = peakdom(i) / 10                  'increment number of peaks
    peakran(i) = peakran(i) * 1000                'adjust data so roundoff errors don't occur
NEXT i inc = incout / 10                                 'adjust spline output increment max.thickness = 0                                 'set initial maximum thickness to zero
maxoutdom = INT((peakdom(numpeaks% - 1) - peakdom(0)) / inc) + 1   'set number of data points necessary to fit
REDIM outdom(maxoutdom), funcval(maxoutdom)                        ' curve from first to last peak
DIM threet(maxoutdom + 1), twot(maxoutdom + 1), b(maxoutdom), deriv(maxoutdom)

'---------- setup table of x's for curve calc ----------
t = peakdom(0)
FOR numout = 0 TO maxoutdom
    outdom(numout) = t
    t = outdom(numout) + inc
NEXT numout
numout = numout - 1

'----------------------------------------
FOR i = 1 TO numpeaks% - 1
    x = peakdom(i) - peakdom(i - 1)
    tempstor = peakdom(i + 1) - peakdom(i - 1)
    b(i) = .5 * (x / tempstor)
    ta = (peakran(i + 1) - peakran(i)) / (peakdom(i + 1) - peakdom(i))
    tb = (peakran(i) - peakran(i - 1)) / (peakdom(i) - peakdom(i - 1))
    t = (ta - tb) / tempstor
    twot(i) = 2 * t
    threet(i) = 3 * t
NEXT i
```

```
twot(1) = 0
twot(numpeaks%) = 0
relaxfact = 8 - (4 * SQR(3))
uo = 0
DO
    maxvalt = 0
    FOR i = 2 TO numpeaks% - 1
        ta = -twot(i) - (b(i) * twot(i - 1))
        tb = (.5 - b(i)) * twot(i + 1)
        t = relaxfact * (ta - tb + threet(i))
        IF ABS(t) > maxvalt THEN
            maxvalt = t
        END IF
        twot(i) = twot(i) + t
    NEXT i
    du = ABS(uo - maxvalt)
    IF du < errtol THEN
        EXIT DO
    END IF
    uo = maxvalt
LOOP FOR i = 0 TO numpeaks% - 1
    threeta = twot(i + 1) - twot(i)
    threetb = peakdom(i + 1) - peakdom(i)
    threet(i) = threeta / threetb
NEXT i ERASE b '---------- compute functional and deriv values -------------
FOR j = 0 TO numout
    i = 1
    IF outdom(j) < peakdom(0) THEN
        EXIT FOR
    END IF
    DO
        i = i + 1
        IF i > numpeaks% THEN
            EXIT FOR
        END IF
    LOOP WHILE outdom(j) > peakdom(i)
    i = i - 1
    tempstor = outdom(j) - peakdom(i)
    t = outdom(j) - peakdom(i + 1)
    x = tempstor * t
    twot = twot(i) + (tempstor * threet(i))
    z = 1 / 6
```

```
            maxvalt = z * (twot(i) + twot(i + 1) + twot)
            relaxfact = (peakran(i + 1) - peakran(i)) / (peakdom(i + 1) - peakdom(i))
            funcval(j) = (relaxfact * tempstor) + peakran(i) + (x * maxvalt)
            deriv(j) = relaxfact + (tempstor + t) * maxvalt + (z * x * threet(i))
            IF funcval(j) > max.thickness THEN max.thickness = funcval(j)
        NEXT j
'-------------------------------------
        ERASE deriv, threet '----------- calculate volume --------
        intsdx = 0
        FOR i = 1 TO numpeaks% - 3
            intsdxa = .5 * (peakdom(i + 1) - peakdom(i)) * (peakran(i) + peakran(i + 1))
            intsdxb = (peakdom(i + 1) - peakdom(i)) ^ 3 * (twot(i) + twot(i + 1))
            intsdx = intsdx + intsdxa - intsdxb / 24
        NEXT i
        intsdx = intsdx / slice             'account for volume of a slice instead of a tube ERASE twot '---------------- final adjustments -----------
        FOR i = 1 TO numout - 1
            outdom(i) = outdom(i) * 10
            funcval(i) = funcval(i) / 1000.                'change spline data to original format
        NEXT i max.thickness = max.thickness / 1000               'adjust maximum thickness to original format FOR i = 0 TO numpeaks% - 1
            peakdom(i) = peakdom(i) * 10
            peakran(i) = peakran(i) / 1000.                'change data back to original format
        NEXT i
        numpeaks% = numpeaks% - 2                          'set the correct number of peaks spline = intsdx / 10000                            'adjust slice volume so it's correct

END FUNCTION
```

```
'***************************************************
'***************************************************
'****************                   ****************
'****************  Print Menu For NRL-IMD Program  ****************
'****************         Version 2.0              ****************
'****************                   ****************
'**************** Written by: Robert Wagner 7-18-90 ****************
'****************        modified: 7-22-91         ****************
'****************                   ****************
'***************************************************
'***************************************************

COMMON tube.path$, tube.name$, save.tube$, peak.path$, peak.name$, save.peak$
COMMON spline.path$, spline.name$, save.spline$, volume.path$, volume.name$
COMMON save.volume$, config.path$, config.name$, save.config$, slice
COMMON number, dist.interval, step.interval, type.tube$, scan.start, scan.end
COMMON length, motor.port$, translator, rotator, tran.speed, rot.speed
COMMON tran.rev, rot.rev, screw.rev, sample, timer.rate, n1, n2, timer.freq
COMMON low.scan, high.scan, io.add, interrupt, dma.level, thickness, errtol
COMMON incout, max.pk.wid, min.pk.wid, pos.thresh, neg.thresh, max.consec
COMMON min.plateau, move.average, find.peak$, printer.port$
COMMON scrtype$, key.break$, scr, alum.start, alum.end, alum.length
COMMON steel.start, steel.end, steel.length, base.path$, base.name$ COMMON tube.exten$, peak.exten$, spline.exten$, volume.exten$, config.exten$
COMMON already.running$, xaxismin, xaxismax, yaxismin, yaxismax, ticky, marky
COMMON current.menu$, max.number, max.slices, max.sample, program.version '$DYNAMIC                                           'metacommand to allow for large arrays '-------------- initalize variables --------------

ON ERROR GOTO error.handler

DIM plus(20) AS INTEGER                             'plus sign image
DIM minus(20) AS INTEGER                            'minus sign image
DIM equal(20) AS INTEGER                            'equal sign image DIM menu.color(9)

DIM domain(1, 1)                                    'domain of data
DIM range(1, 1)                                     'range of data
DIM peaks(1)                                        'peak array with type
DIM scaldom(1, 1)                                   'scaled domain data for graphing
DIM scalran(1, 1)                                   'scaled range data for graphing '-------- check to see if this program was called or run directly ---------
```

```
        IF already.running$ <> "y" THEN
            CLS
            LOCATE 12
            PRINT TAB(22); "Please run the NRL-IMD program first."
            PRINT
            PRINT TAB(25); "This program is not executable."
            END
        END IF '------------- main program ------------

GOSUB printer                       'display print menu

DO
        LOOP

END

'------------- subroutines ------------ error.handler:
        SELECT CASE ERR
            CASE 27                         'handles errors
                                            'out of paper error
                CLS
                LOCATE 12
                PRINT TAB(28); "Printer Is Out of Paper"
                DO
                    LOCATE 14
                    PRINT TAB(7); "Press C to continue printing, Q to return to print menu";
                    out.paper$ = UCASE$(INPUT$(1))
                    SELECT CASE out.paper$
                        CASE "C"
                            RESUME
                        CASE "Q"
                            RETURN
                    END SELECT
                LOOP
            CASE 25                         'printer not on error
                BEEP
                CLS
                LOCATE 13
                PRINT TAB(29); "The Printer is Not On"
                DO
                    LOCATE 14
                    PRINT TAB(7); "Press C to continue printing, Q to return to print menu";
                    print.off$ = UCASE$(INPUT$(1))
                    SELECT CASE print.off$
                        CASE "C"
                            RESUME
```

```
                    CASE "q"
                         RETURN
               END SELECT
          LOOP
     CASE 53
          okay$ = "n"                              'file not found error
          CLOSE
     CASE 68
          okay$ = "n"                              'device unavailable error
     CASE 76                                       'path not found error
          BEEP
          CLS
          LOCATE 12
          PRINT TAB(22); "Invalid Path Specified for Data File"
          PRINT
          PRINT TAB(22); "press any key to return to main menu"
          zz$ = INPUT$(1)
          CLOSE
          SCREEN 0
          CHAIN "NRL-IMD"
     CASE ELSE
          BEEP
          PRINT
          PRINT TAB(31); "Error"; ERR; " Occurred."
          PRINT
          PRINT TAB(20); "press any key to return to main program"
          zz$ = INPUT$(1)
          SCREEN 0
          CLOSE
          CHAIN "NRL-IMD"
     END SELECT
     RESUME NEXT keys.off:
     FOR x = 1 TO 25
          KEY(x) OFF                               'turns off key trapping
     NEXT x
RETURN quit:
     GOSUB keys.off                                'exits program
     CLOSE                                         'close all files PRINT
     PRINT TAB(21); "Are you sure you want to quit (Y/N)? ";
     leave$ = UCASE$(INPUT$(1))
     PRINT leave$
```

```
        IF leave$ = "Y" THEN END
RETURN

'-------------- printer menu -------------- printer:
    GOSUB printer.menu.init        'creates printer menu
    GOSUB printer.menu.on          ' initialize key trap settings
    GOSUB printer.menu             ' turn on key trapping
RETURN                             ' display print menu printer.menu.init:                 'initializes key traps
    KEY 15, CHR$(160) + CHR$(72)   'up--up
    KEY 16, CHR$(160) + CHR$(75)   'left--up
    KEY 17, CHR$(160) + CHR$(77)   'right-down
    KEY 18, CHR$(160) + CHR$(80)   'down--down
    KEY 19, CHR$(32)  + CHR$(28)   'RET-change
    KEY 25, CHR$(32)  + CHR$(1)    'ESC-quit ON KEY(1)  GOSUB main          'F1--return to main menu NRL.IMD
    ON KEY(2)  GOSUB config        'F2--goto config menu NRL.IMD
    ON KEY(4)  GOSUB disk          'F4--goto disk/hardware menu NRL.IMD
    ON KEY(11) GOSUB p.up          'left(cursor)--go up one menu item
    ON KEY(12) GOSUB p.up          'up(cursor)--go up one menu item
    ON KEY(15) GOSUB p.up          'left(keypad)--go up one menu item
    ON KEY(16) GOSUB p.up          'up(keypad)--go up one menu item
    ON KEY(13) GOSUB p.down        'right(cursor)--go down one menu item
    ON KEY(14) GOSUB p.down        'down(cursor)--go down one menu item
    ON KEY(17) GOSUB p.down        'right(keypad)--go down one menu item
    ON KEY(18) GOSUB p.down        'down(keypad)--go down one menu item
    ON KEY(19) GOSUB p.change      'RET--select menu item
    ON KEY(25) GOSUB p.quit        'ESC--return to print menu FOR x = 1 TO 9                 'deselect menu items (low intensity white)
        menu.color(x) = 7
    NEXT x
    menu.color(1) = 15             'hilight 1st menu item (high intensity white)
    menu.pos = 1                   'set cursor to 1st menu item
RETURN printer.menu.on:                   'turn on key trapping
    FOR x = 11 TO 19
        KEY(x) ON
    NEXT x
    KEY(1)  ON
    KEY(2)  ON
    KEY(4)  ON
    KEY(25) ON
RETURN
```

```
printer.menu:                                          'display print menu
    CLS
    PRINT TAB(28); "Print and Display Results"
    PRINT "------------------------------------------------------------------------------"
    PRINT
    COLOR menu.color(1): PRINT TAB(10); "Output Device ";
    COLOR 7: PRINT TAB(50); printer.port$
    PRINT
    PRINT "Print Data:"
    COLOR menu.color(2): PRINT TAB(10); "Scanned Tube Data ("; tube.exten$; ")"
    COLOR menu.color(3): PRINT TAB(10); "Marked Peaks Data ("; peak.exten$; ")"
    COLOR menu.color(4): PRINT TAB(10); "Curve-Fit Thickness ("; spline.exten$; ")"
    COLOR menu.color(5): PRINT TAB(10); "Volume Report ("; volume.exten$; ")"
    COLOR menu.color(6): PRINT TAB(10); "Program Configuration ("; config.exten$; ")"
    COLOR menu.color(7): PRINT TAB(10); "Print All"
    COLOR 7
    PRINT
    PRINT "Display Results:"
    COLOR menu.color(8): PRINT TAB(10); "Scanned Profile"
    COLOR menu.color(9): PRINT TAB(10); "Thickness Profile"
    COLOR 7
    PRINT
    PRINT
    PRINT TAB(7); "F1-Main Menu   F2-Configuration Menu   F4-Disk/Hardware Menu   ESC-quit"
RETURN p.quit: GOSUB quit                                     'exit program
        GOSUB printer.menu.on                          'otherwise turn key trapping on
        GOSUB printer.menu                             'display print menu
RETURN p.up:   IF menu.pos = 1 THEN                           'move "cursor" up one menu item
            menu.pos = 9                               'if cursor is at 1st item, move to last
            menu.color(1) = 7
        ELSE                                           'otherwise move cursor up
            menu.pos = menu.pos - 1
            menu.color(menu.pos + 1) = 7
        END IF
        menu.color(menu.pos) = 15                      'hilight menu item
        GOSUB printer.menu
RETURN p.down: IF menu.pos = 9 THEN                           'move "cursor" down one menu item
            menu.pos = 1                               'if cursor is at last item, move to 1st
            menu.color(9) = 7
        ELSE                                           'otherwise move cursor down
            menu.pos = menu.pos + 1
            menu.color(menu.pos - 1) = 7
```

```
        END IF
        menu.color(menu.pos) = 15             'hilight menu item
        GOSUB printer.menu
    RETURN p.change:
    GOSUB keys.off
    SELECT CASE menu.pos
        CASE 1
            DO
                LOCATE 21
                COLOR 15
                PRINT "select current output port  1) LPT1   2) LPT2   3) LPT3   4) Screen : ";
                COLOR 7
                port$ = UCASE$(INPUT$(1))
                PRINT port$
                exit$ = "y"
                SELECT CASE port$
                    CASE "1"
                        printer.port$ = "lpt1:"
                    CASE "2"
                        printer.port$ = "lpt2:"
                    CASE "3"
                        printer.port$ = "lpt3:"
                    CASE "4"
                        printer.port$ = "scrn:"
                    CASE CHR$(13)
                    CASE ELSE
                        exit$ = "n"
                END SELECT
            LOOP UNTIL exit$ = "y"
            exit$ = "n"
        CASE 2, 3, 4, 7, 8, 9                 'print tube,peak,spline or plot tube,spline data
            DO
                LOCATE 21
                COLOR 15
                PRINT TAB(22); "print O)ne, R)ange, or A)ll slices ";
                COLOR 7
                which$ = UCASE$(INPUT$(1))
                LOCATE 21, 58
                PRINT which$;
                quit$ = "n"
                SELECT CASE which$
                    CASE "O"
                        DO
                            COLOR 15
                            LOCATE 22, 33
                            INPUT "which slice: ", slice.num$
                            COLOR 7
                            slice.num = INT(VAL(slice.num$))
```

```
                    IF slice.num$ = "" THEN
                        exit$ = "y"
                        quit$ = "y"
                    ELSEIF slice.num >= 1 AND slice.num <= slice THEN   'set begin and end to selected slice
                        first = slice.num
                        last = slice.num
                        exit$ = "n"
                        quit$ = "n"
                    ELSE
                        BEEP
                        quit$ = "n"
                    END IF
            LOOP UNTIL quit$ = "y"
        CASE "R"
            DO
                COLOR 15
                LOCATE 22, 23
                INPUT "what range: begin - ", slice.beg$
                LOCATE 22, 49
                INPUT "end - ", slice.end$
                COLOR 7
                slice.beg = INT(VAL(slice.beg$))
                slice.end = INT(VAL(slice.end$))
                IF slice.beg$ = "" THEN
                    exit$ = "y"
                    quit$ = "y"
                ELSEIF slice.beg >= 1 AND slice.beg < slice.end AND slice.end <= slice THEN
                    first = slice.beg                                    'set beginning
                    last = slice.end                                     'set end
                    exit$ = "n"
                    quit$ = "n"
                ELSE
                    BEEP
                    quit$ = "n"
                END IF
            LOOP UNTIL quit$ = "y"
        CASE "A"
            first = 1                                                    'set beginning to first
            last = slice                                                 'set end to last
        CASE CHR$(13)
            exit$ = "n"
        CASE ELSE
    END SELECT IF exit$ <> "y" THEN
        SELECT CASE menu.pos
            CASE 2
                GOSUB print.tube                                         'print tube data
            CASE 3
                GOSUB print.peak                                         'print peak data
            CASE 4                                                       'print spline data
```

```
                CASE 7     GOSUB print.spline print.all$ = "y"                                     'print all data
                           GOSUB print.tube                                     'set flag
                           IF print.all$ = "y" THEN GOSUB print.peak            'print tube data
                           IF print.all$ = "y" THEN GOSUB print.spline          'if everything's okay, print peak data
                           IF print.all$ = "y" THEN GOSUB print.volume          'if everything's okay, print spline data
                           IF print.all$ = "y" THEN GOSUB print.config          'if everything's okay, print volume report
                           print.all$ = "n"                                     'if everything's okay, print configurations
                                                                                'turn off flag
                CASE 8     GOSUB plot.tube CASE 9     GOSUB plot.spline                                    'plot thickness profile END SELECT
             exit$ = "y"
        END IF
     LOOP UNTIL exit$ = "y"

CASE 5   GOSUB print.volume                                                'print volume report
              SCREEN 0

CASE 6   GOSUB print.config                                                'print configuration file
              SCREEN 0

END SELECT
GOSUB printer.menu.on                                                           'turn key trapping on
GOSUB printer.menu                                                              'display print menu
RETURN main:
     current.menu$ = "main"                                                     'return to main menu NRL-IMD
     CHAIN "NRL-IMD"                                                            'set menu to main
RETURN config:
     current.menu$ = "config"                                                   'return to config menu NRL-IMD
     CHAIN "NRL-IMD"                                                            'set menu to config
RETURN disk:
     current.menu$ = "disk"                                                     'return to disk menu NRL-IMD
     CHAIN "NRL-IMD"                                                            'set menu to disk
RETURN '------------- print tube data -------------
'
print.tube:
     CLS
     LOCATE 12
     PRINT TAB(32); "Scanned Tube Data"
```

```
okay$ = "y"
OPEN printer.port$ FOR OUTPUT AS #2
IF okay$ <> "y" THEN
    BEEP
    LOCATE 14
    PRINT TAB(7); "Printer Error.  Please make sure correct printer port was defined."
    PRINT
    PRINT TAB(22); "press any key to return to print menu"
    zz$ = INPUT$(1)
    RETURN
ELSE
    WIDTH #2, 80
END IF FOR current.slice = first TO last
    quit$ = "y"                                         'loop to print tube data
    DO
        CLS
        IF printer.port$ <> "scrn:" THEN
            LOCATE 14
            PRINT TAB(27); "Loading and Printing Slice"; current.slice
        END IF okay$ = "y"
        IF current.slice = 100 THEN
            OPEN tube.path$ + tube.name$ + "00" + tube.exten$ FOR INPUT AS #1
        ELSE
            OPEN tube.path$ + tube.name$ + LTRIM$(STR$(current.slice)) + tube.exten$ FOR INPUT AS #1
        END IF IF okay$ = "y" THEN                             'if file exists, print data
            quit$ = "y"
            PRINT #2, TAB(80 - INT(.5 * (29 + LEN(tube.name$)))); "Scanned Data for Tube - "; tube.name$; LTRIM$(STR$(current.slice)); tube.exten$
            PRINT #2,
            PRINT #2, TAB(2); "position (mm)"; TAB(29); "reflectance"
            PRINT #2, "------------------------------------------------------------------------------------"

INPUT #1, file.version$, file.date$          'load file version and date
            INPUT #1, numpts                             'load number of points
            REDIM domain(1, numpts), range(1, numpts)    'redim arrays to correct size
            counter = 0
            FOR z = 1 TO numpts                          'load data
                INPUT #1, domain(1, z), range(1, z)
                PRINT #2, TAB(5); USING "###.###"; CLNG(1000 * domain(1, z)) / 1000;
                PRINT #2, TAB(30); USING "####.#"; CLNG(10 * range(1, z)) / 10
                counter = counter + 1
                IF printer.port$ = "scrn:" AND counter = 17 THEN
                    PRINT TAB(27); "press any key to continue"
                    zz$ = INPUT$(1)
                    LOCATE 6
                    FOR blank.loop = 6 TO 22
```

```
                PRINT SPACES(80)
            NEXT blank.loop
            LOCATE 6
            counter = 0
        NEXT z
        END IF
        IF printer.port$ <> "scrn:" THEN
            PRINT #2, CHR$(12)                'form feed
        END IF
        CLOSE #1
    ELSE                                      'otherwise trap error
        BEEP
        CLS
        DO
            LOCATE 12
            IF current.slice = 100 THEN
                PRINT TAB(60 - LEN(tube.path$) - LEN(tube.name$)) / 2); tube.path$ + tube.name$ + "00" + tube.extens; " File Not Found"
            ELSE
                PRINT TAB(60 - LEN(tube.path$) - LEN(tube.name$)) / 2); tube.path$ + tube.name$ + LTRIM$(STR$(current.slice)) + tube.extens; " File Not Found"
            END IF
            PRINT
            PRINT TAB(22); "(T)ry again or R)eturn to print menu ";
            which$ = UCASE$(INPUT$(1))
            PRINT which$
            SELECT CASE which$
                CASE "T"
                    exit$ = "y"
                    quit$ = "n"
                CASE "R"
                    print.all$ = "n"    'this stops printing all the reports if selected
                    RETURN
                CASE ELSE
                    exit$ = "n"
            END SELECT
        LOOP UNTIL exit$ = "y"
    END IF
LOOP UNTIL quit$ = "y"

IF printer.port$ = "scrn:" THEN
    LOCATE 23
    PRINT TAB(24); "press R to return to print menu"
    DO
        zz$ = UCASE$(INPUT$(1))
    LOOP UNTIL zz$ = "R"
END IF NEXT current.slice
```

```
        CLOSE
        exit$ = "y"
    RETURN
'---------- print marked peaks ----------------
'---------------------------------------------- print.peak:

CLS
    LOCATE 12
    PRINT TAB(31); "Marked Peaks Data"

okay$ = "y"
    OPEN printer.port$ FOR OUTPUT AS #2
    IF okay$ <> "y" THEN
        BEEP
        LOCATE 14
        PRINT TAB(7); "Printer Error.  Please make sure correct printer port was defined."
        PRINT
        PRINT TAB(22); "press any key to return to print menu"
        zz$ = INPUT$(1)
        RETURN
    ELSE
        WIDTH #2, 80
    END IF FOR current.slice = first TO last
        quit$ = "y"
        DO                                                              'loop to print peaks
            CLS
            IF printer.port$ <> "scrn:" THEN
                LOCATE 14
                PRINT TAB(27); "Loading and Printing Slice"; current.slice
            END IF okay$ = "y"
            IF current.slice = 100 THEN
                OPEN peak.path$ + peak.name$ + "00" + peak.exten$ FOR INPUT AS #1
            ELSE
                OPEN peak.path$ + peak.name$ + LTRIM$(STR$(current.slice)) + peak.exten$ FOR INPUT AS #1
            END IF IF okay$ = "y" THEN                                         'if file exists, print data
                quit$ = "y"
                LOCATE 1
                PRINT #2, TAB(80 - INT(.5 * (29 + LEN(peak.name$)))); "Peak Data for Tube - "; peak.name$; LTRIM$(STR$(current.slice)); peak.exten$
                PRINT #2,
                PRINT #2, TAB(2); "position (mm)"; TAB(29); "thickness (microns)"
                PRINT #2, "--------------------------------------------------------------------------------"
                INPUT #1, file.version$, file.date$                     'load file version and date
                INPUT #1, vol, numpts                                   'load number of peaks
```

```
            REDIM domain(1, numpts), range(1, numpts)         'redim arrays to correct size
            counter = 0                                        'load peaks
            FOR z = 1 TO numpts
                INPUT #1, domain(1, z), range(1, z)
                PRINT #2, TAB(5); USING "###.###"; CLNG(1000 * domain(1, z)) / 1000;
            PRINT #2, TAB(30); USING "#.###"; CLNG(1000 * range(1, z)) / 1000
            counter = counter + 1
            IF printer.port$ = "scrn:" AND counter = 17 THEN
                PRINT TAB(27); "press any key to continue"
                zz$ = INPUT$(1)
                LOCATE 6
                FOR blank.loop = 6 TO 22
                    PRINT SPACE$(80)
                NEXT blank.loop
                LOCATE 6
                counter = 0
            END IF
        NEXT z IF printer.port$ <> "scrn:" THEN PRINT #2, CHR$(12)     'form feed CLOSE #1
    ELSE                                           'otherwise trap error
        BEEP
        CLS
        DO
            LOCATE 12
            IF current.slice = 100 THEN
                PRINT TAB((60 - LEN(peak.path$) - LEN(peak.name$)) / 2); peak.path$ + peak.name$ + "00" + peak.exten$; " File Not
                      Found"
            ELSE
                PRINT TAB((60 - LEN(peak.path$) - LEN(peak.name$)) / 2); peak.path$ + peak.name$ + LTRIM$(STR$(current.slice)) +
                      peak.exten$; " File Not Found"
            END IF
            PRINT
            PRINT TAB(22); "T)ry again or R)eturn to print menu ";
            which$ = UCASE$(INPUT$(1))
            PRINT which$
            SELECT CASE which$
                CASE "T"
                    exit$ = "y"
                    quit$ = "n"
                CASE "R"
                    print.all$ = "n"        'this stops printing all the reports if selected
                    RETURN
                CASE ELSE
                    exit$ = "n"
            END SELECT
        LOOP UNTIL exit$ = "y"
    END IF
LOOP UNTIL quit$ = "y"
```

```
        IF printer.port$ = "scrn:" THEN
            LOCATE 23
            PRINT TAB(24); "press R to return to print menu"
            DO
                zz$ = UCASE$(INPUT$(1))
            LOOP UNTIL zz$ = "R"
            END IF NEXT current.slice
    CLOSE
    exit$ = "y"
RETURN '--------------- print spline-fit thickness data -------------------
'------------------------------------------------------------------ print.spline:
    CLS
    LOCATE 12
    PRINT TAB(28); "Curve Fit Thickness Data"

okay$ = "y"
    OPEN printer.port$ FOR OUTPUT AS #2
    IF okay$ <> "y" THEN
        BEEP
        LOCATE 14
        PRINT TAB(7); "Printer Error.  Please make sure correct printer port was defined."
        PRINT
        PRINT TAB(22); "press any key to return to print menu"
        zz$ = INPUT$(1)
        RETURN
    ELSE    WIDTH #2, 80
    END IF FOR current.slice = first TO last
        quit$ = "y"
        DO
            CLS
            IF printer.port$ <> "scrn:" THEN
                LOCATE 14
                PRINT TAB(27); "Loading and Printing Slice"; current.slice
            END IF okay$ = "y"
            IF current.slice = 100 THEN                     'loop to print spline data
                OPEN spline.path$ + spline.name$ + "00" + spline.extens FOR INPUT AS #1
            ELSE
                OPEN spline.path$ + spline.name$ + LTRIM$(STR$(current.slice)) + spline.extens FOR INPUT AS #1
            END IF
```

```
IF okay$ = "y" THEN                                                         'if file exists, print it
    quit$ = "y"
    INPUT #1, file.version$, file.date$                                     'load file version and date
    INPUT #1, numpts                                                        'load number of data points
    INPUT #1, vol                                                           'load volume of slice
    INPUT #1, tube.length                                                   'load length of tube PRINT #2, TAB(80 - INT(.5 * (29 + LEN(spline.name$)))); "Curve-Fit Data for Tube - "; spline.name$; LTRIM$(STR$(current.slice));
    spline.exten$ PRINT #2,
    PRINT #2, TAB(26); USING "Volume of Slice = #.###"; vol
    PRINT #2,
    PRINT #2, TAB(2); "position (mm)"; TAB(29); "thickness (microns)"
    PRINT #2, "------------------------------------------------------------"

REDIM domain(1, numpts), range(1, numpts)                               'redim arrays to correct size
    counter = 0
    FOR z = 1 TO numpts                                                     'load and display spline data
        INPUT #1, domain(1, z), range(1, z)
        PRINT #2, TAB(5); USING "###.###"; CLNG(1000 * domain(1, z)) / 1000;
        PRINT #2, TAB(30); USING "#.###"; CLNG(1000 * range(1, z)) / 1000
        counter = counter + 1
        IF printer.port$ = "scrn:" AND counter = 15 THEN
            PRINT TAB(27); "press any key to continue"
            zz$ = INPUT$(1)
            LOCATE 8
            FOR blank.loop = 8 TO 22
                PRINT SPACE$(80)
            NEXT blank.loop
            LOCATE 8
            counter = 0
        END IF
    NEXT z IF printer.port$ <> "scrn:" THEN
        PRINT #2, CHR$(12)                                                  'form feed
    END IF CLOSE #1
ELSE
    BEEP
    CLS
    DO
        LOCATE 12
        IF current.slice = 100 THEN
            PRINT TAB((60 - LEN(spline.path$) - LEN(spline.name$)) / 2); spline.path$ + spline.name$ + "00" + spline.exten$; "
            File Not Found"
        ELSE
            PRINT TAB((60 - LEN(spline.path$) - LEN(spline.name$)) / 2); spline.path$ + spline.name$ + LTRIM$(STR$(current.slice))
            + spline.exten$; " File Not Found"
        END IF
        PRINT                                                               'otherwise trap error
```

```
                    PRINT TAB(22); "T)ry again or R)eturn to print menu ";
                    which$ = UCASE$(INPUT$(1))
                    PRINT which$
                    SELECT CASE which$
                        CASE "T"
                            exit$ = "y"
                            quit$ = "n"
                        CASE "R"
                            print.all$ = "n"
                            RETURN
                        CASE ELSE
                            exit$ = "n"
                    END SELECT
                LOOP UNTIL exit$ = "y"
            END IF
        LOOP UNTIL quit$ = "y"

IF printer.port$ = "scrn:" THEN
            LOCATE 23
            PRINT TAB(24); "press R to return to print menu"
            DO
                zz$ = UCASE$(INPUT$(1))
            LOOP UNTIL zz$ = "R"
        END IF NEXT current.slice
    CLOSE
    exit$ = "y"
RETURN
'------------- print volume report -------------------
'-----------------------------------------------------
print.volume:

CLS
    LOCATE 12
    PRINT TAB(33); "Volume Report"

okay$ = "y"
    OPEN printer.port$ FOR OUTPUT AS #2
    IF okay$ <> "y" THEN
        BEEP
        LOCATE 14
        PRINT TAB(7); "Printer Error.  Please make sure correct printer port was defined."
        PRINT
        PRINT TAB(22); "press any key to return to print menu"
        zz$ = INPUT$(1)
        RETURN
    ELSE    WIDTH #2, 80
```

'this stops printing all the reports if selected

```
END IF

CLS
IF printer.port$ <> "scrn:" THEN
    LOCATE 14
    PRINT TAB(25); "Loading and Printing Volume Report"
END IF quit$ = "y"
DO
    okay$ = "y"
    OPEN volume.path$ + volume.name$ + volume.exten$ FOR INPUT AS #1

IF okay$ = "y" THEN                                              'if file exists, print data
        quit$ = "y"

INPUT #1, file.version$, file.date$                          'load file version and date
        INPUT #1, total.vol                                          'load total volume
        INPUT #1, num.slices                                         'load number of slices
        PRINT #2, TAB(80 - INT(.5 * (29 + LEN(volume.name$)))); "Volume Profile for Tube - "; volume.name$; volume.exten$
        PRINT #2,
        PRINT #2, TAB(25); "Total Volume = "; USING "#.###"; total.vol;
        PRINT #2, " cubic mm"
        PRINT #2,
        PRINT #2, TAB(2); "slice"; TAB(29); "volume (cubic mm)"
        PRINT #2, "------------------------------------------------------------------"

REDIM domain(1, num.slices), range(1, num.slices)            'load slice and volume
        counter = 0
        FOR z = 1 TO num.slices
            INPUT #1, domain(1, z), range(1, z)
            PRINT #2, TAB(5); domain(1, z); TAB(30); USING "#.###"; range(1, z)
            counter = counter + 1
            IF printer.port$ = "scrn:" AND counter = 15 THEN
                PRINT TAB(27); "press any key to continue"
                zz$ = INPUT$(1)
                LOCATE 8
                FOR blank.loop = 8 TO 22
                    PRINT SPACE$(80)
                NEXT blank.loop
                LOCATE 8
                counter = 0
            END IF
        NEXT z IF printer.port$ <> "scrn:" THEN
            PRINT #2, CHR$(12)                                       'form feed
        END IF

CLOSE #1
        CLOSE #2
```

```
                ELSE                                            'otherwise trap error
                    BEEP
                    CLS
                    DO
                        LOCATE 12
                        PRINT TAB((60 - LEN(volume.path$) - LEN(volume.name$)) / 2); volume.path$ + volume.name$ + LTRIM$(STR$(current.slice)) +
                              volume.exten$; " File Not Found"
                        PRINT
                        PRINT TAB(22); "T)ry again or R)eturn to print menu ";
                        which$ = UCASE$(INPUT$(1))
                        PRINT which$
                        SELECT CASE which$
                            CASE "T"
                                exit$ = "y"
                                quit$ = "n"
                            CASE "R"
                                RETURN
                            CASE ELSE
                                exit$ = "n"
                        END SELECT
                    LOOP UNTIL exits = "y"
                END IF
            LOOP UNTIL quit$ = "y"

IF printer.port$ = "scrn:" THEN
                LOCATE 23
                PRINT TAB(24); "press R to return to print menu"
                DO
                    zz$ = UCASE$(INPUT$(1))
                LOOP UNTIL zz$ = "R"
            END IF
            exit$ = "y"
RETURN '--------------- print configuration data ----------------
'--------------------------------------------------------- print.config:
        CLS
        PRINT TAB(30); "Tube Configuration"
        okay$ = "y"
        OPEN printer.port$ FOR OUTPUT AS #2                     'if file exists, print data
        IF okay$ <> "y" THEN
            BEEP
            LOCATE 14
            PRINT TAB(7); "Printer Error.  Please make sure correct printer port was defined."
            PRINT
            PRINT TAB(22); "press any key to return to print menu"
            zz$ = INPUT$(1)
```

```
        ELSE
            RETURN
            WIDTH #2, 80
        END IF
    CLS
    IF printer.port$ <> "scrn:" THEN
        LOCATE 14
        PRINT TAB(23); "Loading and Printing Configuration"
    END IF quit$ = "y"
DO
    okay$ = "y"
    OPEN config.path$ + config.name$ + config.exten$ FOR INPUT AS #1

IF okay$ = "y" THEN
        quit$ = "y"

PRINT #2, TAB(28); "NRL-IMD Configuration Data"
        PRINT #2, "--------------------------------------------------------------"
        PRINT #2, PRINT #2, "Data Files"; TAB(60); "Save Enabled?"
        INPUT #1, hold1$, hold2$, hold3$
        PRINT #2, TAB(5); "Scanned Tube Data"; TAB(30); hold1$ + hold2$ + "" + tube.exten$; TAB(65); hold3$
        INPUT #1, hold1$, hold2$, hold3$
        PRINT #2, TAB(5); "Marked Peaks Data "; TAB(30); hold1$ + hold2$ + "" + peak.exten$; TAB(65); hold3$
        INPUT #1, hold1$, hold2$, hold3$
        PRINT #2, TAB(5); "Spline Curve Fit Data"; TAB(30); hold1$ + hold2$ + "" + spline.exten$; TAB(65); hold3$
        INPUT #1, hold1$, hold2$, hold3$
        PRINT #2, TAB(5); "Volume Report"; TAB(30); hold1$ + hold2$ + volume.exten$; TAB(65); hold3$
        INPUT #1, hold1$, hold2$, hold3$
        PRINT #2, TAB(5); "Tube Configuration"; TAB(30); hold1$ + hold2$ + config.exten$; TAB(65); hold3$
        PRINT #2, INPUT #1, hold1
        PRINT #2, "Number of Slices to Scan"; TAB(60); hold1
        INPUT #1, hold1
        PRINT #2, "Number of Scanned Points per Slice"; TAB(60); hold1
        INPUT #1, hold1, hold2
        PRINT #2, TAB(10); "Distance Between Points"; TAB(53); hold1; " mm"; TAB(67); hold2; " steps"
        INPUT #1, hold1$
        PRINT #2, "Type of Tube"; TAB(60); hold1$
        INPUT #1, hold1, hold2, hold3
        PRINT #2, "Scanning Range"; TAB(25); "start "; hold1; " mm"; TAB(44); "end "; hold2; " mm"; TAB(63); "length "; hold3; " mm"
        PRINT #2,
        PRINT #2, TAB(50); "translator"; TAB(65); "rotator"
        INPUT #1, hold1$, hold1, hold2
        PRINT #2, "Motor Number/Port"; TAB(30); hold1$; TAB(53); hold1; TAB(67); hold2
        INPUT #1, hold1, hold2
        PRINT #2, "Motor Speed"; TAB(53); hold1; TAB(67); hold2
```

```
INPUT #1, hold1, hold2
PRINT #2, "Number of Steps per Revolution"; TAB(53); hold1; TAB(67); hold2
INPUT #1, hold1
PRINT #2, "Translational Distance of One Screw Revolution"; TAB(60); hold1; " mm"
PRINT #2, IF printer.port$ = "scrn:" THEN
    LOCATE 23
    PRINT TAB(27); "press any key to continue"
    zz$ = INPUT$(1)
    LOCATE 4
    FOR blank.loop = 4 TO 23
        PRINT SPACE$(80)
    NEXT blank.loop
    LOCATE 4
END IF INPUT #1, hold1
PRINT #2, "Number of Times to Sample Each Data Point"; TAB(60); hold1
INPUT #1, hold1, hold2, hold3
PRINT #2, "Sampling Rate"; TAB(40); hold1; " Hz"; TAB(55); "n1 ="; hold2; " n2 ="; hold3
INPUT #1, hold1
PRINT #2, "A/D Board Frequency"; TAB(60); hold1 / 1000000; " MHz"
INPUT #1, hold1, hold2
PRINT #2, "Scanning Limits"; TAB(53); "low -"; hold1; TAB(67); "high -"; hold2
INPUT #1, hold1
PRINT #2, "I/O Address"; TAB(60); hold1
INPUT #1, hold1
PRINT #2, "Interrupt Level "; TAB(60); hold1
INPUT #1, hold1
PRINT #2, "DMA Level "; TAB(60); hold1
INPUT #1, hold1
PRINT #2, "Increment of Thickness of Deposit"; TAB(60); hold1; " microns"
INPUT #1, hold1
PRINT #2, "Error Tolerance"; TAB(60); hold1
INPUT #1, hold1
PRINT #2, "Output Increment"; TAB(60); hold1; " mm"
INPUT #1, hold1, hold2
PRINT #2, "Peak Widths"; TAB(51); "min -"; hold2; "mm"; TAB(65); "max -"; hold1; "mm"
INPUT #1, hold1, hold2
PRINT #2, "Peak Thresholds"; TAB(51); "pos "; hold1; TAB(65); "neg "; hold2
INPUT #1, hold1
PRINT #2, "Minimum Number of Consecutive Points"; TAB(60); hold1
INPUT #1, hold1
PRINT #2, "Minimum Length of Data Plateau"; TAB(60); hold1; "mm"
INPUT #1, hold1
PRINT #2, "Number of Points to Smooth Data by Averaging"; TAB(60); hold1

IF printer.port$ = "scrn:" THEN
```

```
            LOCATE 23
            PRINT TAB(27); "press any key to continue"
            zz$ = INPUT$(1)
            LOCATE 4
            FOR blank.loop = 4 TO 23
                PRINT SPACES(80)
            NEXT blank.loop
            LOCATE 4
        END IF INPUT #1, hold1$
        PRINT #2, "Peak Recognition Mode";
        SELECT CASE hold1$
            CASE "a"
                PRINT TAB(60); "Automatic Marking"
            CASE "c"
                PRINT TAB(60); "User Confirmed"
            CASE "m"
                PRINT TAB(60); "Manually Marked"
        END SELECT INPUT #1, hold1$
        PRINT #2, "Output Display"; TAB(60); hold1$
        INPUT #1, hold1$
        PRINT #2, "Screen Type"; TAB(60); hold1$
        INPUT #1, hold1$
        PRINT #2, "Enabled Keyboard Break During Scan"; TAB(60); hold1$
        INPUT #1, hold1$, hold2$
        PRINT #2, TAB(10); "Program "; hold1$; TAB(47); "Date Scanned:   "; hold2$ IF printer.port$ <> "scrn:" THEN
            PRINT #2, CHR$(12)                          'form feed
        END IF CLOSE #1
        CLOSE #2
        BEEP
        CLS
        DO
ELSE
            LOCATE 12
            PRINT TAB((60 - LEN(config.path$) - LEN(config.name$)) / 2); config.path$ + config.name$ + LTRIM$(STR$(current.slice)) + config.exten$; " File Not Found"
            PRINT
            PRINT TAB(22); "T)ry again or R)eturn to print menu ";
            which$ = UCASE$(INPUT$(1))
            PRINT which$
            SELECT CASE which$
                CASE "T"
                    exit$ = "y"
```

```
                              CASE "R"
                                   RETURN
                              CASE ELSE
                                   exit$ = "n"
                         END SELECT
                    LOOP UNTIL exit$ = "y"
               END IF
          LOOP UNTIL quit$ = "y"

IF printer.port$ = "scrn:" THEN
          LOCATE 23
          PRINT TAB(24); "press R to return to print menu"
          DO
               zz$ = UCASE$(INPUT$(1))
          LOOP UNTIL zz$ = "R"

END IF
          exit$ = "y"
RETURN

'---------------- plot scanned data ----------------
'
'
plot.tube:
     '---------- create peak marks ----------
          SCREEN scr                              'set screen type
          CLS LINE (12, 10)-(12, 14), 11
          LINE (10, 12)-(14, 12), 11
          GET (10, 10)-(14, 14), plus             'plus sign
          GET (10, 12)-(14, 12), minus            'minus sign
          LINE (20, 21)-(24, 21), 11
          LINE (20, 23)-(24, 23), 11
          GET (20, 20)-(24, 24), equal            'equal sign SCREEN 0                                'return to text screen
          CLS LOCATE 13
PRINT TAB(27); "Loading Scanned Data..."

'---------- load first tube to find number of data points ---------- okay$ = "y"
     OPEN tube.path$ + tube.name$ + LTRIM$(STR$(first)) + tube.exten$ FOR INPUT AS #1
          IF okay$ = "y" THEN                     'if file exists, load data
               INPUT #1, file.version$, file.date$   'load file version and date
               INPUT #1, num.pts                     'load number of data points
```

```
                    INPUT #1, dummy.domain, minran                    'load range of 1st point to set minimum range
                    CLOSE #1
        ELSE
            BEEP                                                      'otherwise trap error
            CLS
            DO
                LOCATE 12
                PRINT TAB((60 - LEN(tube.path$) - LEN(tube.name$)) / 2); tube.path$ + tube.name$ + "1" + tube.exten$; " File Not Found"
                PRINT
                PRINT TAB(22); "T)ry again or R)eturn to print menu ";
                which$ = UCASE$(INPUT$(1))
                PRINT which$
                SELECT CASE which$
                        CASE "T"
                                exit$ = "y"
                                quit$ = "n"
                        CASE "R"
                                RETURN
                        CASE ELSE
                                exit$ = "n"
                END SELECT
            LOOP UNTIL exit$ = "y"
        END IF '-------- set-up initial variables ------------
        REDIM domain(last - first, num.pts), range(last - first, num.pts)
        REDIM scaldom(last - first, num.pts), scalran(last - first, num.pts)
        REDIM peaks(num.pts)
        maxran = minran FOR current.slice = 0 TO last - first                                 'loop to print all the slices
        quit$ = "y"
        okay$ = "y"

DO
                IF current.slice = 100 THEN
                        OPEN tube.path$ + tube.name$ + "00" + tube.exten$ FOR INPUT AS #1
                ELSE
                        OPEN tube.path$ + tube.name$ + LTRIM$(STR$(current.slice + first)) + tube.exten$ FOR INPUT AS #1
                END IF
                IF okay$ = "y" THEN
                        quit$ = "y"

INPUT #1, file.version$, file.date$           'load file version and date
                        INPUT #1, num.pts                             'load number of data points '------------ load data and find min and max range ------------

FOR y = 1 TO num.pts
                                INPUT #1, domain(current.slice, y), range(current.slice, y)
                                IF range(current.slice, y) < minran THEN minran = range(current.slice, y)
```
                                                                                                        'dimension arrays for the correct number of data points

```
                        NEXT y
                        IF range(current.slice, y) > maxran THEN maxran = range(current.slice, y)
                CLOSE #1
        ELSE
                BEEP
                CLS
                DO
                    LOCATE 12
                    IF current.slice = 100 THEN
                            PRINT TAB((60 - LEN(tube.path$) - LEN(tube.name$)) / 2); tube.path$ + tube.name$ + "00" + tube.exten$; " File
                                                                                                                                 Not Found"
                    ELSE
                            PRINT TAB((60 - LEN(tube.path$) - LEN(tube.name$)) / 2); tube.path$ + tube.name$ + LTRIM$(STR$(current.slice +
                                                                                                first)) + tube.exten$; " File Not Found"
                    END IF
                    PRINT
                    PRINT TAB(22); "T)ry again or R)eturn to print menu ";
                    which$ = UCASE$(INPUT$(1))
                    PRINT which$
                    SELECT CASE which$
                        CASE "T"
                                exit$ = "y"
                                quit$ = "n"
                        CASE "R"
                                RETURN
                        CASE ELSE
                                exit$ = "n"
                    END SELECT
                LOOP UNTIL exit$ = "y"
            END IF
    LOOP UNTIL quit$ = "y"
NEXT current.slice
'---------------- check max range ---------------
    IF maxran = minran THEN
            maxran = minran + 1                                 'always make maxran greater than minran for scaling purposes
    END IF
'---------- check to see if this is an old analysis and peak file exists --------
    IF first = last THEN
            okay$ = "y"                                         'only load peaks if one tube was selected
        IF first = 100 THEN
                OPEN peak.path$ + peak.name$ + "00" + peak.exten$ FOR INPUT AS #1
        ELSE
                OPEN peak.path$ + peak.name$ + LTRIM$(STR$(first)) + peak.exten$ FOR INPUT AS #1
        END IF
```

```
IF okay$ = "y" THEN
    PRINT
    PRINT TAB(32); "Loading Analysis..."
    INPUT #1, file.version$, file.date$          'load file version and date
    INPUT #1, dummy, marked                       'load volume and number of peaks
    REDIM loaded.dom(marked + 1), loaded.ran(marked + 1)  'redim arrays for correct size
    FOR y = 1 TO marked                           'load peaks
        INPUT #1, loaded.dom(y)
        INPUT #1, loaded.ran(y)
    NEXT y
    CLOSE #1 z = 1
    FOR y = 1 TO number                           'go through all data
        IF domain(0, y) = loaded.dom(z) THEN
            IF loaded.ran(z) > loaded.ran(z - 1) THEN    'if peak thickness increases, mark as +
                peaks(y) = 1
                z = z + 1
            ELSEIF loaded.ran(z) = loaded.ran(z - 1) THEN  'if peak thickness is same, mark as =
                peaks(y) = 2
                z = z + 1
            ELSEIF loaded.ran(z) < loaded.ran(z - 1) THEN  'if peak thickness decreases, mark as -
                peaks(y) = -1
                z = z + 1
            END IF
        END IF
    NEXT y
END IF '-------------------------------- create graph --------------------------------

CLS
LOCATE 13
PRINT TAB(32); "Creating Graph..."
PRINT

' this routine takes the raw data, scales it, plots it on the screen, and
' allows the user to mark the peaks '-------------------------------- define variables ---------------------------- exit$ = "false"
quit$ = "false"

'-------------------------------- scale data to fit graph ---------------------

FOR x = 0 TO last - first
    FOR y = 1 TO num.pts
        scldom(x, y) = domain(x, y) * (xaxismax - xaxismin) / domain(x, num.pts) + xaxismin
```

```
            scalran(x, y) = yaxismax - range(x, y) * (yaxismax - yaxismin) / maxran
   NEXT y
NEXT x '-------------- draw graph --------------
' this routine draws both axes and labels the min and max values SCREEN scr
CLS mult = (yaxismax - yaxismin) / 9

PRINT TAB(25); "Scanned Data for Tube: "; tube.name$;
IF which$ = "O" THEN
   PRINT LTRIM$(STR$(first)); tube.extent$
ELSEIF which$ = "R" OR which$ = "A" THEN
   PRINT "("; LTRIM$(STR$(first)); "-"; LTRIM$(STR$(last)); ")"; tube.extent$
END IF '-------------- draw x-axis --------------

LINE (xaxismin, yaxismax + 1)-(xaxismax, yaxismax + 1), 2
FOR y = 1 TO 14
   LINE (y * 41 + xaxismin, yaxismax + 1)-(y * 41 + xaxismin, yaxismax + 6), 2
NEXT y LOCATE 23, 4
PRINT "0 mm"

LOCATE 23, 71
PRINT domain(0, num.pts)

LOCATE 23, 13
PRINT "legend:"

'-------------- draw y-axis --------------

LOCATE 8
   PRINT "I"
   PRINT "n"
   PRINT "t"
   PRINT "e"
   PRINT "n"
   PRINT "s"
   PRINT "I"
   PRINT "t"
   PRINT "y"

LINE (xaxismin - 1, yaxismin)-(xaxismin - 1, yaxismax), 2
FOR y = 1 TO 9
   LINE (xaxismin - 6, yaxismax - y * mult)-(xaxismin - 1, yaxismax - y * mult), 2
NEXT y
```

```
'-------------- draw grids -------------
IF scr = 9 THEN
    '------------- draw horizontal grid -------------
    FOR y = 1 TO 9
        FOR xpos = xaxismin TO xaxismax STEP 10
            PSET (xpos, yaxismax - y * mult), 7
        NEXT xpos
    NEXT y
    '------------- draw vertical grid -------------
    FOR y = 1 TO 14
        FOR ypos = yaxismin TO yaxismax STEP 10
            PSET (y * 41 + xaxismin, ypos), 7
        NEXT ypos
    NEXT y
END IF '-------------- plot data and legend colors ------------- legend.pos = 150
FOR current.slice = 0 TO last - first
    current.color = 15 - current.slice MOD 14
    IF current.color < 9 THEN current.color = current.color - 1   'set color of slice
                                                                   'this just eliminates dark gray color
    LINE (legend.pos, ticky - 4)-(legend.pos, ticky + 2), current.color   'draw legend mark
    FOR current.point = 1 TO num.pts                              'plot data
        PSET (scaldom(current.slice, current.point), scalran(current.slice, current.point)), current.color
        IF first = last THEN
            SELECT CASE peaks(current.point)
                CASE 1
                    PUT (scaldom(current.slice, current.point) - 2, marky), plus, XOR
                CASE 2
                    PUT (scaldom(current.slice, current.point) - 2, marky), equal, XOR
                CASE -1
                    PUT (scaldom(current.slice, current.point) - 2, marky + 2), minus, XOR
            END SELECT
        END IF
    NEXT current.point
    legend.pos = legend.pos + 4
NEXT current.slice '-------------- wait to exit -------------

DO
    LOCATE 23, 35
    PRINT "press Q to quit"
    which$ = UCASE$(INPUT$(1))
```

```
            IF which$ = "Q" THEN
                SCREEN 0
                RETURN
            END IF
        LOOP
RETURN '-------------- plot thickness profile -----------------
'--------------------------------------------- plot.spline:
    CLS
    LOCATE 13
    PRINT TAB(27); "Loading Curve-Fit Data..."

'---------- load all splines to find number of data points -------------
    max.pts = 0
    FOR current.slice = 0 TO last - first                              'loop through all slices
        okay$ = "y"
        OPEN spline.path$ + spline.name$ + LTRIM$(STR$(current.slice + first)) + spline.exten$ FOR INPUT AS #1
        IF okay$ = "y" THEN
            INPUT #1, file.version$, file.date$                        'load file version and date
            INPUT #1, num.pts                                          'load number of points
            CLOSE #1
            IF num.pts > max.pts THEN max.pts = num.pts                'find max. number of points
        ELSE
            BEEP
            CLS
            DO
                LOCATE 12
                PRINT TAB((60 - LEN(spline.path$) - LEN(spline.name$)) / 2); spline.path$ + spline.name$ + LTRIM$(STR$(current.slice +
                                 first)) + spline.exten$; " File Not Found"
                PRINT
                PRINT TAB(22); "T)ry again or R)eturn to print menu ";
                which$ = UCASE$(INPUT$(1))
                PRINT which$
                SELECT CASE which$
                    CASE "T"
                        exit$ = "y"
                        quit$ = "n"
                    CASE "R"
                        RETURN
                    CASE ELSE
                        exit$ = "n"
                END SELECT
            LOOP UNTIL exit$ = "y"
        END IF
    NEXT current.slice
```

```
'-------------- redimension arrays for number of points --------------
    REDIM domain(last - first, max.pts), range(last - first, max.pts)
    REDIM scaldom(last - first, max.pts), scalran(last - first, max.pts)
    maxran = 0
    minran = 0

FOR current.slice = 0 TO last - first                    'loop through each slice
    quit$ = "y"
    okay$ = "y"

DO
        IF current.slice = 100 THEN
            OPEN spline.path$ + spline.name$ + "00" + spline.exten$ FOR INPUT AS #1
        ELSE
            OPEN spline.path$ + spline.name$ + LTRIM$(STR$(current.slice + first)) + spline.exten$ FOR INPUT AS #1
        END IF IF okay$ = "y" THEN
            quit$ = "y"

INPUT #1, file.version$, file.date$           'load file version and date
            INPUT #1, num.pts                             'load number of points
            INPUT #1, vol                                 'load volume of slice
            INPUT #1, tube.length                         'load length of tube '-------------- load data and find max range --------------
            FOR y = 1 TO num.pts
                INPUT #1, domain(current.slice, y), range(current.slice, y)
                IF range(current.slice, y) > maxran THEN maxran = range(current.slice, y)
                IF range(current.slice, y) < minran THEN minran = range(current.slice, y)
            NEXT y
            IF minran > 0 THEN minran = 0

CLOSE #1

ELSE
            BEEP
            CLS
            DO
                LOCATE 12
                IF current.slice = 100 THEN
                    PRINT TAB((60 - LEN(spline.path$) - LEN(spline.name$)) / 2); spline.path$ + spline.name$ + "00" +
                                spline.exten$; " File Not Found"
                ELSE
                    PRINT TAB((60 - LEN(spline.path$) - LEN(spline.name$)) / 2); spline.path$ + spline.name$ +
                                LTRIM$(STR$(current.slice + first)) + spline.exten$; " File Not Found"
                END IF
                PRINT
                PRINT TAB(22); "T)ry again or R)eturn to print menu ";
                which$ = UCASE$(INPUT$(1))
```

```
            PRINT which$
            SELECT CASE which$
                    CASE "T"
                            exit$ = "y"
                            quit$ = "n"
                    CASE "R"
                            RETURN
                    CASE ELSE
                            exit$ = "n"
            END SELECT
    LOOP UNTIL exit$ = "y"
END IF
LOOP UNTIL quit$ = "y"

NEXT current.slice

'-------------- check max range --------------

IF maxran = 0 THEN                          'make sure maxran > minran for scaling purposes
    maxran = 1
END IF '-------------- create graph --------------

CLS
LOCATE 13
PRINT TAB(32); "Creating Graph..."
PRINT

' this routine takes the raw data, scales it, plots it on the screen, and
' allows the user to mark the peaks '------------------------- define variables ------------------------- exit$ = "false"
    quit$ = "false"

'------------------------- scale data to fit graph -------------------------

FOR x = 0 TO last - first
    FOR y = 1 TO num.pts
        scaldom(x, y) = domain(x, y) * (xaxismax - xaxismin) / tube.length + xaxismin
        scalran(x, y) = yaxismax - (range(x, y) - minran) * (yaxismax - yaxismin) / (maxran - minran)
    NEXT y
NEXT x '------------------------- draw graph -------------------------
' this routine draws both axes and labels the min and max values SCREEN scr
CLS
```

```
mult = (yaxismax - yaxismin) / 9

PRINT TAB(25); "Thickness Profile for Tube: "; spline.name$;
IF which$ = "O" THEN
    PRINT LTRIM$(STR$(first)); spline.exten$
ELSEIF which$ = "R" OR which$ = "A" THEN
    PRINT "("; LTRIM$(STR$(first)); "-"; LTRIM$(STR$(last)); ")" + spline.exten$
END IF '---------- draw x-axis ----------

LINE (xaxismin, yaxismax + 1)-(xaxismax, yaxismax + 1), 2
FOR y = 1 TO 14
    LINE (y * 41 + xaxismin, yaxismax + 1)-(y * 41 + xaxismin, yaxismax + 6), 2
NEXT y LOCATE 23, 4
PRINT "0 mm"
LOCATE 23, 71
PRINT tube.length LOCATE 23, 13
PRINT "legend:"

'---------- draw y-axis ----------

LOCATE 8
PRINT "m"
PRINT "i"
PRINT "c"
PRINT "r"
PRINT "o"
PRINT "n"
PRINT "s"

LINE (xaxismin - 1, yaxismin)-(xaxismax - 1, yaxismin), 2
FOR y = 1 TO 9
    LINE (xaxismin - 6, yaxismax - y * mult)-(xaxismin - 1, yaxismax - y * mult), 2
NEXT y LOCATE 2
PRINT USING "#.###"; maxran
LOCATE 22
PRINT USING "#.###"; minran '---------- draw grids ----------

IF scr = 9 THEN
    '---------- draw horizontal grid ----------
    FOR y = 1 TO 9
        FOR xpos = xaxismin TO xaxismax STEP 10
```

```
                            PSET (xpos, yaxismax - y * mult), 7
                    NEXT xpos
            NEXT y '------------ draw vertical grid ------------
            FOR y = 1 TO 14
                FOR ypos = yaxismin TO yaxismax STEP 10
                    PSET (y * 41 + xaxismin, ypos), 7
                NEXT ypos
            NEXT y

END IF

'--------------- plot data ---------------
    legend.pos = 150

FOR current.slice = 0 TO last - first
        current.color = 15 - current.slice MOD 14                                       'set color of slice
        IF current.color < 9 THEN current.color = current.color - 1                     'just eliminates a dark grey color
        LINE (legend.pos, ticky - 4)-(legend.pos, ticky + 2), current.color             'draws legend mark
        FOR current.point = 1 TO num.pts
            PSET (scaldom(current.slice, current.point), scalran(current.slice, current.point)), current.color    'plot data
        NEXT current.point
        legend.pos = legend.pos + 4
    NEXT current.slice '--------------- wait to exit ---------------
    DO
        LOCATE 23, 35
        PRINT "press Q to quit"
        which$ = UCASE$(INPUT$(1))

IF which$ = "Q" THEN
            SCREEN 0
            RETURN
        END IF

LOOP

RETURN
```

What is claimed is:

1. A device for measuring the thickness and volume of a deposit on a heater tube having a long axis and a circumference, comprising:
   (a) an optical probe wherein said probe is aimed at the tube;
   (b) a light source, optically coupled to said probe;
   (c) a detector of reflected light, for detecting reflected light of a predetermined wavelength, optically coupled to said probe;
   (d) means for longitudinally translating said optical probe, parallel to the long axis of the tube, thereby longitudinally traversing the tube;
   (e) means for axially rotating the tube about its long axis;
   (f) means for computing the thickness and volume of the deposit on the tube in accordance with the equations:

$$t = \frac{m\lambda}{2n\cos\theta}$$

where t is the thickness of the deposit at a point on the tube, m is the thickness multiplier, $\lambda$ is the wavelength of the detected light, n is the refractive index of the deposit, and $\theta$ is the angle at which the source optics are oriented with respect to the heater tube, and $$V_{slice} = \frac{\pi\left(2rA + \frac{A^2}{L}\right)}{d}$$

where $V_{slice}$ is the volume of the deposit on a longitudinal traversal of the tube, A is the area under the thickness profile along the tube, L is the length of the tube, r is the radius of the tube, and d is the number of longitudinal traversals around the tube circumference.

2. The device of claim 1 wherein said light source is capable of producing essentially monochromatic light in the wavelength range from about 300 nm to about 600 nm.

3. The device of claim 1 wherein said light source comprises a filtered xenon arc lamp, wherein said filter selectively transmits light within a wavelength band centered at about 460 nm.

4. The device of claim 1 wherein said means for translating comprises a stepper motor linked to a zero-backlash leadscrew assembly, wherein said optical probe is mounted on said leadscrew assembly, and wherein said means for rotating comprises a stepper motor mechanically coupled to the tube.

5. The device of claim 1 wherein said means for computing said thickness and volume of the deposit further comprises means for fitting measured deposit thicknesses along the tube to a cubic spline curve.

6. The device of claim 1 wherein said means for computing the thickness and volume of the deposit on the tube further comprises means for identifying peaks in the detected intensity of reflected light and means for correlating these peaks to longitudinal positions on the tube, wherein said means for identifying peaks in the detected intensity of reflected light further comprises:
   (a) means for determining the first derivative dI/dx of the variations in the intensity of light, where I is the intensity of the reflected light and x is the position of said probe along the length of the tube;
   (b) means for comparing the first derivative data to predetermined upper and lower thresholds, and labelling as possible peaks all the points along said longitudinal traversal of the tube that correspond to local maxima and minima in the first derivative data that are outside said upper and lower thresholds;
   (c) means for comparing the widths of said local maxima and minima in the first derivative data that correspond with labelled possible peaks to a predetermined maximum width threshold and a predetermined minimum width threshold, and labelling as peaks all labelled possible peaks that correspond to local maxima and minima in the first derivative data that are neither wider than the maximum width threshold nor narrower than the minimum width threshold.

7. The device of claim 6 further comprising:
   (a) means for prompting an operator with the labelled peaks;
   (b) means for receiving input from the operator;
   (c) adding or removing labelled peaks, based upon said input.

8. The device of claim 7 further comprising means for identifying a point of maximum deposit thickness on a longitudinal traversal of the tube, wherein said means for identifying a point of maximum deposit thickness on a longitudinal traversal of the tube further comprises:
   (a) means for computing a moving average of reflected light intensity from the first peak to the last peak on the longitudinal traversal, whereby the data from the first peak to the last peak is smoothed;
   (b) means for identifying a minimum intensity point along this moving average curve, and labelling said minimum intensity point as the point of maximum deposit thickness on the longitudinal traversal.

9. The device of claim 7, further comprising means for identifying points of maximum deposit thickness on a longitudinal traversal of the tube, wherein said means for identifying points of maximum deposit thickness on a longitudinal traversal of the tube further comprises:
   (a) means for computing a moving average of the reflected light intensity from the first peak to the last peak on the longitudinal traversal, whereby the data from the first peak to the last peak is smoothed;
   (b) means for identifying the minimum intensity point along this moving average curve, and labelling the peak located at or immediately preceding this point as a first point of maximum deposit thickness on the traversal;
   (c) means for labelling the peak immediately following said point of maximum deposit thickness as a second point of maximum deposit thickness in the case where said first point of maximum deposit thickness and said second point of maximum deposit thickness are separated by more than a predetermined distance on the tube.

10. A method for measuring the thickness and volume of a deposit on a heater tube comprising:
   (a) producing light;
   (b) transmitting said light to an optical probe for transmission onto and from the tube, wherein said probe is optically coupled to a light detector and wherein said probe is aimed at the tube;
   (c) measuring the intensity of light of a predetermined wavelength reflected from said tube;

(d) concurrently with measuring reflected light, translating said optical probe along the length of the tube from a starting position to an ending position, returning the probe to its original position, rotating the tube by a predetermined distance, and repeating this translation and rotation cycle until the tube has been rotated at least 360°;

(e) identifying peaks in the measured intensity of reflected light, and correlating these peaks to their longitudinal position on the tube, so that there is a first peak and a last peak on each longitudinal traversal of the tube;

(f) computing the thickness of the deposit at each of said peaks in a longitudinal traversal of the tube, thereby generating the deposit thickness profile for a longitudinal traversal of the tube;

(g) computing from said deposit thickness profile the deposit volume for a longitudinal traversal of the tube;

(h) summing the deposit volumes for the longitudinal traversals of tube, thereby calculating the total deposit volume on the tube.

11. The method of claim 10, wherein said light produced in step (a) is essentially monochromatic light in the wavelength range from about 300 nm to about 600 nm.

12. The method of claim 11, wherein said light is produced by a filtered xenon arc lamp and has a narrow wavelength band centered at about 460 nm.

13. The method of claim 10, wherein said rotation of the tube is carried out by a stepper motor, and wherein said translation of said optical probe is carried out by a stepper motor linked to a zero-backlash leadscrew assembly.

14. The method of claim 10, wherein the step of computing the thickness of the deposit at each of said peaks in a longitudinal traversal of the tube, thereby generating the deposit thickness profile for a longitudinal traversal of the tube, is carried out according to the equation:

$$t = \frac{m\lambda}{2n\cos\theta}$$

where t is the thickness of the deposit at a point on the tube, m is the thickness multiplier, $\lambda$ is the wavelength of the detected reflected light, n is the refractive index of the deposit, and $\theta$ is the angle at which the source optics are oriented with respect to the heater tube.

15. The method of claim 14, wherein the step of computing the thickness of the deposit at each of said peaks in a longitudinal traversal of the tube, thereby generating the deposit thickness profile for a longitudinal traversal of the tube, further comprises fitting measured deposit thicknesses along the tube to a cubic spline curve.

16. The method of claim 14, wherein the step of computing from said deposit thickness profile the deposit volume for a longitudinal traversal of the tube is carried out according to the equation:

$$V_{slice} = \frac{\pi\left(2rA + \frac{A^2}{L}\right)}{d}$$

where $V_{slice}$ is the volume of the deposit on a longitudinal traversal of the tube, r is the radius of the tube, A is the area under the thickness profile along the tube, which is computed by numerical integration under the deposit thickness profile, L is the length of the tube and d is the number of longitudinal traversals of the tube.

17. The method of claim 10, wherein the step of identifying peaks further comprises:

(a) determining the first derivative dI/dx of the variations in the intensity of reflected light, where I is the intensity of the reflected light and x is the position of said probe along the length of the tube;

(b) comparing the first derivative data to predetermined upper and lower thresholds, and labelling as possible peaks all the points along the tube that correspond to local maxima and minima in the first derivative data that are outside these thresholds;

(c) comparing the widths of said local maxima and minima in the first derivative data that correspond to labelled possible peaks to predetermined width thresholds, and labelling as peaks all labelled possible peaks that correspond to local maxima and minima in the first derivative data that are neither wider than the maximum width threshold nor narrower than the minimum width threshold.

18. The method of claim 17, further comprising:

(a) prompting an operator with the labelled peaks;
(b) receiving input from the operator;
(c) adding or removing labelled peaks, based upon said input.

19. The method of claim 18, further comprising identifying a point of maximum deposit thickness on a longitudinal traversal of the tube, wherein the step of identifying a point of maximum deposit thickness on a longitudinal traversal of the tube further comprises:

(a) computing a moving average of reflected light intensity from the acquired data from the first peak to the last peak on the longitudinal traversal, thereby smoothing the data from the first peak to the last peak;

(b) identifying a minimum intensity point along this moving average curve, and labelling this point as a point of maximum deposit thickness on the longitudinal traversal.

20. The method of claim 18, further comprising the step of identifying points of maximum deposit thickness on a longitudinal traversal of the tube, wherein the step of identifying points of maximum deposit thickness on a longitudinal traversal of the tube further comprises the steps of:

(a) computing a moving average of the reflected light intensity from the first peak to the last peak on the longitudinal traversal, whereby the data from the first peak to the last peak is smoothed;

(b) identifying a minimum intensity point along this moving average curve, and labelling a peak located at or immediately preceding this point as a first point of maximum deposit thickness on the longitudinal traversal;

(c) labelling the peak immediately following said point of maximum deposit thickness as a second point of maximum deposit thickness in the case where said first point of maximum deposit thickness and said second point of maximum deposit thickness are separated by more than a predetermined distance on the tube.

* * * * *